US007700774B2

(12) United States Patent
Baruah et al.

(10) Patent No.: US 7,700,774 B2
(45) Date of Patent: Apr. 20, 2010

(54) HETEROCYCLIC COMPOUNDS AND THEIR PHARMACEUTICAL COMPOSITIONS

(75) Inventors: Anima Baruah, Andra Pradesh (IN); Ish Khanna, Alpharetta, GA (US); Sivaram Pillarisetti, Norcross, GA (US)

(73) Assignee: Dr. Reddy's Laboratories Ltd., Ameerpet, Hyderabad (IN)

( * ) Notice: Subject to any disclaimer, the term of this patent is extended or adjusted under 35 U.S.C. 154(b) by 1019 days.

(21) Appl. No.: 11/314,299

(22) Filed: Dec. 20, 2005

(65) Prior Publication Data

US 2006/0135551 A1 Jun. 22, 2006

Related U.S. Application Data

(60) Provisional application No. 60/638,084, filed on Dec. 20, 2004.

(51) Int. Cl.
*C07D 215/38* (2006.01)
(52) U.S. Cl. ...................... 546/123; 514/300
(58) Field of Classification Search ................ 546/123; 514/300
See application file for complete search history.

(56) References Cited

U.S. PATENT DOCUMENTS

| 6,140,343 | A | 10/2000 | DeNinno et al. |
| 6,147,090 | A | 11/2000 | DeNinno et al. |
| 6,313,142 | B1 | 11/2001 | Damon et al. |
| 6,600,045 | B2 | 7/2003 | Damon et al. |
| 6,689,897 | B2 | 2/2004 | Damon et al. |
| 6,706,881 | B2 | 3/2004 | Damon et al. |
| 2003/0054037 | A1 | 3/2003 | Babcock et al. |
| 2003/0072801 | A1 | 4/2003 | Curatolo et al. |
| 2003/0104063 | A1 | 6/2003 | Babcock et al. |
| 2003/0170309 | A1 | 9/2003 | Babcock et al. |
| 2003/0198674 | A1 | 10/2003 | Curatolo et al. |
| 2004/0039018 | A1 | 2/2004 | Ruggeri |
| 2004/0053842 | A1 | 3/2004 | Nguyen et al. |
| 2004/0185102 | A1 | 9/2004 | Friesen et al. |

FOREIGN PATENT DOCUMENTS

| WO | WO-00/0017164 A1 | 3/2000 |
| WO | WO-00/0017165 A1 | 3/2000 |
| WO | WO-021011710 A2 | 2/2002 |
| WO | WO-03/000295 A2 | 1/2003 |
| WO | WO-03/063832 A1 | 8/2003 |
| WO | 2004/52863 | * 6/2004 |
| WO | WO-2005/030185 A2 | 4/2005 |
| WO | WO-2005/095395 A2 | 10/2005 |
| WO | WO-2005/095409 A2 | 10/2005 |
| WO | WO-2005/097806 A1 | 10/2005 |

OTHER PUBLICATIONS

Gordon, D., et al., "High Density Lipoprotein Cholesterol and Cardiovascular Disease", Circulation, 1989, vol. 79(1), pp. 8-15, American Heart Association.
Despres, J., et al., "HDL-Cholesterol as a Marker of Coronary Heart Disease Risk: The Quebec Cardiovascular Study", Atherosclerosis, 2000, vol. 153,(2) pp. 263-272, Elsevier.
Berge, S., et al., "Pharmaceutical Salts", J. Pharma Sci., 1977, vol. 66(1), pp. 1-19.
Wilman, D., "Prodrugs in Cancer Chemotherapy", Biochem Soc Trans, 615th Meeting, 1986, vol. 14, pp. 375-385.
Stella, et al., "Prodrugs: A Chemical Approach to Targeted Drug Delivery", Directed Drug Delivery, 1985, pp. 247-267.
Miyaura, N., et al., "Palladium-Catalyzed Cross-Coupling Reactions of Organoboron Compounds", Chemical Reviews, 1995, 95(7), pp. 2457-2483.
Jacquemard, U., et al., "Mild and Selective Deprotection of Carbamates with Bu4NF", Tetrahedron 2000, vol. 60(44), pp. 10039-10047.
Pandey, R., et al., "Synthesis of Carbamates Using Yttria-Zirconia Based Lewis Acid Catalyst", Synth Comm, 2003, 33rd Ed., No. 23, pp. 4019-4027.
Pati, H., et al., "Synthesis of N-Benzylated Anilines from the Reaction of Anilines and Benzyl Chloroformate", Synth Comm, 2004, 34th Ed., No. 5, pp. 933-940.
Seganish, W., et al., "Application of Directed Orthometalation Toward the Synthesis of Aryl Siloxanes", J. Org. Chem., 2004, vol. 69(20), pp. 6790-6795.
Shindo, K., et al., "Hydroxylation of Ionized Aromatics Including Carboxylic Acid or Amine . . . ", Tetrahedron, 2003, vol. 59(11), pp. 1895-1900.
Moraczewski, A., et al., "Using Hudrogen Bonding to Control Carbamate C-N Rotamer Equilibria", 1998, J. Org. Chem., vol. 63(21), pp. 7258-7262.
Bisgaier, C., et al., "Use of Fluorescent Cholesteryl Ester Microemulsions in Cholesteryl Ester Transfer Protein Assays", J. Lipid Res., 1993, vol. 34(9), pp. 1625-1634.
Epps, D., et al., "Method for Measuring the Activities of Cholesteryl Ester Transfer Protein (Lipid Transfer Protein)", Chem Phys Lipids, 1995, vol. 77(1), pp. 51-63.

\* cited by examiner

*Primary Examiner*—D. Margaret Seaman
(74) *Attorney, Agent, or Firm*—Nelson Mullins Riley & Scarborough, LLP

(57) ABSTRACT

The present invention provides, among other things, new bicyclic heterocyclic compounds, compositions comprising these heterocyclic compounds, methods of making the heterocyclic compounds, and methods of using these heterocyclic compounds for treating or preventing a variety of conditions or diseases associated with lipoprotein metabolism.

11 Claims, No Drawings

HETEROCYCLIC COMPOUNDS AND THEIR PHARMACEUTICAL COMPOSITIONS

RELATED APPLICATION DATA

This application claims the benefit of U.S. Provisional Patent Application Ser. No. 60/638,084, filed Dec. 20, 2004, which is incorporated herein by reference in its entirety.

FIELD OF THE INVENTION

The present invention relates to heterocyclic compounds, methods and compositions for making and using the heterocyclic compounds, and compositions and methods for treating or preventing conditions or diseases associated with lipoprotein metabolism.

BACKGROUND OF THE INVENTION

Cholesteryl ester-transfer protein (CETP) is an important player in metabolism of lipoproteins such as, for example, a high density lipoprotein (HDL). CETP is a 70 kDa plasma glycoprotein that is physically associated with HDL particles. It facilitates the transport of cholesteryl ester from HDL to apolipoprotein B-containing lipoproteins. This transfer is accompanied by transfer of triglycerides in the opposite direction. Thus, a decrease in CETP activity can result in an increase in the level of HDL cholesterol and a decrease in the level of very low density lipoprotein (VLDL) and low density lipoprotein (LDL). CETP can therefore simultaneously affect the concentrations of pro-atherogenic (for example, LDL) and anti-atherogenic (for example, HDL) lipoproteins.

Human and clinical studies have shown that inhibitors of CETP can be effective in elevating HDL levels by 30-60%. And, epidemiological studies have shown that decreased high-density lipoprotein cholesterol (HDL-C) is a powerful risk factor for coronary artery disease (CAD). Gordon et al., Circulation, 79, pp. 8-15, 1989; Despres et al., Atherosclerosis 153: 263-272, 2000. Elevating HDL-C has been shown to decrease this risk and it is estimated that each 1 mg/dl (0.02 mmol/l) elevation of HDL-C is associated with a 2-3% reduction in coronary heart disease (CHD) risk, a magnitude comparable to that for low density lipoprotein (LDL) lowering. It has been recommended that serum HDL-C levels of >40 mg/dl be considered as a therapeutic target in primary and secondary prevention. This goal appears to be particularly important in patients with low serum HDL-C levels and ischemic heart disease (IHD) or its equivalents, even if the therapeutic target for serum low-density lipoprotein cholesterol (LDL-C) levels (<100 mg/dl) has been achieved.

It is believed that the anti-atherogenic role of HDL is in part due its ability to promote the efflux of free cholesterol from cells and to transport it to the liver, a process termed reverse cholesterol transport. HDL could protect against atherosclerosis by several other mechanisms. For example, several studies showed HDL to have antioxidant and anti-inflammatory effects. Oxidative products of lipid metabolism induce inflammatory cell recruitment in vascular cells. HDL particles carry enzymes that retard LDL oxidation, including paraoxonase, platelet-activating factor acetylhydrolase, and lecithin-cholesterol acyltransferase. These enzymes degrade pro-inflammatory, oxidized phospholipids, limiting their accumulation in LDL. In addition, apoA-I can bind oxidized lipids and remove them from LDL. Further, HDL also can act as a carrier vehicle for small molecules, including bacterial lipopolysaccharide (LPS) thus regulating the inflammatory effects of LPS. In animal models of endotoxic shock, HDL attenuates organ injury and adhesion molecule expression. Thus elevating HDL is not only anti-atherogenic but it could also potentially be anti-inflammatory.

Existing therapies such as, for example, HDL-elevating therapies and anti-atherosclerosis therapies have limitations including serious toleration issues. There is a present need to find alternative therapies including methods of preventing or treating conditions or diseases associated with lipoprotein metabolism such as, for example, atherosclerosis.

SUMMARY OF THE INVENTION

The present invention is directed to novel bicyclo (or bicyclic) heterocyclic compounds, novel compositions comprising these heterocyclic compounds, and novel methods employing such bicyclo heterocycles and their compositions. Disclosed herein are methods for making bicyclo heterocyclic compounds, compositions comprising these heterocycles, and methods and compositions for using these bicyclic heterocycles. The heterocyclic compounds and compositions comprising these compounds have utility in treatment of a variety of diseases. Certain aspects of tetrahydroquinoline compounds have been disclosed in PCT Publication WO 0017164 A1, as well as in U.S. Pat. No. 6,140,343.

In one aspect, the present invention provides for compounds and compositions comprising these compounds, in which the compounds have the following formula:

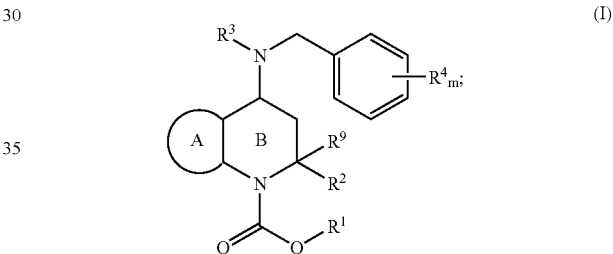

(I)

or a salt, including a pharmaceutically acceptable or a non-pharmaceutically acceptable salt, a prodrug, a diastereomeric mixture, an enantiomer, a tautomer, a racemic mixture thereof, or any combination thereof, wherein:

ring A is fused to ring B and is selected from:

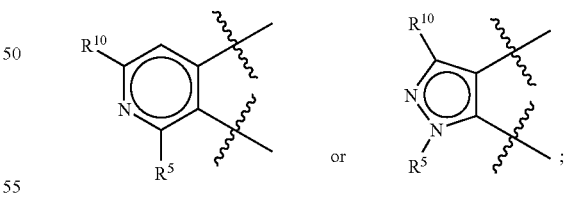

$R^1$ is an alkyl, a cycloalkyl, a haloalkyl, an aryl, an aralkyl, a heteroaryl, or a heterocyclyl, any of which having up to 12 carbon atoms; wherein any heteroaryl or heterocyclyl comprises at least one heteroatom or heterogroup selected independently from >O, >N—, >S, >NR$^6$, >SO$_2$, or >CO;

$R^2$ and $R^9$ are the same or different, and are selected independently from an alkyl, a haloalkyl, a cycloalkyl, or a cycloalkyl-substituted alkyl, any of which having up to 12 carbon atoms, or hydrogen;

$R^3$ is selected from: 1) an alkyl having up to 12 carbon atoms; 2) CO$_2$R$^6$, COR$^8$, SO$_2$R$^8$, SO$_2$NR$^6$R$^7$, or CONR$^6$R$^7$;

3) a substituted or an unsubstituted aryl, or a substituted or an unsubstituted 5-, 6-, or 7-membered heterocyclyl or heteroaryl, comprising from 1 to 4 heteroatoms or heterogroups, selected independently from >O, >N—, >S, or >NR$^6$, any of which having up to 12 carbon atoms; or 4) hydrogen or cyano;

wherein when R$^3$ is an aryl, a heterocyclyl, or a heteroaryl, R$^3$ is optionally substituted with up to three substituents selected independently from a halide, a hydroxyl, a cyano, an alkoxy having up to 12 carbon atoms, or R$^{11}$;

R$^4$, in each occurrence, is selected independently from: 1) an alkyl, a cycloalkyl, a haloalkyl, an alkoxy, an aryloxy, a haloalkoxy, an aryl, or a heteroaryl, any of which having up to 12 carbon atoms, wherein any heteroaryl comprises at least one heteroatom or heterogroup selected from >O, >N—, >S, or >NR$^6$; or 2) halogen, hydroxy, or cyano;

m is an integer selected from 0, 1, 2, or 3;

R$^5$ is selected from: 1) an alkyl, a haloalkyl, an alkoxy, a haloalkoxy, or an aryl, any of which having up to 12 carbon atoms; 2) CO$_2$R$^6$ or COR$^8$; or 3) hydrogen, cyano, or hydroxyl;

R$^6$ and R$^7$ are independently an alkyl or a haloalkyl, any of which having up to 12 carbon atoms, or hydrogen;

R$^8$ is an alkyl having up to 12 carbon atoms; and

R$^{10}$ is selected from: 1) an alkyl, a haloalkyl, an alkoxy, a haloalkoxy, or an aryl, any of which having up to 12 carbon atoms; 2) CO$_2$R$^6$ or COR$^8$; or 3) hydrogen, halogen, or cyano.

R$^{11}$ is selected independently from:

1) an alkyl, a haloalkyl, a cycloalkyl, or an alkoxycarbonyl, any of which having up to 12 carbon atoms;

2) a substituted or an unsubstituted heteroaryl or heterocyclyl, any of which having up to 12 carbon atoms, comprises at least one heteroatom or heterogroup selected independently from >O, >N—, >S, >NR$^6$, >SO$_2$, or >CO, wherein any substituted heteroaryl or heterocyclyl is substituted with up to three substituents selected independently from an alkyl having up to 12 carbon atoms or a hydroxyl; or 3) —CO-Z-R$^{13}$, —CO—R$^{12}$, —CO-Z-(CH$_2$)n-CO-Z-R$^{13}$, —NR$^{15}$R$^{16}$, -Z-CO—(CH$_2$)n-Z-R$^{13}$, -Z-CO—(CH$_2$)n-CO-Z-R$^{13}$, —O—(CH$_2$)n-CO-Z-R$^{13}$, —O—(CH$_2$)n-R$^{14}$, —O—R$^{12}$—(CH$_2$)n-R$^{13}$, —O—R$^{14}$—CO—O—R$^{13}$, —O—(CH$_2$)n-R$^{12}$, —O—(CH$_2$)n-NR'R", —O—(CH$_2$)n-CO$_2$—(CH$_2$)n-R$^{13}$, —O—(CH$_2$)n-CONR'R", —O—(CH$_2$)n-SR$^8$, —O—(CH$_2$)n-CO$_2$—R$^{13}$, —O—(CH$_2$)n-O—(CH$_2$)n-OR$^{13}$, —O—(CH$_2$)n-CONR'R", —O—(CH$_2$)n-CONH—(CH$_2$)n-OR$^{13}$, —O—(CH$_2$)n-SO$_2$R$^8$, —O—(CH$_2$)n-R$^{13}$, —O—(CH$_2$)n-OR$^{13}$, —O—(CH$_2$)n-O—(CH$_2$)n-OR$^{13}$, —S—(CH$_2$)n-CONR'R", —SO$_2$—(CH$_2$)n-OR$^{13}$, —SO$_2$—(CH$_2$)n-CONR'R", —(CH$_2$)n-O—CO—R$^8$, —(CH$_2$)n-R$^{12}$, —(CH$_2$)n-R$^{13}$, —(CH$_2$)n-N—(CH$_2$)n-OR$^{13}$, —(CH$_2$)n-CO-Z-R$^{13}$, —(CH$_2$)n-Z-R$^{13}$, or -alkenylene-CO$_2$—(CH$_2$)n-R$^{13}$;

n, in each occurrence, is independently 1, 2, or 3;

R$^{12}$, in each occurrence, is independently selected from a substituted or an unsubstituted heterocyclyl having up to 12 carbon atoms, comprising at least one heteroatom or heterogroup selected independently from >O, >N—, >S, >NR$^6$, >SO$_2$, or >CO, wherein any substituted heterocyclyl is substituted with up to three substituents selected independently from an acyl, an alkyl, or an alkoxycarbonyl, any of which having up to 12 carbon atoms, or —COOH;

R$^{13}$, in each occurrence, is independently selected from: 1) hydrogen; or 2) a cycloalkyl, an aryl, a haloalkyl, a heterocyclyl, or an alkyl group optionally substituted with at least one hydroxyl, any of which having up to 12 carbon atoms, wherein any heterocyclyl comprises at least one heteroatom or heterogroup selected independently from >O, >N—, >S, >NR$^6$, >SO$_2$, or >CO;

R$^{14}$, in each occurrence, is independently selected from a heterocyclyl, a cycloalkyl, or an aryl, any of which having up to 12 carbon atoms, wherein any heterocyclyl comprises at least one heteroatom or heterogroup selected independently from >O, >N—, >S, >NR$^6$, >SO$_2$, or >CO;

Z, in each occurrence, is independently >O or >NR$^6$;

R' and R", in each occurrence, are independently selected from hydrogen or an alkyl having up to 12 carbon artoms; and R$^{15}$ and R$^{16}$, in each occurrence, are independently selected from: 1) hydrogen; 2) an alkyl having up to 12 carbon atoms; or 3) —(CH$_2$)n-O—R$^{13}$, —(CH$_2$)n-R$^{14}$, —COR$^{13}$, —(CH$_2$)n-CO-Z-R$^{13}$, —CO$_2$R$^{13}$, —CO$_2$—(CH$_2$)n-R$^{13}$, —CO$_2$—(CH$_2$)n-R$^{12}$, —CO$_2$—(CH$_2$)n-CO-Z-R$^{13}$, —CO$_2$—(CH$_2$)n-OR$^{13}$, —CO—(CH$_2$)n-O—(CH$_2$)n-O—(CH$_2$)n-R$^{13}$, —CO—(CH$_2$)n-O(CH$_2$)n-OR$^{13}$, or —CO—NH—(CH$_2$)n-OR$^{13}$;

or R$^{15}$ and R$^{16}$ together form a substituted or an unsubstituted cyclic moiety comprising up to 12 carbon atoms, further comprising at least one additional, optional heteroatom or heterogroup selected independently from >O, >N—, >S, >NR$^6$, >SO$_2$, or >CO; wherein any substituted cyclic moiety is substituted with up to three substituents selected independently from: 1) hydroxyl; 2) an alkyl or a heteroaryl, any of which having up to 12 carbon atoms, wherein any heteroaryl comprises at least one heteroatom or heterogroup selected independently from >O, >N—, >S, or >NR$^6$; or 3) COOR$^{13}$, -Z-(CH$_2$)n-R$^{13}$, —COR$^{13}$, —CO$_2$—(CH$_2$)n-R$^{13}$, —CO(CH$_2$)n-O—R$^{13}$, —(CH$_2$)n-CO$_2$—R$^{13}$, —SO$_2$R$^8$, —SO$_2$NR'R", or —NR'R";

wherein the —(CH$_2$)n- linking moiety, in any occurrence, is optionally substituted with at least one group selected independently from hydroxyl, amino, or an alkyl having up to 3 carbon atoms.

In this aspect of the present invention, when a substituent such as R$^{12}$ in the moiety —O—R$^{12}$—(CH$_2$)n-R$^{13}$ is indicated as being situated along a chain or within a structure, the standard rules of valency are applicable, thus R$^{12}$ is a heterocyclyl-type group bonded to both an O-atom and to a —(CH$_2$)n-R$^{13}$ moiety.

In one aspect, the present invention is also directed to methods or processes for the preparation of the heterocyclic compounds disclosed herein, including compounds of the general formula (I). In another aspect, this invention is also directed to compositions comprising the heterocyclic compounds disclosed herein, including compounds of the general formula (I). When the composition is a pharmaceutical compositions, the composition also comprises a pharmaceutically acceptable carrier and at least one compound according to this invention, and further comprises optionally, a pharmaceutically acceptable auxiliary; optionally, a pharmaceutically acceptable preservative; optionally, a pharmaceutically acceptable excipient; optionally, a pharmaceutically acceptable diluent; and optionally, a pharmaceutically acceptable solvate.

The present invention also is directed to a method for treating a condition or disease in a mammalian subject, including a human. In some aspects, the method comprises administering to the subject a composition comprising a therapeutically-effective amount of at least one compound disclosed herein, or their pharmaceutically-acceptable salts thereof. Besides being useful for treating a human subject, the methods and compositions of the present invention are useful for treating a variety of mammals such as, for example, companion animals such as cats or dogs, primates, ruminant animals, and rodents.

The present invention also is directed to a method for treating or preventing a condition or disease in a human or an animal subject, the method comprising administering to the subject a composition comprising a prophylactically- or therapeutically-effective amount of at least one compound disclosed herein, or their pharmaceutically-acceptable salts thereof. In some aspects, for example, this invention provides methods for the treatment and/or prevention of conditions or disease states in a human or anminal, such as dyslipidemia, atherosclerosis, peripheral vascular disease, hypertryglyceridemia, hypercholesterolemia, hyperbetalipoproteinemia, hypoalphalipoprotenemia, cardiovascular disorders such as angina, ischemia, stroke, myocardial infarction (MI), reperfusion injury, restenosis and hypertension, and diabetic vascular diseases such as diabetic retinopathy, and endotoxemia, comprising administering a therapeutically-effective amount of at least one compound disclosed herein.

DETAILED DESCRIPTION OF THE INVENTION

In accordance with the present invention, novel bicyclic heterocyclic compounds and novel compositions comprising these heterocyclic compounds are described. In one aspect, compounds in accordance with the present invention can comprise bicyclo heterocyclic compounds, having the formula (I) as indicated above. In another aspect of this invention, compounds in accordance with the present invention can comprise bicyclo heterocyclic compounds according to formula (I), having the following formula:

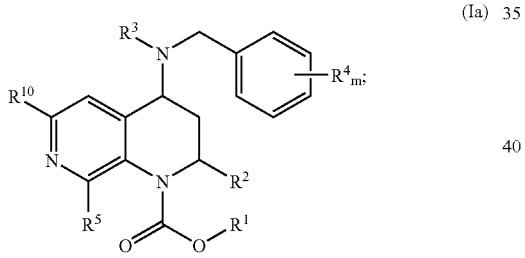

(Ia)

or a salt, including a pharmaceutically acceptable or a non-pharmaceutically acceptable salt, a prodrug, a diastereomeric mixture, an enantiomer, a tautomer, a racemic mixture thereof, or any combination thereof, wherein:

$R^1$ is an alkyl, a cycloalkyl, an aryl, an aralkyl, or a heterocyclyl, any of which having up to 12 carbon atoms; wherein the heterocyclyl comprises at least one heteroatom or heterogroup selected independently from >O, >N—, >S, >NR$^6$, >SO$_2$, or >CO;

$R^2$ is selected from an alkyl, a haloalkyl, a cycloalkyl, or a cycloalkyl-substituted alkyl, any of which having up to 12 carbon atoms, or hydrogen;

$R^3$ is selected from: 1) an alkyl having up to 12 carbon atoms; 2) CO$_2$R$^6$, COR$^8$, SO$_2$R$^8$, SO$_2$NR$^6$R$^7$, or CONR$^6$R$^7$; 3) a substituted or an unsubstituted aryl, or a substituted or an unsubstituted 5-, 6-, or 7-membered heterocyclyl or heteroaryl, comprising from 1 to 4 heteroatoms or heterogroups, selected independently from >O, >N—, >S, or >NR$^6$, any of which having up to 12 carbon atoms; or 4) hydrogen or cyano;

wherein when $R^3$ is an aryl, a heterocyclyl, or a heteroaryl, $R^3$ is optionally substituted with up to three substituents selected independently from a halide, a hydroxyl, a cyano, an alkoxy having up to 12 carbon atoms, or R$^{11}$;

$R^4$, in each occurrence, is selected independently from: 1) an alkyl, a cycloalkyl, a haloalkyl, an alkoxy, an aryloxy, a haloalkoxy, an aryl, or a heteroaryl, any of which having up to 12 carbon atoms, wherein any heteroaryl comprises at least one heteroatom or heterogroup selected from >O, >N—, >S, or >NR$^6$; or 2) halogen, hydroxy, or cyano;

m is an integer selected from 0, 1, 2, or 3;

$R^5$ is selected from: 1) an alkyl, a haloalkyl, an alkoxy, a haloalkoxy, or an aryl, any of which having up to 12 carbon atoms; 2) CO$_2$R$^6$ or COR$^8$; or 3) hydrogen, cyano, or hydroxyl;

$R^6$ and $R^7$ are independently an alkyl or a haloalkyl, any of which having up to 12 carbon atoms, or hydrogen;

$R^8$ is an alkyl having up to 12 carbon atoms; and $R^{10}$ is selected from: 1) an alkyl, a haloalkyl, an alkoxy, a haloalkoxy, or an aryl, any of which having up to 12 carbon atoms; 2) CO$_2$R$^6$ or COR$^8$; or 3) hydrogen, halogen, or cyano.

$R^{11}$ is selected independently from:
1) an alkyl, a haloalkyl, a cycloalkyl, or an alkoxycarbonyl, any of which having up to 12 carbon atoms;
2) a substituted or an unsubstituted heteroaryl or heterocyclyl, any of which having up to 12 carbon atoms, comprises at least one heteroatom or heterogroup selected independently from >O, >N—, >S, >NR$^6$, >SO$_2$, or >CO, wherein any substituted heteroaryl or heterocyclyl is substituted with up to three substituents selected independently from an alkyl having up to 12 carbon atoms or a hydroxyl; or
3) —CO-Z-R$^{13}$, —CO—R$^{12}$, —CO-Z-(CH$_2$)n-CO-Z-R$^{13}$, —NR$^{15}$R$^{16}$, -Z-CO—(CH$_2$)n-Z-R$^{13}$, -Z-CO—(CH$_2$)n-CO-Z-R$^{13}$, —O—(CH$_2$)n-CO-Z-R$^{13}$, —O—(CH$_2$)n-R$^{14}$, —O—R$^{12}$—(CH$_2$)n-R$^{13}$, —O—R$^{14}$—CO—O—R$^{13}$, —O—(CH$_2$)n-R$^{12}$, —O—(CH$_2$)n-NR'R", —O—(CH$_2$)n-CO$_2$—(CH$_2$)n-R$^3$, —O—(CH$_2$)n-CONR'R", —O—(CH$_2$)n-SR$^8$, —O—(CH$_2$)n-CO$_2$—R$^{13}$, —O—(CH$_2$)n-O—(CH$_2$)n-OR$^{13}$, —O—(CH$_2$)n-CONR'R", —O—(CH$_2$)n-CONH—(CH$_2$)n-OR$^{13}$, —O—(CH$_2$)n-SO$_2$R$^8$, —O—(CH$_2$)n-R$^{13}$, —O—(CH$_2$)n-OR$^{13}$, —O—(CH$_2$)n-O—(CH$_2$)n-OR$^{13}$, —S—(CH$_2$)n-CONR'R", —SO$_2$—(CH$_2$)n-OR$^{13}$, —SO$_2$—(CH$_2$)n-CONR'R", —(CH$_2$)n-O—CO—R$^8$, —(CH$_2$)n-R$^{12}$, —(CH$_2$)n-R$^{13}$, —(CH$_2$)n-N—(CH$_2$)n-OR$^{13}$, —(CH$_2$)n-CO-Z-R$^{13}$, —(CH$_2$)n-Z-R$^{13}$, or -alkenylene-CO$_2$—(CH$_2$)n-R$^{13}$;

n, in each occurrence, is independently 1, 2, or 3;

$R^{12}$, in each occurrence, is independently selected from a substituted or an unsubstituted heterocyclyl having up to 12 carbon atoms, comprising at least one heteroatom or heterogroup selected independently from >O, >N—, >S, >NR$^6$, >SO$_2$, or >CO, wherein any substituted heterocyclyl is substituted with up to three substituents selected independently from an acyl, an alkyl, or an alkoxycarbonyl, any of which having up to 12 carbon atoms, or —COOH;

$R^{13}$, in each occurrence, is independently selected from: 1) hydrogen; or 2) a cycloalkyl, an aryl, a haloalkyl, a heterocyclyl, or an alkyl group optionally substituted with at least one hydroxyl, any of which having up to 12 carbon atoms, wherein any heterocyclyl comprises at least one heteroatom or heterogroup selected independently from >O, >N—, >S, >NR$^6$, >SO$_2$, or >CO;

$R^{14}$, in each occurrence, is independently selected from a heterocyclyl, a cycloalkyl, or an aryl, any of which having up to 12 carbon atoms, wherein any heterocyclyl comprises at least one heteroatom or heterogroup selected independently from >O, >N—, >S, >NR$^6$, >SO$_2$, or >CO;

Z, in each occurrence, is independently >O or >$NR^6$;

R' and R", in each occurrence, are independently selected from hydrogen or an alkyl having up to 12 carbon atoms; and $R^{15}$ and $R^{16}$, in each occurrence, are independently selected from: 1) hydrogen; 2) an alkyl having up to 12 carbon atoms; or 3) —$(CH_2)$n-O—$R^{13}$, —$(CH_2)$n-$R^{14}$, —$COR^{13}$, —$(CH_2)$n-CO-Z-$R^{13}$, —$CO_2R^{13}$, —$CO_2$—$(CH_2)$n-$R^{13}$, —$CO_2$—$(CH_2)$n-$R^{12}$, —$CO_2$—$(CH_2)$n-CO-Z-$R^{13}$, —$CO_2$—$(CH_2)$n-$OR^{13}$, —CO—$(CH_2)$n-O—$(CH_2)$n-O—$(CH_2)$n-$R^{13}$, —CO—$(CH_2)$n-O$(CH_2)$n-$OR^{13}$, or —CO—NH—$(CH_2)$n-$OR^{13}$;

or $R^{15}$ and $R^{16}$ together form a substituted or an unsubstituted cyclic moiety comprising up to 12 carbon atoms, further comprising at least one additional, optional heteroatom or heterogroup selected independently from >O, >N—, >S, >$NR^6$, >$SO_2$, or >CO; wherein any substituted cyclic moiety is substituted with up to three substituents selected independently from: 1) hydroxyl; 2) an alkyl or a heteroaryl, any of which having up to 12 carbon atoms, wherein any heteroaryl comprises at least one heteroatom or heterogroup selected independently from >O, >N—, >S, or >$NR^6$; or 3) $COOR^{13}$, -Z-$(CH_2)$n-$R^{13}$, —$COR^{13}$, —$CO_2$—$(CH_2)$n-$R^{13}$, —CO$(CH_2)$n-O—$R^{13}$, —$(CH_2)$n-$CO_2$—$R^{13}$, —$SO_2R^8$, —$SO_2NR'R''$, or —NR'R";

wherein the —$(CH_2)$n- linking moiety, in any occurrence, is optionally substituted with at least one group selected independently from hydroxyl, amino, or an alkyl having up to 3 carbon atoms.

In a further aspect of this invention the following substituents of the formula (Ia) can be selected as specified here, while unspecified substituents are selected as above:

$R^1$ is an alkyl having up to 6 carbon atoms;

$R^2$ is ethyl;

$R^3$ is selected from: 1) $CO_2R^6$; 2) a substituted or an unsubstituted tetrazolyl, 1,2,4-oxadiazolyl, 1,3,4-oxadiazolyl, oxazolyl, or isooxazolyl, wherein any substituent is selected independently from an alkyl having up to 6 carbon atoms, an alkoxycarbonyl having up to 6 carbon atoms, or a haloalkyl having 1 or 2 carbon atoms; or 3) cyano;

wherein $R^3$ is optionally substituted with up to three substituents selected independently from a halide, a hydroxyl, a cyano, an alkoxy having up to 12 carbon atoms, or $R^{11}$;

$R^4$, in each occurrence, is selected independently from a halogen, $CF_3$, CN, methyl, or $OCF_3$;

m is 1 or 2;

$R^5$ is selected from: 1) an alkyl, a haloalkyl, an alkoxy, or a haloalkoxy, any of which having 1 or 2 carbon atoms; or 2) hydrogen;

$R^6$ is an alkyl having 1 or 2 carbon atoms; and $R^{10}$ is selected from: 1) an alkyl, a haloalkyl, an alkoxy, or a haloalkoxy, any of which having 1 or 2 carbon atoms; or 2) hydrogen;

$R^{11}$ is selected independently from:

1) an alkyl, a haloalkyl, a cycloalkyl, or an alkoxycarbonyl, any of which having up to 12 carbon atoms;

2) a substituted or an unsubstituted heteroaryl or heterocyclyl, any of which having up to 12 carbon atoms, comprises at least one heteroatom or heterogroup selected independently from >O, >N—, >S, >$NR^6$, >$SO_2$, or >CO, wherein any substituted heteroaryl or heterocyclyl is substituted with up to three substituents selected independently from an alkyl having up to 12 carbon atoms or a hydroxyl; or 3) —CO-Z-$R^{13}$, —CO—$R^{12}$, —CO-Z-$(CH_2)$n-CO-Z-$R^{13}$, —$NR^{15}R^{16}$, -Z-CO—$(CH_2)$n-Z-$R^{13}$, -Z-CO—$(CH_2)$n-CO-Z-$R^{13}$, —O—$(CH_2)$n-CO-Z-$R^{13}$, —O—$(CH_2)$n-$R^{14}$, —O—$R^{12}$—$(CH_2)$n-$R^{13}$, —O—$R^{14}$—CO—O—$R^{13}$, —O—$(CH_2)$n-$R^{12}$, —O—$(CH_2)$n-NR'R", —O—$(CH_2)$n-$CO_2$—$(CH_2)$n-$R^{13}$, —O—$(CH_2)$n-CONR'R", —O—$(CH_2)$n-$SR^8$, —O—$(CH_2)$n-$CO_2$—$R^{13}$, —O—$(CH_2)$n-O—$(CH_2)$n-$OR^{13}$, —O—$(CH_2)$n-CONR'R", —O—$(CH_2)$n-CONH—$(CH_2)$n-$OR^{13}$, —O—$(CH_2)$n-$SO_2R^8$, —O—$(CH_2)$n-$R^{13}$, —O—$(CH_2)$n-$OR^{13}$, —O—$(CH_2)$n-O—$(CH_2)$n-$OR^{13}$, —S—$(CH_2)$n-CONR'R", —$SO_2$—$(CH_2)$n-$OR^{13}$, —$SO_2$—$(CH_2)$n-CONR'R", —$(CH_2)$n-O—CO—$R^8$, —$(CH_2)$n-$R^{12}$, —$(CH_2)$n-$R^{13}$, —$(CH_2)$n-N—$(CH_2)$n-$OR^{13}$, —$(CH_2)$n-CO-Z-$R^{13}$, —$(CH_2)$n-Z-$R^{13}$, or -alkenylene-$CO_2$—$(CH_2)$n-$R^{13}$;

n, in each occurrence, is independently 1, 2, or 3;

$R^{12}$, in each occurrence, is independently selected from a substituted or an unsubstituted heterocyclyl having up to 12 carbon atoms, comprising at least one heteroatom or heterogroup selected independently from >O, >N—, >S, >$NR^6$, >$SO_2$, or >CO, wherein any substituted heterocyclyl is substituted with up to three substituents selected independently from an acyl, an alkyl, or an alkoxycarbonyl, any of which having up to 12 carbon atoms, or —COOH;

$R^{13}$, in each occurrence, is independently selected from: 1) hydrogen; or 2) a cycloalkyl, an aryl, a haloalkyl, a heterocyclyl, or an alkyl group optionally substituted with at least one hydroxyl, any of which having up to 12 carbon atoms, wherein any heterocyclyl comprises at least one heteroatom or heterogroup selected independently from >O, >N—, >S, >$NR^6$, >$SO_2$, or >CO;

$R^{14}$, in each occurrence, is independently selected from a heterocyclyl, a cycloalkyl, or an aryl, any of which having up to 12 carbon atoms, wherein any heterocyclyl comprises at least one heteroatom or heterogroup selected independently from >O, >N—, >S, >$NR^6$, >$SO_2$, or >CO;

Z, in each occurrence, is independently >O or >$NR^6$;

R' and R", in each occurrence, are independently selected from hydrogen or an alkyl having up to 12 carbon artoms; and $R^{15}$ and $R^{16}$, in each occurrence, are independently selected from: 1) hydrogen; 2) an alkyl having up to 12 carbon atoms; or 3) —$(CH_2)$n-O—$R^{13}$, —$(CH_2)$n-$R^{14}$, —$COR^{13}$, —$(CH_2)$n-CO-Z-$R^{13}$, —$CO_2R^{13}$, —$CO_2$—$(CH_2)$n-$R^{13}$, —$CO_2$—$(CH_2)$n-$R^{12}$, —$CO_2$—$(CH_2)$n-CO-Z-$R^{13}$, —$CO_2$—$(CH_2)$n-$OR^{13}$, —CO—$(CH_2)$n-O—$(CH_2)$n-O—$(CH_2)$n-$R^{13}$, —CO—$(CH_2)$n-O$(CH_2)$n-$OR^{13}$, or —CO—NH—$(CH_2)$n-$OR^{13}$;

or $R^{15}$ and $R^{16}$ together form a substituted or an unsubstituted cyclic moiety comprising up to 12 carbon atoms, further comprising at least one additional, optional heteroatom or heterogroup selected independently from >O, >N—, >S, >$NR^6$, >$SO_2$, or >CO; wherein any substituted cyclic moiety is substituted with up to three substituents selected independently from: 1) hydroxyl; 2) an alkyl or a heteroaryl, any of which having up to 12 carbon atoms, wherein any heteroaryl comprises at least one heteroatom or heterogroup selected independently from >O, >N—, >S, or >$NR^6$; or 3) $COOR^{13}$, -Z-$(CH_2)$n-$R^{13}$, —$COR^{13}$, —$CO_2$—$(CH_2)$n-$R^{13}$, —CO$(CH_2)$n-O—$R^{13}$, —$(CH_2)$n-$CO_2$—$R^{13}$, —$SO_2R^8$, —$SO_2NR'R''$, or —NR'R";

wherein the —$(CH_2)$n- linking moiety, in any occurrence, is optionally substituted with at least one group selected independently from hydroxyl, amino, or an alkyl having up to 3 carbon atoms.

Still another aspect of this invention provides bicyclo heterocyclic compounds according to formula (I), having the following formula:

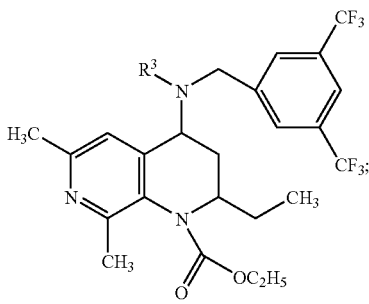

(Ia1)

or a salt, including a pharmaceutically acceptable or a non-pharmaceutically acceptable salt, a prodrug, a diastereomeric mixture, an enantiomer, a tautomer, a racemic mixture thereof, or any combination thereof, wherein:

R³ is selected from a substituted or an unsubstituted tetrazolyl, 1,2,4-oxadiazolyl, 1,3,4-oxadiazolyl, oxazolyl, isooxazolyl, alkoxycarbonyl, pyrimidinyl, pyridyl, or thiazolyl; wherein any substituent is selected independently from CF₃, methyl, ethyl, ethoxycarbonyl, or tert-butoxycarbonyl.

In still a further aspect of the present invention, this disclosure provides heterocyclic compounds, wherein the compound is selected from any of the compounds in the following table, including any combination thereof. By the disclosure of these specific compounds, it is intended to include any salt, including a pharmaceutically acceptable or a non-pharmaceutically acceptable salt, any prodrug, and any stereoisomer, including diastereomeric mixtures, enantiomers, tautomers, racemic mixtures, or any combinations thereof, of the disclosed compounds.

TABLE 1

Representative examples of compounds in accordance with this disclosure, having the following general formulas.

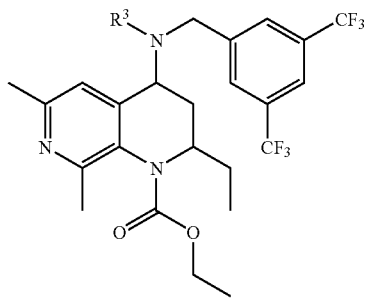

| Entry | Compound | R³ |
|---|---|---|
| 1. | 4-[(3,5-Bis-trifluoromethyl-benzyl)-(1H-tetrazol-5-yl)-amino]-2-ethyl-6,8-dimethyl-3,4-dihydro-2H-[1,7]naphthyridine-1-carboxylic acid ethylester | |
| 2. | 4-[(3,5-Bis-trifluoromethyl-benzyl)-(2-methyl-2H-tetrazol-5-yl)-amino]-2-ethyl-6,8-dimethyl-3,4-dihydro-2H-[1,7]naphthyridine-1-carboxylic acid ethyl ester | |
| 3. | 4-[(3,5-Bis-trifluoromethyl-benzyl)-(1-methyl-1H-tetrazol-5-yl)-amino]-2-ethyl-6,8-dimethyl-3,4-dihydro-2H-[1,7]naphthyridine-1-carboxylic acid ethyl ester | |
| 4. | 4-[(3,5-Bis-trifluoromethyl-benzyl)-(5-methyl-[1,3,4]oxadiazol-2-yl)-amino]-2-ethyl-6,8-dimethyl-3,4-dihydro-2H-[1,7]naphthyridine-1-carboxylic acid ethyl ester | |

TABLE 1-continued

Representative examples of compounds in accordance with this disclosure, having the following general formulas.

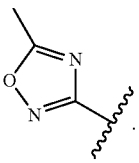

| Entry | Compound | R³ |
|---|---|---|
| 5. | 4-[(3,5-Bis-trifluoromethyl-benzyl)-(5-methyl-[1,2,4]oxadiazol-3-yl)-amino]-2-ethyl-6,8-dimethyl-3,4-dihydro-2H-[1,7]naphthyridme-1-carboxylic acid ethyl ester | 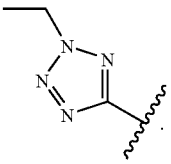 |
| 6. | 4-[(3,5-Bis-trifluoromethyl-benzyl)-(2-ethyl-2H-tetrazol-5-yl)-amino]-2-ethyl-6,8-dimethyl-3,4-dihydro-2H-[1,7]naphthyridine-1-carboxylic acid ethyl ester | 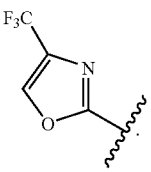 |
| 7. | 4-[(3,5-Bis-trifluoromethyl-benzyl)-(4-trifluoromethyl-oxazol-2-yl)-amino]-2-ethyl-6,8-dimethyl-3,4-dihydro-2H-[1,7]naphthyridine-1-carboxylic acid ethyl ester | 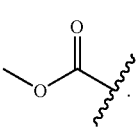 |
| 8. | 4-[(3,5-Bis-trifluoromethyl-benzyl)-methoxycarbonyl-amino]-2-ethyl-6,8-dimethyl-3,4-dihydro-2H-[1,7]naphthyridine-1-carboxylic acid ethyl ester | 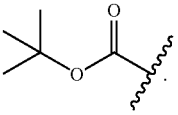 |
| 9. | 4-[(3,5-Bis-trifluoromethyl-benzyl)-tert-butoxycarbonyl-amino]-2-ethyl-6,8-dimethyl-3,4-dihydro-2H-[1,7]naphthyridine-1-carboxylic acid ethyl ester | 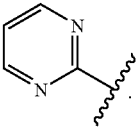 |
| 10. | 4-[(3,5-Bis-trifluoromethyl-benzyl)-pyrimidin-2-yl-amino]-2-ethyl-6,8-dimethyl-3,4-dihydro-2H-[1,7]naphthyridine-1-carboxylic acid ethyl ester | 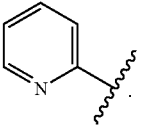 |
| 11. | 4-[(3,5-Bis-trifluoromethyl-benzyl)-pyridin-2-yl-amino]-2-ethyl-6,8-dimethyl-3,4-dihydro-2H-[1,7]naphthyridine-1-carboxylic acid ethyl ester | |

TABLE 1-continued

Representative examples of compounds in accordance with this disclosure, having the following general formulas.

| Entry | Compound | R³ |
|---|---|---|
| 12. | 4-[(3,5-Bis-trifluoromethyl-benzyl)-(4-methyl-oxazol-2-yl)-amino]-2-ethyl-6,8-dimethyl-3,4-dihydro-2H-[1,7]naphthyridine-1-carboxylic acid ethyl ester | 4-methyl-oxazol-2-yl |
| 13. | 4-[(3,5-Bis-trifluoromethyl-benzyl)-(4-methyl-thiazol-2-yl)-amino]-2-ethyl-6,8-dimethyl-3,4-dihydro-2H-[1,7]naphthyridine-1-carboxylic acid ethyl ester | 4-methyl-thiazol-2-yl |
| 14. | 4-[(3,5-Bis-trifluoromethyl-benzyl)-(5-methyl-isoxazol-3-yl)-amino]-2-ethyl-6,8-dimethyl-3,4-dihydro-2H-[1,7]naphthyridine-1-carboxylicacid ethyl ester | 5-methyl-isoxazol-3-yl |
| 15. | 4-[(3,5-Bis-trifluoromethyl-benzyl)-(4-ethoxycarbonyl-oxazol-2-yl)-amino]-2-ethyl-6,8-dimethyl-3,4-dihydro-2H-[1,7]naphthyridine-1-carboxylic acid ethyl ester | 4-ethoxycarbonyl-oxazol-2-yl |
| 16. | 4-[[5-(4-Acetyl-piperazin-1-yl)-pyrimidin-2-yl]-(3,5-bis-trifluoromethyl-benzyl)-amino]-2-ethyl-6,8-dimethyl-3,4-dihydro-2H-[1,7]naphthyridme-1-carboxylic acid ethyl ester | 5-(4-acetyl-piperazin-1-yl)-pyrimidin-2-yl |
| 17. | 4-{(3,5-Bis-trifluoromethyl-benzyl)-[5-(2-methoxy-acetylamino)-pyrimidin-2-yl]-amino}-2-ethyl-6,8-dimethyl-3,4-dihydro-2H-[1,7]naphthyridine-1-carboxylic acid ethyl ester | 5-(2-methoxy-acetylamino)-pyrazin-2-yl |

TABLE 1-continued

Representative examples of compounds in accordance with this disclosure, having the following general formulas.

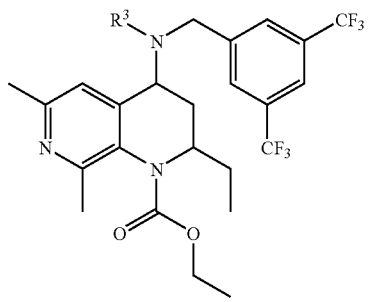

| Entry | Compound | R³ |
|---|---|---|
| 18. | 4-{(3,5-Bis-trifluoromethyl-benzyl)-[5-(2-morpholin-4-yl-ethoxy)-pyrimidin-2-yl]-amino}-2-ethyl-6,8-dimethyl-3,4-dihydro-2H-[1,7]naphthyridine-1-carboxylic acid ethyl ester | |
| 19. | 4-[(3,5-Bis-trifluoromethyl-benzyl)-(5-morpholin-4-yl-pyrimidin-2-yl)-amino]-2-ethyl-6,8-dimethyl-3,4-dihydro-2H-[1,7]naphthyridine-1-carboxylic acid ethyl ester | |
| 20. | 4-[(3,5-Bis-trifluoromethyl-benzyl)-(5-morpholin-4-yl-pyridin-2-yl)-amino]-2-ethyl-6,8-dimethyl-3,4-dihydro-2H-[1,7]naphthyridine-1-carboxylic acid ethyl ester | |
| 21. | 4-{(3,5-Bis-trifluoromethyl-benzyl)-(5-(2H-tetrazol-5-yl)-pyridin-2-yl]-amino}-2-ethyl-6,8-dimethyl-3,4-dihydro-2H-[1,7]naphthyridine-1-carboxylic acid ethyl ester | |
| 22. | 4-{(3,5-Bis-trifluoromethyl-benzyl)-[5-(pyrrolidine-1-carbonyl)-pyrimidin-2-yl]-amino}-2-ethyl-6,8-dimethyl-3,4-dihydro-2H-[1,7]naphthyridine-1-carboxylic acid ethyl ester | |

TABLE 1-continued

Representative examples of compounds in accordance with this disclosure, having the following general formulas.

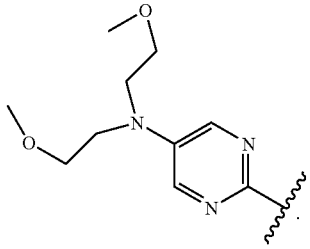

| Entry | Compound | R³ |
|---|---|---|
| 23. | 4-[{5-[Bis-(2-methoxy-ethyl)-amino]-pyrimidin-2-yl}-(3,5-bis-trifluoromethyl-benzyl)-amino]-2-ethyl-6,8-dimethyl-3,4-dihydro-2H-[1,7]naphthyridine-1-carboxylic acid ethyl ester | 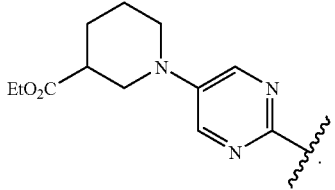 |
| 24. | 4-{(3,5-Bis-trifluoromethyl-benzyl)-[5-(3-ethoxycarbonyl-pipendin-1-yl)-pyrimidin-2-yl]-amino}-2-ethyl-6,8-dimethyl-3,4-dihydro-2H-[1,7]naphthyridine-1-carboxylic acid ethyl ester | 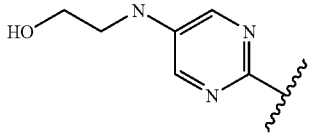 |
| 25. | 4-{(3,5-Bis-trifluoromethyl-benzyl)-[5-(2-hydroxy-ethylamino)-pyrimidin-2-yl]-amino}-2-ethyl-6,8-dimethyl-3,4-dihydro-2H-[1,7]naphthyridine-1-carboxylic acid ethyl ester | 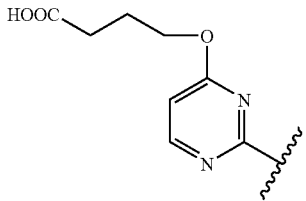 |
| 26. | 4-{(3,5-Bis-trifluoromethyl-benzyl)-[4-(3-carboxy-propoxy)-pyrimidin-2-yl]-amino}-2-ethyl-6,8-dimethyl-3,4-dihydro-2H-[1,7]naphthyndine-1-carboxylic acid ethyl ester | 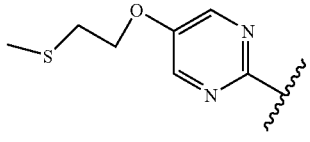 |
| 27. | 4-{(3,5-Bis-trifluoromethyl-benzyl)-[5-(2-methylsulfanyl-ethoxy)-pyrimidin-2-yl]-amino }-2-ethyl-6,8-dimethyl-3,4-dihydro-2H-[1,7]naphthyridine-1-carboxylic acid ethyl ester | 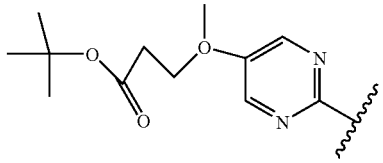 |
| 28. | 4-((3,5-Bis-trifluoromethyl-benzyl)-{5-[(2-tert-butoxycarbonyl-ethyl)-methyl-amino]-pyrimidin-2-yl}-amino)-2-ethyl-6,8-dimethyl-3,4-dihydro-2H-[1,7]naphthyridine-1-carboxylic acid ethyl ester | |

TABLE 1-continued

Representative examples of compounds in accordance with this disclosure, having the following general formulas.

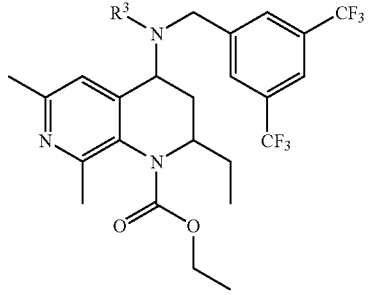

| Entry | Compound | R³ |
|---|---|---|
| 29. | 4-{(3,5-Bis-trifluoromethyl-benzyl)-[5-(2-carboxy-ethyl)-pyrimidin-2-yl]-amino}-2-ethyl-6,8-dimethyl-3,4-dihydro-2H-[1,7]naphthyridine-1-carboxylic acid ethyl ester | 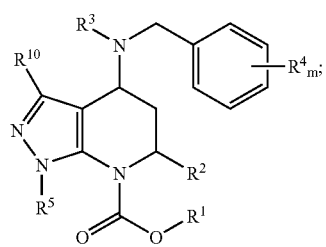 |

In yet another aspect, the present invention provides compounds according to formula (I), and compositions comprising these compounds, wherein the compounds have the following formula:

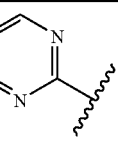

(Ib)

or a salt, including a pharmaceutically acceptable or a non-pharmaceutically acceptable salt, a prodrug, a diastereomeric mixture, an enantiomer, a tautomer, a racemic mixture thereof, or any combination thereof, wherein:

$R^1$ is an alkyl, a cycloalkyl, an aryl, an aralkyl, or a heterocyclyl, any of which having up to 12 carbon atoms; wherein the heterocyclyl comprises at least one heteroatom or heterogroup selected independently from >O, >N—, >S, >NR⁶, >SO₂, or >CO;

$R^2$ is selected from an alkyl, a haloalkyl, a cycloalkyl, or a cycloalkyl-substituted alkyl, any of which having up to 12 carbon atoms, or hydrogen;

$R^3$ is selected from: 1) an alkyl having up to 12 carbon atoms; 2) CO₂R⁶, COR⁸, SO₂R⁸, SO₂NR⁶R⁷, or CONR⁶R⁷; 3) a substituted or an unsubstituted aryl, or a substituted or an unsubstituted 5-, 6-, or 7-membered heterocyclyl or heteroaryl, comprising from 1 to 4 heteroatoms or heterogroups, selected independently from >O, >N—, >S, or >NR⁶, any of which having up to 12 carbon atoms; or 4) hydrogen or cyano;

wherein when $R^3$ is an aryl, a heterocyclyl, or a heteroaryl, $R^3$ is optionally substituted with up to three substituents selected independently from a halide, a hydroxyl, a cyano, an alkoxy having up to 12 carbon atoms, or $R^{11}$;

$R^4$, in each occurrence, is selected independently from: 1) an alkyl, a cycloalkyl, a haloalkyl, an alkoxy, an aryloxy, a haloalkoxy, an aryl, or a heteroaryl, any of which having up to 12 carbon atoms, wherein any heteroaryl comprises at least one heteroatom or heterogroup selected from >O, >N—, >S, or >NR⁶; or 2) halogen, hydroxy, or cyano;

m is an integer selected from 0, 1, 2, or 3;

$R^5$ is selected from: 1) an alkyl, a haloalkyl, an alkoxy, a haloalkoxy, or an aryl, any of which having up to 12 carbon atoms; or 2) hydrogen or hydroxyl;

$R^6$ and $R^7$ are independently an alkyl or a haloalkyl, any of which having up to 12 carbon atoms, or hydrogen;

$R^8$ is an alkyl having up to 12 carbon atoms; and $R^{10}$ is selected from: 1) an alkyl, a haloalkyl, an alkoxy, a haloalkoxy, or an aryl, any of which having up to 12 carbon atoms; or 2) hydrogen, halogen, or cyano;

$R^{11}$ is selected independently from:

1) an alkyl, a haloalkyl, a cycloalkyl, or an alkoxycarbonyl, any of which having up to 12 carbon atoms;

2) a substituted or an unsubstituted heteroaryl or heterocyclyl, any of which having up to 12 carbon atoms, comprises at least one heteroatom or heterogroup selected independently from >O, >N—, >S, >NR⁶, >SO₂, or >CO, wherein any substituted heteroaryl or heterocyclyl is substituted with up to three substituents selected independently from an alkyl having up to 12 carbon atoms or a hydroxyl; or 3) —CO-Z-R¹³, —CO—R¹², —CO-Z-(CH₂)n-CO-Z-R¹³, —NR¹⁵R¹⁶, -Z-CO—(CH₂)n-Z-R¹³, -Z-CO—(CH₂)n-CO-Z-R¹³, —O—(CH₂)n-CO-Z-R¹³, —O—(CH₂)n-R¹⁴, —O—R¹²—(CH₂)n-R¹³, —O—R¹⁴—CO—O—R¹³, —O—(CH₂)n-R¹², —O—(CH₂)n-NR'R", —O—(CH₂)n-CO₂—(CH₂)n-R¹³, —O—(CH₂)n-CONR'R", —O—(CH₂)n-SR⁸, —O—(CH₂)n-CO₂—R¹³, —O—(CH₂)n-O—(CH₂)n-OR¹³, —O—(CH₂)n-CONR'R", —O—(CH₂)n-CONH—(CH₂)n-OR¹³, —O—(CH₂)n-SO₂R⁸, —O—(CH₂)n-R¹³, —O—(CH₂)n-OR¹³, —O—(CH₂)n-O—(CH₂)n-OR¹³, —S—(CH₂)n-CONR'R", —SO₂—(CH₂)n-OR¹³, —SO₂—(CH₂)n-CONR'R", —(CH₂)n-O—CO—R⁸, —(CH₂)n-R¹², —(CH₂)n-R¹³, —(CH₂)n-N—(CH₂)n-OR¹³, —(CH₂)n-CO-Z-R¹³, —(CH₂)n-Z-R¹³, or -alkenylene-CO₂—(CH₂)n-R¹³;

n, in each occurrence, is independently 1, 2, or 3;

R¹², in each occurrence, is independently selected from a substituted or an unsubstituted heterocyclyl having up to 12 carbon atoms, comprising at least one heteroatom or heterogroup selected independently from >O, >N—, >S, >NR⁶, >SO₂, or >CO, wherein any substituted heterocyclyl is substituted with up to three substituents selected independently from an acyl, an alkyl, or an alkoxycarbonyl, any of which having up to 12 carbon atoms, or —COOH;

R¹³, in each occurrence, is independently selected from: 1) hydrogen; or 2) a cycloalkyl, an aryl, a haloalkyl, a heterocyclyl, or an alkyl group optionally substituted with at least one hydroxyl, any of which having up to 12 carbon atoms, wherein any heterocyclyl comprises at least one heteroatom or heterogroup selected independently from >O, >N—, >S, >NR⁶, >SO₂, or >CO;

R¹⁴, in each occurrence, is independently selected from a heterocyclyl, a cycloalkyl, or an aryl, any of which having up to 12 carbon atoms, wherein any heterocyclyl comprises at least one heteroatom or heterogroup selected independently from >O, >N—, >S, >NR⁶, >SO₂, or >CO;

Z, in each occurrence, is independently >O or >NR⁶;

R' and R", in each occurrence, are independently selected from hydrogen or an alkyl having up to 12 carbon artoms; and R¹⁵ and R¹⁶, in each occurrence, are independently selected from: 1) hydrogen; 2) an alkyl having up to 12 carbon atoms; or 3) —(CH₂)n-O—R¹³, —(CH₂)n-R¹⁴, —COR¹³, —(CH₂)n-CO-Z-R¹³, —CO₂R¹³, —CO₂—(CH₂)n-R¹³, —CO₂—(CH₂)n-R¹², —CO₂—(CH₂)n-CO-Z-R¹³, —CO₂—(CH₂)n-OR¹³, —CO—(CH₂)n-O—(CH₂)n-O—(CH₂)n-R¹³, —CO—(CH₂)n-O(CH₂)n-OR¹³, or —CO—NH—(CH₂)n-OR¹³;

or R¹⁵ and R¹⁶ together form a substituted or an unsubstituted cyclic moiety comprising up to 12 carbon atoms, further comprising at least one additional, optional heteroatom or heterogroup selected independently from >O, >N—, >S, >NR⁶, >SO₂, or >CO; wherein any substituted cyclic moiety is substituted with up to three substituents selected independently from: 1) hydroxyl; 2) an alkyl or a heteroaryl, any of which having up to 12 carbon atoms, wherein any heteroaryl comprises at least one heteroatom or heterogroup selected independently from >O, >N—, >S, or >NR⁶; or 3) COOR¹³, -Z-(CH₂)n-R¹³, —COR¹³, —CO₂—(CH₂)n-R¹³, —CO(CH₂)n-O—R¹³, —(CH₂)n-CO₂—R¹³, —SO₂R⁸, —SO₂NR'R", or —NR'R";

wherein the —(CH₂)n- linking moiety, in any occurrence, is optionally substituted with at least one group selected independently from hydroxyl, amino, or an alkyl having up to 3 carbon atoms.

In a further aspect of this invention the following substituents of the formula (Ib) above can be selected as specified here, while unspecified substitutents are selected as above. In this aspect, R¹ is an alkyl having up to 6 carbon atoms;
R² is ethyl;

R³ is selected from: 1) CO₂R⁶; 2) a substituted or an unsubstituted tetrazolyl, 1,2,4-oxadiazolyl, 1,3,4-oxadiazolyl, oxazolyl, or isooxazolyl, wherein any substituent is selected independently from an alkyl having up to 6 carbon atoms, an alkoxycarbonyl having up to 6 carbon atoms, or a haloalkyl having 1 or 2 carbon atoms; or 3) cyano;

R⁴, in each occurrence, is selected independently from a halogen, CF₃, CN, methyl, or OCF₃;

m is 1 or 2;

R⁵ is selected from: 1) an alkyl, a haloalkyl, an alkoxy, or a haloalkoxy, any of which having 1 or 2 carbon atoms; or 2) hydrogen;

R⁶ is an alkyl having 1 or 2 carbon atoms; and

R¹⁰ is selected from: 1) an alkyl, a haloalkyl, an alkoxy, or a haloalkoxy, any of which having 1 or 2 carbon atoms; or 2) hydrogen.

In still a further aspect, the present disclosure provides compounds according to formula (I), and compositions comprising these compounds, wherein the compounds have the following formula:

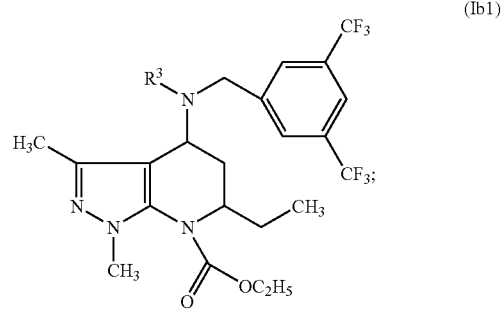

(Ib1)

or a salt, including a pharmaceutically acceptable or a non-pharmaceutically acceptable salt, a prodrug, a diastereomeric mixture, an enantiomer, a tautomer, a racemic mixture thereof, or any combination thereof, wherein:

R³ is selected from a substituted or an unsubstituted tetrazolyl, 1,2,4-oxadiazolyl, 1,3,4-oxadiazolyl, oxazolyl, isooxazolyl, alkoxycarbonyl, pyrimidinyl, pyridyl, or thiazolyl; wherein any substituent is selected independently from CF₃, methyl, ethyl, ethoxycarbonyl, or tert-butoxycarbonyl.

In still a further aspect of the present invention, this disclosure provides heterocyclic compounds, wherein the compound is selected from any of the compounds in the following table, including any combination thereof. By the disclosure of these specific compounds, it is intended to include any salt, including a pharmaceutically acceptable or a non-pharmaceutically acceptable salt, any prodrug, and any stereoisomer, including diastereomeric mixtures, enantiomers, tautomers, racemic mixtures, or any combinations thereof, of the disclosed compounds.

TABLE 2

Representative examples of compounds in accordance with this disclosure, having the following general formula

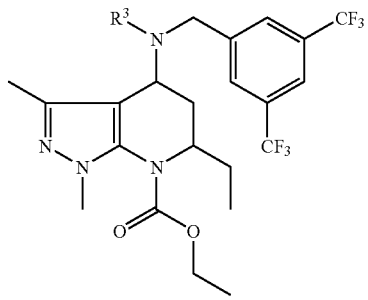

| Entry | Compound | R³ |
|---|---|---|
| 1. | 4-[(3,5-Bis-trifluoromethyl-benzyl)-(1H-tetrazol-5-yl)-amino]-6-ethyl-1,3-dimethyl-1,4,5,6-tetrahydro-pyrazolo[3,4-b]pyridine-7-carboxylic acid ethyl ester | 1H-tetrazol-5-yl |
| 2. | 4-[(3,5-Bis-trifluoromethyl-benzyl)-(2-methyl-2H-tetrazol-5-yl)-amino]-6-ethyl-1,3-dimethyl-1,4,5,6-tetrahydro-pyrazolo[3,4-b]pyridine-7-carboxylic acid ethyl ester | 2-methyl-2H-tetrazol-5-yl |
| 3. | 4-[(3,5-Bis-trifluoromethyl-benzyl)-(1-methyl-1H-tetrazol-5-yl)-amino]-6-ethyl-1,3-dimethyl-1,4,5,6-tetrahydro-pyrazolo[3,4-b]pyridine-7-carboxylic acid ethyl ester | 1-methyl-1H-tetrazol-5-yl |
| 4. | 4-[(3,5-Bis-trifluoromethyl-benzyl)-(5-methyl-[1,3,4]oxadiazol-2-yl)-amino]-6-ethyl-1,3-dimethyl-1,4,5,6-tetrahydro-pyrazolo[3,4-b]pyridine-7-carboxylic acid ethyl ester | 5-methyl-[1,3,4]oxadiazol-2-yl |
| 5. | 4-[(3,5-Bis-trifluoromethyl-benzyl)-(5-methyl-[1,2,4]oxadiazol-3-yl)-amino]-6-ethyl-1,3-dimethyl-1,4,5,6-tetrahydro-pyrazolo[3,4-b]pyridine-7-carboxylic acid ethyl ester | 5-methyl-[1,2,4]oxadiazol-3-yl |
| 6. | 4-[(3,5-Bis-trifluoromethyl-benzyl)-(2-ethyl-2H-tetrazol-5-yl)-amino]-6-ethyl-1,3-dimethyl-1,4,5,6-tetrahydro-pyrazolo[3,4-b]pyridine-7-carboxylic acid ethyl ester | 2-ethyl-2H-tetrazol-5-yl |
| 7. | 4-[(3,5-Bis-trifluoromethyl-benzyl)-(4-trifluoromethyl-oxazol-2-yl)-amino]-6-ethyl-1,3-dimethyl-1,4,5,6-tetrahydro-pyrazolo[3,4-b]pyridine-7-carboxylic acid ethyl ester | 4-trifluoromethyl-oxazol-2-yl |

TABLE 2-continued

Representative examples of compounds in accordance with this disclosure, having the following general formula

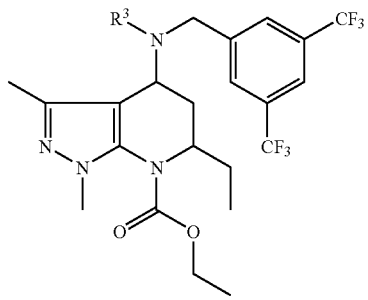

| Entry | Compound | R³ |
|---|---|---|
| 8. | 4-[(3,5-Bis-trifluoromethyl-benzyl)-methoxycarbonyl-amino]-6-ethyl-1,3-dimethyl-1,4,5,6-tetrahydro-pyrazolo[3,4-b]pyridine-7-carboxylic acid ethyl ester | methoxycarbonyl |
| 9. | 4-[(3,5-Bis-trifluoromethyl-benzyl)-tert-butoxycarbonyl-amino]-6-ethyl-1,3-dimethyl-1,4,5,6-tetrahydro-pyrazolo[3,4-b]pyridine-7-carboxylic acid ethyl ester | tert-butoxycarbonyl |
| 10. | 4-[(3,5-Bis-trifluoromethyl-benzyl)-pyrimidin-2-yl-amino]-6-ethyl-1,3-dimethyl-1,4,5,6-tetrahydro-pyrazolo[3,4-b]pyridine-7-carboxylic acid ethyl ester | pyrimidin-2-yl |
| 11. | 4-[(3,5-Bis-trifluoromethyl-benzyl)-pyridin-2-yl-amino]-6-ethyl-1,3-dimethyl-1,4,5,6-tetrahydro-pyrazolo[3,4-b]pyridine-7-carboxylic acid ethyl ester | pyridin-2-yl |
| 12. | 4-[(3,5-Bis-trifluoromethyl-benzyl)-(4-methyl-oxazol-2-yl)-amino]-6-ethyl-1,3-dimethyl-1,4,5,6-tetrahydro-pyrazolo[3,4-b]pyridine-7-carboxylic acid ethyl ester | 4-methyl-oxazol-2-yl |
| 13. | 4-[(3,5-Bis-trifluoromethyl-benzyl)-(4-methyl-thiazol-2-yl)-amino]-6-ethyl-1,3-dimethyl-1,4,5,6-tetrahydro-pyrazolo[3,4-b]pyridine-7-carboxylic acid ethyl ester | 4-methyl-thiazol-2-yl |
| 14. | 4-[(3,5-Bis-trifluoromethyl-benzyl)-(5-methyl-isoxazol-3-yl)-amino]-6-ethyl-1,3-dimethyl-1,4,5,6-tetrahydro-pyrazolo[3,4-b]pyridine-7-carboxylic acid ethyl ester | 5-methyl-isoxazol-3-yl |

TABLE 2-continued

Representative examples of compounds in accordance with this disclosure,
having the following general formula

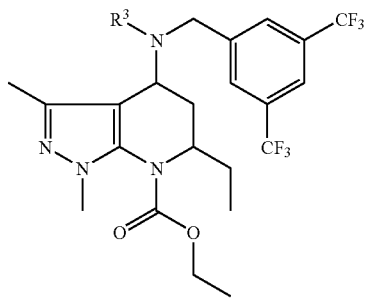

| Entry | Compound | R³ |
|---|---|---|
| 15. | 4-[(3,5-Bis-trifluoromethyl-benzyl)-(4-ethoxycarbonyl-oxazol-2-yl)-amino]-6-ethyl-1,3-dimethyl-1,4,5,6-tetrahydro-pyrazolo[3,4-b]pyridine-7-carboxylic acid ethyl ester | |
| 16. | 4-[[5-(4-Acetyl-piperazin-1-yl)-pyrimidin-2-yl]-(3,5-bis-trifluoromethyl-benzyl)-amino]-6-ethyl-1,3-dimethyl-1,4,5,6-tetrahydro-pyrazolo[3,4-b]pyridine-7-carboxylic acid ethyl ester | |
| 17. | 4-{(3,5-Bis-trifluoromethyl-benzyl)-[5-(2-methoxy-acetylamino)-pyrimidin-2-yl]-amino}-6-ethyl-1,3-dimethyl-1,4,5,6-tetrahydro-pyrazolo[3,4-b]pyridine-7-carboxylic acid ethyl ester | |
| 18. | 4-{(3,5-Bis-trifluoromethyl-benzyl)-[5-(2-morpholin-4-yl-ethoxy)-pyrimidin-2-yl]-amino}-6-ethyl-1,3-dimethyl-1,4,5,6-tetrahydro-pyrazolo[3,4-b]pyridine-7-carboxylic acid ethyl ester | |
| 19. | 4-[(3,5-Bis-trifluoromethyl-benzyl)-(5-morpholin-4-yl-pyrimidin-2-yl)-amino]-6-ethyl-1,3-dimethyl-1,4,5,6-tetrahydro-pyrazolo[3,4-b]pyridine-7-carboxylic acid ethyl ester | |

TABLE 2-continued

Representative examples of compounds in accordance with this disclosure, having the following general formula

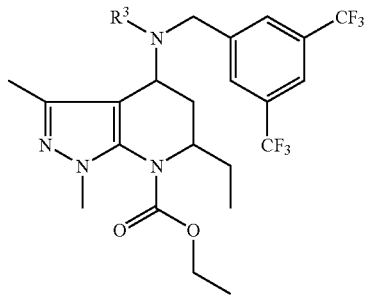

| Entry | Compound | R³ |
|---|---|---|
| 20. | 4-[(3,5-Bis-trifluoromethyl-benzyl)-(5-morpholin-4-yl-pyridin-2-yl)-amino]-6-ethyl-1,3-dimethyl-1,4,5,6-tetrahydro-pyrazolo[3,4-b]pyridine-7-carboxylic acid ethyl ester | 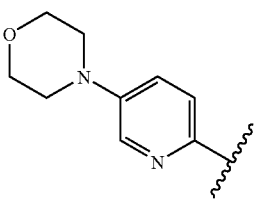 |
| 21. | 4-{(3,5-Bis-trifluoromethyl-benzyl)-[5-(2H-tetrazol-5-yl)-pyridin-2-yl]-amino}-6-ethyl-1,3-dimethyl-1,4,5,6-tetrahydro-pyrazolo[3,4-b]pyridine-7-carboxylic acid ethyl ester | 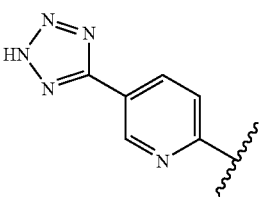 |
| 22. | 4-{(3,5-Bis-trifluoromethyl-benzyl)-[5-(pyrrolidine-1-carbonyl)-pyrimidin-2-yl]-amino}-6-ethyl-1,3-dimethyl-1,4,5,6-tetrahydro-pyrazolo[3,4-b]pyridine-7-carboxylic acid ethyl ester | 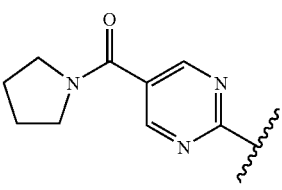 |
| 23. | 4-[{5-[Bis-(2-methoxy-ethyl)-amino]-pyrimidin-2-yl}-(3,5-bis-trifluoromethyl-benzyl)-amino]-6-ethyl-1,3-dimethyl-1,4,5,6-tetrahydro-pyrazolo[3,4-b]pyridine-7-carboxylic acid ethyl ester | 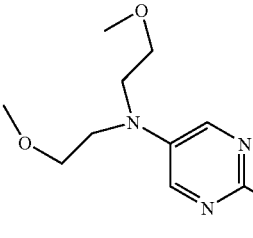 |
| 24. | 4-{(3,5-Bis-trifluoromethyl-benzyl)-[5-(3-ethoxycarbonyl-pipendin-1-yl)-pyrimidin-2-yl]-amino}-6-ethyl-1,3-dimethyl-1,4,5,6-tetrahydro-pyrazolo[3,4-b]pyridine-7-carboxylic acid ethyl ester | 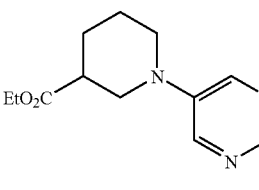 |

TABLE 2-continued

Representative examples of compounds in accordance with this disclosure,
having the following general formula

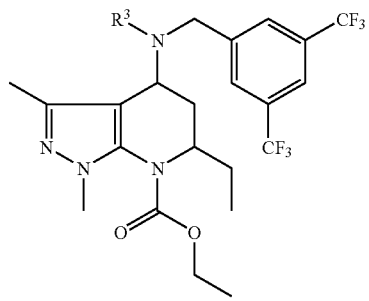

| Entry | Compound | R³ |
|---|---|---|
| 25. | 4-{(3,5-Bis-trifluoromethyl-benzyl)-[5-(2-hydroxy-ethylamino)-pyrimidin-2-yl]-amino}-6-ethyl-1,3-dimethyl-1,4,5,6-tetrahydro-pyrazolo[3,4-b]pyridine-7-carboxylic acid ethyl ester | 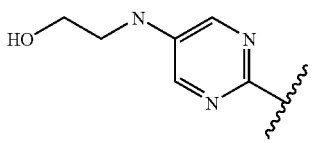 |
| 26. | 4-{(3,5-Bis-trifluoromethyl-benzyl)-[4-(3-carboxy-propoxy)-pyrimidin-2-yl]-amino}-6-ethyl-1,3-dimethyl-1,4,5,6-tetrahydro-pyrazolo[3,4-b]pyridine-7-carboxylic acid ethyl ester | 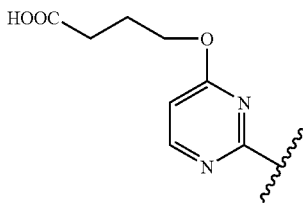 |
| 27. | 4-{(3,5-Bis-trifluoromethyl-benzyl)-[5-(2-methylsulfanyl-ethoxy)-pyrimidin-2-yl]--6-ethyl-1,3-dimethyl-1,4,5,6-amino}-6-ethyl-1,3-dimethyl-1,4,5,6-tetrahydro-pyrazolo[3,4-b]pyridine-7-carboxylic acid ethyl ester | 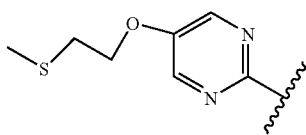 |
| 28. | 4-((3,5-Bis-trifluoromethyl-benzyl)-{5-[(2-tert-butoxycarbonyl-ethyl)-methyl-amino]-pyrimidin-2-yl}-amino)-6-ethyl-1,3-dimethyl-1,4,5,6-tetrahydro-pyrazolo[3,4-b]pyridine-7-carboxylic acid ethyl ester | 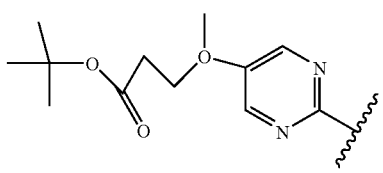 |
| 29. | 4-{(3,5-Bis-trifluoromethyl-benzyl)-[5-(2-carboxy-ethyl)-pyrimidm-2-yl]-amino}-6-ethyl-1,3-dimethyl-1,4,5,6-tetrahydro-pyrazolo[3,4-b]pyridine-7-carboxylic acid ethyl ester | 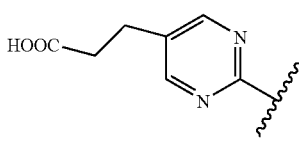 |

In yet an additional or a further aspect, the present invention provides compounds and compositions comprising these compounds, wherein the compounds have the following formula:

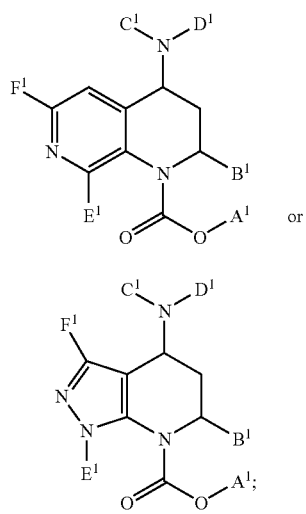

or a salt, including a pharmaceutically acceptable or a non-pharmaceutically acceptable salt, a prodrug, a diastereomeric mixture, an enantiomer, a tautomer, a racemic mixture thereof, or any combination thereof, wherein:

$A^1$ is selected from methyl, ethyl, propyl, butyl, pentyl, hexyl, heptyl,

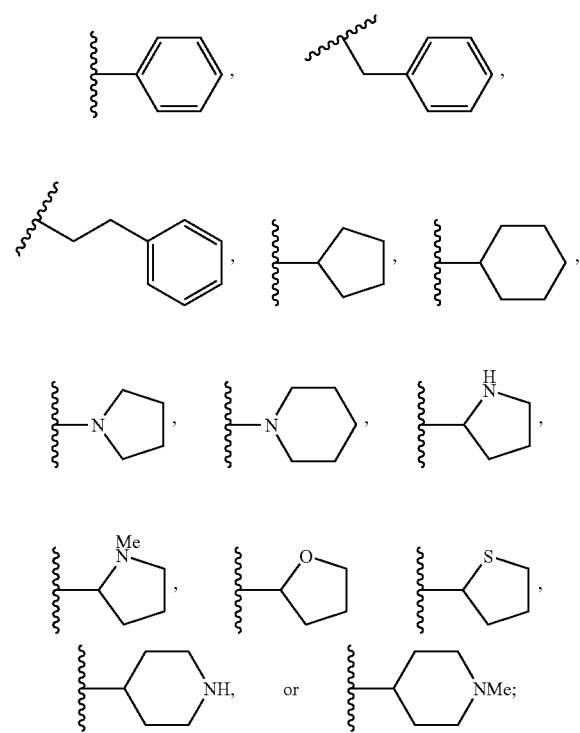

$B^1$ is selected from H, methyl, ethyl, propyl, butyl, pentyl, hexyl, heptyl, $CF_3$, $CF_2CF_3$, $CH_2Cl$, $CH_2F$, $CH_2CH_2Cl$, $CH_2CH_2F$,

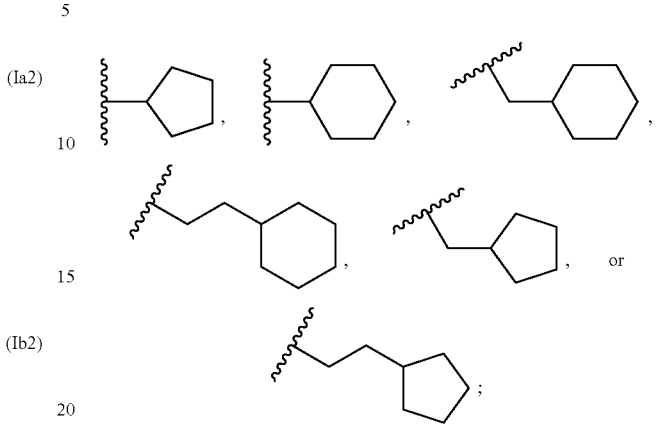

$C^1$ is selected from H, methyl, ethyl, propyl, butyl, pentyl, hexyl, heptyl, $CO_2H$, $CO_2Me$, $CO_2Et$, $CO_2CF_3$, $COMe$, $COEt$, $SO_2Me$, $SO_2Et$, $SO_2NH_2$, $SO_2NMe_2$, $CONH_2$, $CONMe_2$,

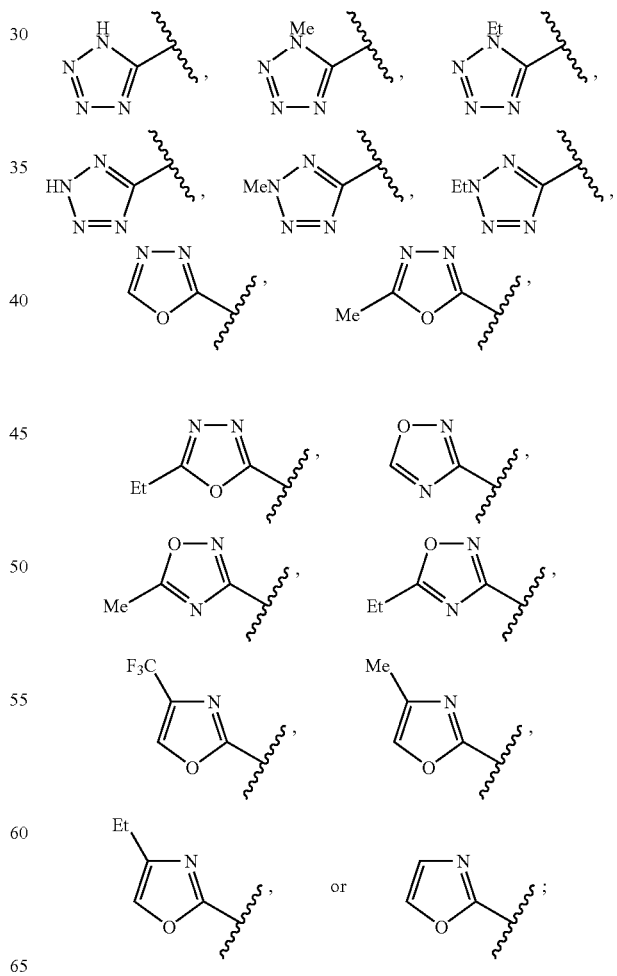

$D^1$ is selected from

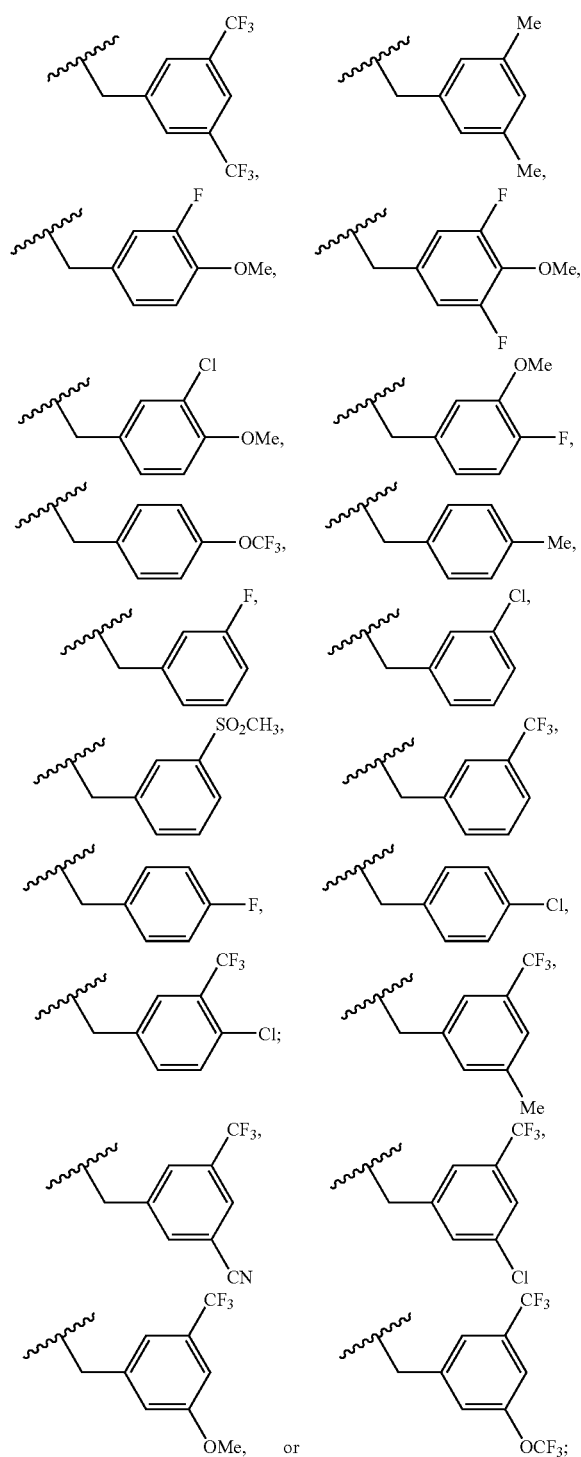

$E^1$ is selected from H, OH, methyl, ethyl, propyl, butyl, pentyl, hexyl, heptyl, $CF_3$, $CF_2CF_3$, $CH_2Cl$, $CH_2F$, $CH_2CH_2Cl$, $CH_2CH_2F$, OMe, OEt, OPr, OBu, $OCH_2F$, $OCH_2Cl$, $OCF_3$, $OCCl_3$, $OCH_2CH_2F$, $OCH_2CH_2Cl$, $OCH_2CCl_3$, $OCH_2CF_3$, $OCF_2CF_3$, $OC(CH_3)_2(CF_3)$, $OC(CH_3)(CF_3)_2$, $OC(CF_3)_3$, phenyl, naphthyl, 1,2,3,4-tetrahydronaphthyl, indanyl, indenyl, or fluorenyl; and $F^1$ is selected from H, CN, F, Cl, Br, I, methyl, ethyl, propyl, butyl, pentyl, hexyl, heptyl, $CF_3$, $CF_2CF_3$, $CH_2Cl$, $CH_2F$, $CH_2CH_2Cl$, $CH_2CH_2F$, OMe, OEt, OPr, OBu, $OCH_2F$, $OCH_2Cl$, $OCF_3$, $OCCl_3$, $OCH_2CH_2F$, $OCH_2CH_2Cl$, $OCH_2CCl_3$, $OCH_2CF_3$, $OCF_2CF_3$, $OC(CH_3)_2(CF_3)$, $OC(CH_3)(CF_3)_2$, $OC(CF_3)_3$, phenyl, naphthyl, 1,2,3,4-tetrahydronaphthyl, indanyl, indenyl, or fluorenyl.

In still another aspect, the present invention provides compounds and compositions comprising these compounds, wherein the compounds have the following formula:

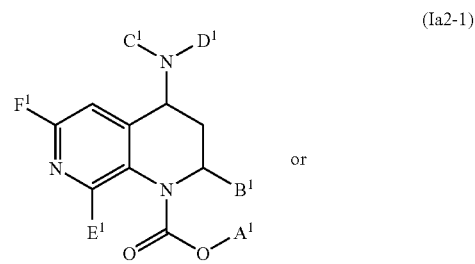

(Ia2-1)

or

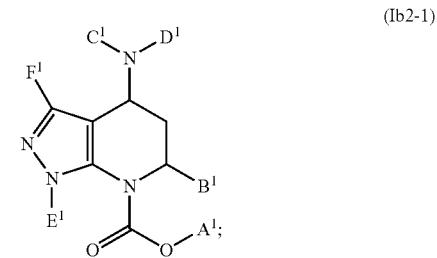

(Ib2-1)

or a salt, including a pharmaceutically acceptable or a non-pharmaceutically acceptable salt, a prodrug, a diastereomeric mixture, an enantiomer, a tautomer, a racemic mixture thereof, or any combination thereof, wherein:

$A^1$ is selected from methyl, ethyl, propyl, butyl, pentyl, hexyl, or heptyl; and $B^1$, $C^1$, $D^1$, $E^1$, and $F^1$ are selected as indicated above according to formulas (Ia2) and (Ib2).

In yet an additional or a further aspect, the present invention provides compounds according to formula (I) and compositions comprising these compounds, wherein the compounds have the following formula (Ia3)

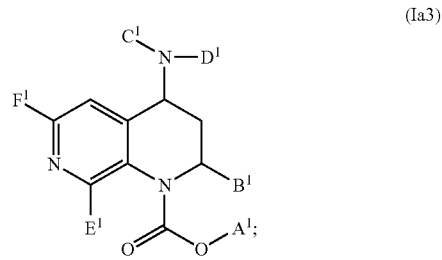

(Ia3)

or a salt, including a pharmaceutically acceptable or a non-pharmaceutically acceptable salt, a prodrug, a diastereomeric mixture, an enantiomer, a tautomer, a racemic mixture thereof, or any combination thereof, wherein:

A¹ is selected from methyl, ethyl, propyl, iso-butyl, iso-propyl, neo-pentyl,

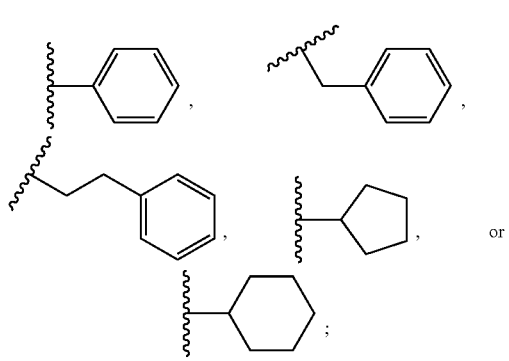

B¹ is selected from hydrogen, methyl, ethyl, propyl, or cyclopropyl;

C¹ is selected from $CO_2Me$, $CO_2Et$, $SO_2Me$, $SO_2Et$, $SO_2NMe_2$, $CONMe_2$,

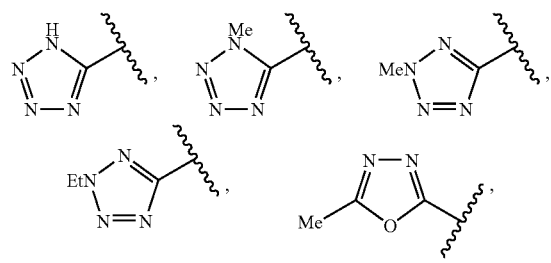

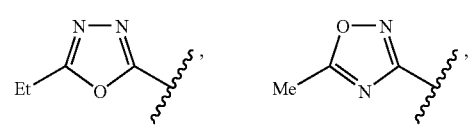

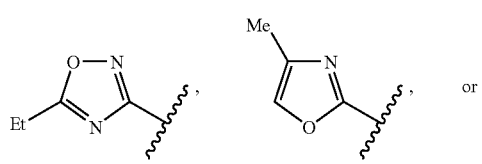

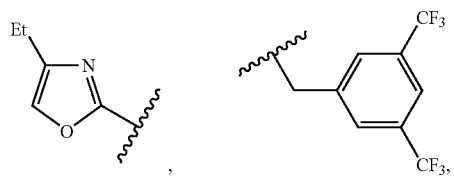

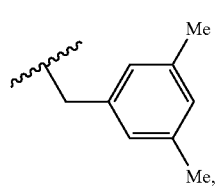

D¹ is selected from

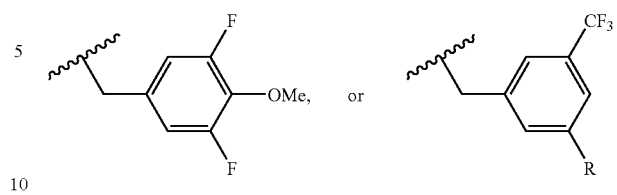

wherein R is Me, CN, Cl, OMe, or $OCF_3$;

E¹ is selected from hydrogen, OH, methyl, ethyl, iso-propyl, iso-butyl, CN, $CO_2R^6$, $CF_3$, methoxy, $OCF_3$, or phenyl;

R⁶ is an alkyl or a haloalkyl, any of which having up to 12 carbon atoms, or hydrogen; and F¹ is selected from hydrogen, CN, Cl, methyl, ethyl, $CF_3$, methoxy, $OCF_3$, or phenyl.

In still a further aspect, the present invention provides compounds according to formula (Ia3) and compositions comprising these compounds, wherein A¹, B¹, C¹, D¹, and F¹ are selected as indicated above for formula (Ia3), and E¹ is selected from hydrogen, OH, methyl, ethyl, iso-propyl, iso-butyl, CN, $CO_2Me$, $CO_2Et$, $CO_2Pr$, $CF_3$, methoxy, $OCF_3$, or phenyl.

In yet an additional or a further aspect, the present invention provides compounds according to formula (I) and compositions comprising these compounds, wherein the compounds have the following formula (Ib3):

(Ib3)

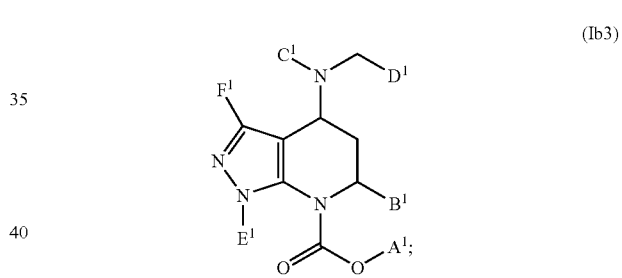

or a salt, including a pharmaceutically acceptable or a non-pharmaceutically acceptable salt, a prodrug, a diastereomeric mixture, an enantiomer, a tautomer, a racemic mixture thereof, or any combination thereof, wherein:

A¹, B¹, C¹, D¹, and F¹ are selected as indicated above for formula (Ia3); and

E¹ is selected from hydrogen, methyl, ethyl, propyl, or aryl.

According to another aspect of this invention, and consistent with the definitions provided herein, the present invention also provides for compounds of the following general structures:

(IIa)

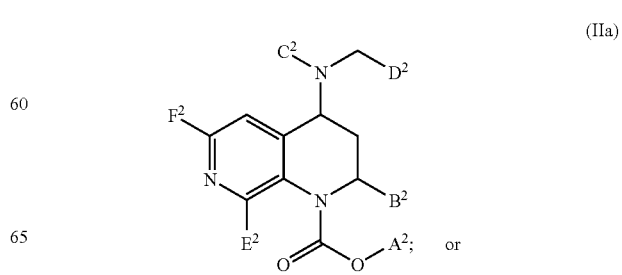

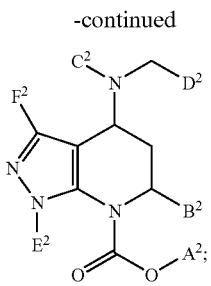

(IIb)

or a salt, including a pharmaceutically acceptable or a non-pharmaceutically acceptable salt, a prodrug, a diastereomeric mixture, an enantiomer, a tautomer, a racemic mixture thereof, or any combination thereof, wherein within each structure, the substituents $A^2$, $B^2$, $C^2$, $D^2$, $E^2$, and $F^2$ can be selected according to the following listings, wherein each substituent is defined in the following table.

The substituent $A^2$ can be selected independently from $A^{2A}$, $A^{2B}$, $A^{2C}$, $A^{2D}$, $A^{2E}$, $A^{2F}$, $A^{2G}$, $A^{2H}$, $A^{2I}$, or $A^{2J}$.

The substituent $B^2$ can be selected independently from $B^{2A}$, $B^{2B}$, $B^{2C}$, $B^{2D}$, or $B^{2E}$.

The substituent $C^2$ can be selected independently from $C^{2A}$, $C^{2B}$, $C^{2C}$, $C^{2D}$, $C^{2E}$, $C^{2F}$, $C^{2G}$, $C^{2H}$, $C^{2I}$, $C^{2J}$, $C^{2K}$, $C^{2L}$, $C^{2M}$, $C^{2N}$, $C^{2O}$, $C^{2P}$, or $C^{2Q}$.

The substituent $D^2$ is a substituted phenyl group, substituted with from 0 to 3 substituents that are selected independently from $D^{2A}$, $D^{2B}$, $D^{2C}$, $D^{2D}$, $D^{2E}$, $D^{2F}$, $D^{2G}$, $D^{2H}$, $D^{2I}$, $D^{2J}$, or $D^{2K}$.

The substituent $E^2$ can be selected independently from $E^{2A}$, $E^{2B}$, $E^{2C}$, $E^{2D}$, $E^{2E}$, $E^{2F}$, $E^{2G}$, $E^{2H}$, $E^{2I}$ or $E^{2J}$.

The substituent $F^2$ can be selected independently from $F^{2A}$, $F^{2B}$, $F^{2C}$, $F^{2D}$, $F^{2E}$, $F^{2F}$, $F^{2G}$, $F^{2H}$, $F^{2I}$, or $F^{2J}$.

The substituent $R^6$, which is disclosed in the following table, can be selected from $R^{6A}$, $R^{6B}$, or $R^{6C}$.

The substituent $R^7$, which is disclosed in the following table, can be selected from $R^{7A}$, $R^{7B}$, or $R^{7C}$.

The substituent $R^8$, which is disclosed in the following table, can be selected from $R^{8A}$.

The substituents recited above are defined as follows, consistent with the definitions provided herein.

TABLE 3

Substituent abbreviations.

| | |
|---|---|
| $A^{2A}$ | Alkyl having up to 12 carbon atoms |
| $A^{2B}$ | Cycloalkyl having up to 12 carbon atoms |
| $A^{2C}$ | Aryl having up to 12 carbon atoms |
| $A^{2D}$ | Aralkyl having up to 12 carbon atoms |
| $A^{2E}$ | Heterocyclyl having up to 12 carbon atoms, comprising >O |
| $A^{2F}$ | Heterocyclyl having up to 12 carbon atoms, comprising >N- |
| $A^{2G}$ | Heterocyclyl having up to 12 carbon atoms, comprising >S |
| $A^{2H}$ | Heterocyclyl having up to 12 carbon atoms, comprising >$NR^6$ |
| $A^{2I}$ | Heterocyclyl having up to 12 carbon atoms, comprising >$SO_2$ |
| $A^{2J}$ | Heterocyclyl having up to 12 carbon atoms, comprising >CO |
| $B^{2A}$ | Hydrogen |
| $B^{2B}$ | Alkyl having up to 12 carbon atoms |
| $B^{2C}$ | Haloalkyl having up to 12 carbon atoms |
| $B^{2D}$ | Cycloalkyl having up to 12 carbon atoms |
| $B^{2E}$ | Cycloalkyl-substituted alkyl having up to 12 carbon atoms |
| $C^{2A}$ | Alkyl having up to 12 carbon atoms |
| $C^{2B}$ | $CO_2R^6$ |
| $C^{2C}$ | $COR^8$ |
| $C^{2D}$ | $SO_2R^8$ |
| $C^{2E}$ | $SO_2NR^6R^7$ |
| $C^{2F}$ | $CONR^6R^7$ |

TABLE 3-continued

Substituent abbreviations.

| | |
|---|---|
| $C^{2G}$ | A substituted or an unsubstituted, 5-, 6-, or 7-membered heterocyclyl comprising >O, having up to 12 carbon atoms |
| $C^{2H}$ | A substituted or an unsubstituted, 5-, 6-, or 7-membered heterocyclyl comprising >N-, having up to 12 carbon atoms |
| $C^{2I}$ | A substituted or an unsubstituted, 5-, 6-, or 7-membered heterocyclyl comprising >S, having up to 12 carbon atoms |
| $C^{2J}$ | A substituted or an unsubstituted, 5-, 6-, or 7-membered heterocyclyl comprising >$NR^6$, having up to 12 carbon atoms |
| $C^{2K}$ | A substituted or an unsubstituted, 5-, 6-, or 7-membered heteroaryl comprising >O, having up to 12 carbon atoms |
| $C^{2L}$ | A substituted or an unsubstituted, 5-, 6-, or 7-membered heteroaryl comprising >N-, having up to 12 carbon atoms |
| $C^{2M}$ | A substituted or an unsubstituted, 5-, 6-, or 7-membered heteroaryl comprising >S, having up to 12 carbon atoms |
| $C^{2N}$ | A substituted or an unsubstituted, 5-, 6-, or 7-membered heteroaryl comprising >$NR^6$, having up to 12 carbon atoms |
| $C^{2O}$ | A substituted or an unsubstituted aryl having up to 12 carbon atoms |
| $C^{2P}$ | Hydrogen |
| $C^{2Q}$ | Cyano |
| $D^{2A}$ | Alkyl having up to 12 carbon atoms |
| $D^{2B}$ | Cycloalkyl having up to 12 carbon atoms |
| $D^{2C}$ | Haloalkyl having up to 12 carbon atoms |
| $D^{2D}$ | Alkoxy having up to 12 carbon atoms |
| $D^{2E}$ | Heteroaryl having up to 12 carbon atoms, comprising >O |
| $D^{2F}$ | Heteroaryl having up to 12 carbon atoms, comprising >N- |
| $D^{2G}$ | Heteroaryl having up to 12 carbon atoms, comprising >S |
| $D^{2H}$ | Heteroaryl having up to 12 carbon atoms, comprising >$NR^6$ |
| $D^{2I}$ | Halogen |
| $D^{2J}$ | Hydroxyl |
| $D^{2K}$ | Cyano |
| $E^{2A}$ | Alkyl having up to 12 carbon atoms |
| $E^{2B}$ | Haloalkyl having up to 12 carbon atoms |
| $E^{2C}$ | Alkoxy having up to 12 carbon atoms |
| $E^{2D}$ | Haloalkoxy having up to 12 carbon atoms |
| $E^{2E}$ | Aryl having up to 12 carbon atoms |
| $E^{2F}$ | $CO_2R^6$ |
| $E^{2G}$ | $COR^8$ |
| $E^{2H}$ | Cyano |
| $E^{2I}$ | Hydrogen |
| $E^{2J}$ | Hydroxyl |
| $F^{2A}$ | Alkyl having up to 12 carbon atoms |
| $F^{2B}$ | Haloalkyl having up to 12 carbon atoms |
| $F^{2C}$ | Alkoxy having up to 12 carbon atoms |
| $F^{2D}$ | Haloalkoxy having up to 12 carbon atoms |
| $F^{2E}$ | Aryl having up to 12 carbon atoms |
| $F^{2F}$ | $CO_2R^6$ |
| $F^{2G}$ | $COR^8$ |
| $F^{2H}$ | Hydrogen |
| $F^{2I}$ | Halogen |
| $F^{2J}$ | Cyano |
| $R^{6A}$ | Alkyl having up to 12 carbon atoms |
| $R^{6B}$ | Haloalkyl having up to 12 carbon atoms |
| $R^{6C}$ | Hydrogen |
| $R^{7A}$ | Alkyl having up to 12 carbon atoms |
| $R^{7B}$ | Haloalkyl having up to 12 carbon atoms |
| $R^{7C}$ | Hydrogen |
| $R^{8A}$ | Alkyl having up to 12 carbon atoms |

In these selections, unless otherwise indicated, the number of carbon atoms on the substituents refers to the carbon atoms on the base chemical moiety, and does not include the carbon atoms in any optional substituent. Again, unless otherwise indicated, any substituents are limited in size by the carbon atoms listed in the definitions of the substitutents. Further, when these selections refer to a substituted moiety or group, unless otherwise specified, substituents are selected as indicated in formula (I) above.

In these selections, the following features are applicable. When $C^2$ is a heterocyclyl or a heteroaryl, specifically, when $C^2$ is a substituted or an unsubstituted, 5-, 6-, or 7-membered heterocyclyl or heteroaryl, comprising from 1 to 4 heteroatoms or heterogroups selected independently from >O, >N—, >S, or >$NR^6$, then $C^2$ is optionally substituted with at least one alkyl, haloalkyl, cycloalkyl, alkoxycarbonyl, or heterocyclyl, any of which having up to 12 carbon atoms, wherein any heterocyclyl comprises at least one heteroatom or heterogroup selected independently from >O, >N—, >S, >NR$^6$, >SO$_2$, or >CO; or C$^2$ is optionally substituted with NR$^6$R$^7$. In this aspect, R$^6$ and R$^7$ are as defined in the table above.

The present invention also encompasses any combination of compounds provided herein, including any salts, including pharmaceutically acceptable and non-pharmaceutically acceptable salts, or any mixture thereof. The present invention also encompasses any stereoisomers of compounds provided herein, including any combination of stereoisomers.

In this aspect of the present invention, compounds provided herein can be chiral or achiral, or they may exist as racemic mixtures, diastereomers, pure enantiomers, a prodrug, a tautomer or any mixture thereof. For chiral compounds, separate enantiomers, separate diastereomers, and any mixture of enantiomers, diastereomers, or both are encompassed herein, such as, for example, (R), (S), or a mixture of (R) and (S) isomers. In this aspect, individual optical isomers or a particular desired isomer may be obtained by using chiral reagents to obtain a single isomeric form in a resolution process wherever applicable, or by conducting the reaction in the presence of reagents or catalysts in their single enantiomeric or diasteromeric form.

In one aspect, methods for the resolution of racemic compounds include, but are not limited to: using microbial resolution; resolving the diastereomeric salts formed with chiral acids such as mandelic acid, camphorsulfonic acid, tartaric acid, lactic acid, and the like wherever applicable; or resolving the diastereomeric salts formed with chiral bases such as brucine, cinchona alkaloids and their derivatives; and the like. Commonly used methods are compiled in Jaques, et al. in *Enantiomers, Racemates and Resolution*; Wiley-Interscience, 1981. For example, where appropriate, compounds of formula (I) can be resolved by treating with chiral amines, aminoacids, or aminoalcohols derived from aminoacids; by using conventional reaction conditions to convert an acid into an amide; by separation of diastereomers by fractional crystallization or by chromatography; or by preparing the stereoisomers of formula (I) by hydrolyzing the pure diastereomeric amide.

As used herein, the terms "pharmaceutically acceptable" salt or "pharmacologically acceptable" salt refers generally to a salt or complex of the compound or compounds in which the compound can be either anionic or cationic, and have associated with it a counter cation or anion, respectively, that is generally considered suitable for human or animal consumption. For example, a pharmaceutically acceptable salt can refer to a salt of a compound disclosed herein that forms upon reaction or complexation with an acid whose anion is generally considered suitable for human or animal consumption. In this aspect, pharmacologically acceptable salts include salts with organic acids or inorganic acids. Examples of pharmacologically acceptable salts include, but are not limited to, hydrochloride, hydrobromide, hydroiodide, sulfate, phosphate, propionate, lactate, maleate, malate, succinate, tartarate, and the like.

Salts may also be formed by deprotonating an acid moiety of the compound, such as a carboxylic acid moiety, OH, or NH, and the like, using a base such as an organic base, an inorganic base, an organometallic base, a Lewis base, a Brønsted base, or any combination thereof. In cases where compounds carry an acidic moiety, suitable pharmaceutically acceptable salts can include alkali metal salts, alkaline earth metal salts, or salts with organic basis, and the like. In this aspect, examples of alkali metal salts include, but are not limited to, sodium and potassium salts, and examples of salts with organic basis include, but are not limited to, meglumine salts, and the like. The pharmacologically acceptable salts can be prepared by conventional means. Additional examples of pharmaceutically acceptable salts, and methods of preparing such salts, are found, for example, in Berg et. al., J. Pharma. Sci, 66, 1-19 (1977).

In a further aspect, this invention also provides a composition comprising at least one compound as disclosed herein, including a composition comprising a pharmaceutically acceptable carrier and at least one compound as disclosed herein. In this aspect, the at least one compound can be present as a neutral compound, as a salt, or as any combination thereof. This invention also encompasses a composition comprising at least one compound as disclosed herein, and optionally comprising a pharmaceutically acceptable additive selected from a carrier, an auxiliary, a diluent, an excipient, a preservative, a solvate, or any combination thereof. In another aspect, this invention encompasses a pharmaceutical composition comprising at least one compound as disclosed herein, and optionally further comprising an agent selected from a chemotherapeutic agent, an immunosuppressive agent, a cytokine, a cytotoxic agent, an anti-inflammatory agent, an antidyspilidemic agent, an antirheumatic agent, a cardiovascular agent, or any combination thereof.

Further, this invention encompasses a pharmaceutical composition, comprising at least one compound as disclosed herein, and optionally comprising a pharmaceutically acceptable additive selected from a carrier, an auxiliary, a diluent, an excipient, a preservative, a solvate, or any combination thereof, wherein the pharmaceutical composition is in the form of a tablet, a capsule, a syrup, a cachet, a powder, a granule, a solution, a suspension, an emulsion, a bolus, a lozenge, a suppository, a cream, a gel, a paste, a foam, a spray, an aerosol, a microcapsule, a liposome, or a transdermal patch.

Prodrugs

In another aspect of this invention, alternatively, the compounds can be formulated and administered in a prodrug form. In general, prodrugs comprise functional derivatives of the claimed compounds which are capable of being enzymatically activated or converted into the more active parent form. Thus, in the treatment methods of the present invention, the term "administering" encompasses the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in Wihnan, 14 *Biochem. Soc. Trans.* 375-82 (1986); Stella et al., Prodrugs: A Chemical Approach to Targeted Drug Delivery, in *Directed Drug Delivery* 247-67 (1985).

Thus, in one aspect, "prodrugs" of the compounds disclosed herein refers to species that have chemically- or metabolically-cleavable groups wherein, under physiological conditions, the species become, provide, release, or are transformed into the compounds disclosed herein. In this manner, prodrugs can release the pharmaceutically in vivo active compounds disclosed herein. For example, prodrugs of present invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine or other 5-fluorouridine prodrugs which may be converted into the more active species, and the like. In another aspect, prodrugs of present invention include, but are not limited to derivatives of carboxylic acid, sulfonamide, amine, hydroxyl, and the like, including other functional groups and including any combination thereof.

In another aspect, this invention provides a pharmaceutical composition, comprising one or more compounds of any formula in any combination described above and optionally comprising a pharmaceutically acceptable additive selected from a carrier, an auxiliary, a diluent, an excipient, a preservative, a solvate, or any combination thereof. In a related aspect, this invention affords a method of treating a condition or disease state such as dyslipidemia, atherosclerosis, peripheral vascular disease, hypertryglyceridemia, hypercholesterolemia, hyperbetalipoproteinemia, hypoalphalipoproteinemia, cardiovascular disorders such as angina, ischemia, stroke, myocardial infarction (MI), reperfusion injury, restenosis and hypertension, and diabetic vascular diseases such as diabetic retinopathy, and endotoxemia, comprising administering an effective amount of at least one compound as disclosed herein.

Synthetic Methods

General reaction schemes are provided herein that detail the synthetic approaches to the bicyclic heterocyclic compounds disclosed herein. Thus, compounds in accordance with this disclosure could be prepared as shown in the specific Schemes and/or as illustrated in the Examples by using standard synthetic methods and starting materials, which are either commercially available or can be synthesized from commercially available precursors using synthetic methods known in the art, or variations thereof as appreciated by those skilled in the art. Each variable in the following schemes refer to any group consistent with the description of the compounds provided herein. In each synthetic scheme or example provided herein, substitutents in any structure that are illustrated in any scheme or example, that are not specified, are selected as disclosed according to the general formulas of the disclosed compounds, as provided herein.

The following general procedures could be used in the reactions schemes and in the Examples provided herein.

Halogenation could be carried out by using reagents such as phosphorus oxychloride ($POCl_3$), thionyl chloride ($SOCl_2$), and the like, for example, at a temperature from about 80° C. to about 120° C., for about 4 to about 8 hours, followed by pH adjustment of resultant mixture to a pH from about 6 to about 7.

Amination could be carried out by using amines in presence of a solvent chosen from acetone, acetonitrile, dimethylformamide, dimethylacetamide and the like, with or without a base. Suitable bases include triethylamine, N,N-diisopropyl ethyl amine, potassium carbonate, sodium carbonate, sodium hydride, and the like. The reaction temperature was typically from about 20° C. to about 120° C. The duration of the reaction was typically in the range of from about 4 hours to about 20 hours.

Arylation was carried out by aryl boronic acids, for example in the presence of a palladium catalyst and a base such as sodium carbonate, potassium carbonate, sodium or potassium tert-butoxide, potassium phosphate and the like, at ambient temperature or elevated temperatures using various inert solvents. Examples of suitable solvents include, but are not limited to toluene, dioxane, DMF, n-methyl pyrolidine, ethylene glycol, dimethyl ether, diglyne, and acetonitrile. Commonly employed palladium catalysts include [tetrakis(triphenylphosphine) palladium (0)] [$(PPh_3)_4Pd$], tris(dibenzeledine acetone)dipalladium (0) or palladium (II) acetate[$Pd(OAc)_2$], [bis(triphenylphosphine)palladium(II)chloride] [$(PPh_3)_2PdCl_2$] (Suzuki reaction, Miyaura and Suzuki (1995, Chemical Reviews 95:2457).

Thus one further aspect of the invention relates to the processes of preparing compounds of formulas provided herein. Any compound of any formula disclosed herein can be obtained using procedures provided in the reaction Schemes, as well as procedures provided in the Examples, by selecting suitable starting materials and following analogous procedures. Thus, any compound of any formula disclosed or exemplified herein, can be obtained by using the appropriate starting materials and appropriate reagents, with the desired substitutions, and following procedures analogous to those described herein. Therefore, it will be readily understood by one of ordinary skill, that the reaction schemes disclosed herein can be adapted to prepare any compound of this disclosure, therefore any discussion of a particular step in a reaction scheme is intended to reflect one method or one set of considitions that can be used to carry out that step. This discussion of a particular step is not intended to be limiting, but rather exemplary, of one particular method and set of conditions by which that step can be effected.

In one aspect of this invention, compounds of formula (I) according to this invention could be prepared as illustrated in the following scheme. The starting materials of this scheme are either commercially available or others are well known in the chemical literature and readily prepared. Representative steps are provided as follows. Substitutents in the structures illustrated in any scheme that are not specified are selected as provided herein in the general description of the disclosed compounds.

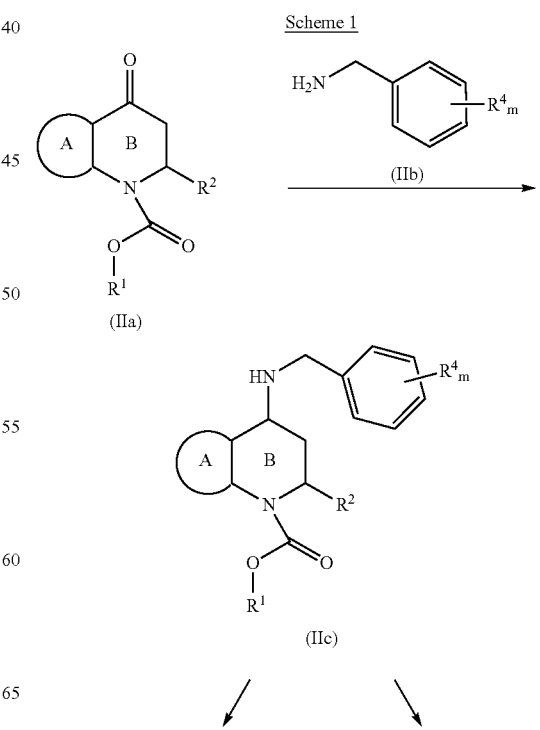

Scheme 1

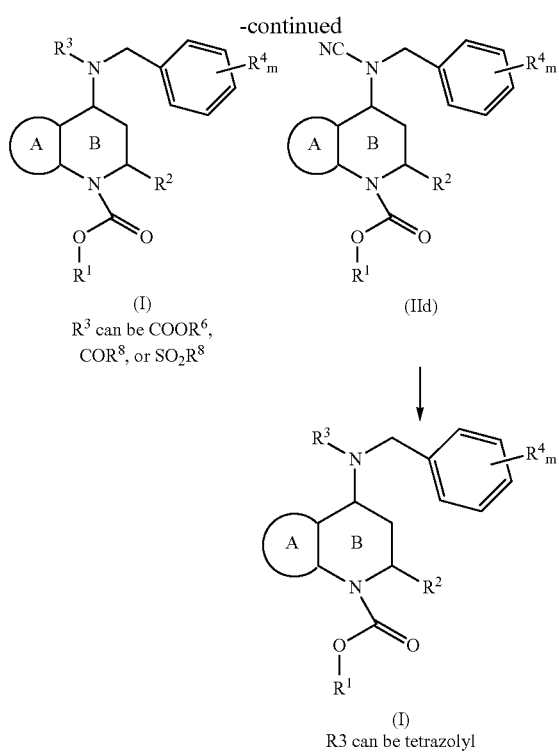

Reductive amination of compounds of formula (IIa) with compounds of formula (IIb) could be effected in the presence of one or more reducing agents such as Na(CN)BH$_3$, Na(OAc)$_3$BH, NaBH$_4$, or a combination thereof, in an appropriate solvent medium. For example, appropriate solvents include, but are not limited to, alcohols such as methanol, ethanol, and the like, or chlorinated solvents such as dichloromethane. Typically this reaction can be carried out with a catalytic amount of one or more acids, such as acetic acid, typically at a temperature from about 15° C. to about 50° C., and for a period of time from about 0.25 hours to about 6 hours, to provide compounds of formula (IIc).

Compounds of formula (IIc) could be reacted with L-COOR$^6$, L-COR$^8$, or L-SO$_2$R$^8$, wherein L represents leaving group such as a halogen, in the presence of a base such as triethylamine, disopropylamine, K$_2$CO$_3$, Na$_2$CO$_3$, potassium-t-butoxide, and the like. Solvents for this reaction include solvents such as dichloromethane, tetrahydrofuran, methyl t-butyl ether, and the like, and this transformation can typically be conducted at a temperature in the range of from about 0° C. to about 90° C., and for a period of time from about 4 hours to about 12 hours, to yield compounds of formula (I), wherein R$^3$ can be CO$_2$R$^6$, COR$^8$, or SO$_2$R$^8$. The other substitutents in the structures of scheme that are not specified are selected as provided herein.

Compounds of formula (IIc) could be reacted with cyanogen bromide (NCBr), in the presence of a base such as NaHCO$_3$, Na$_2$CO$_3$, KHCO$_3$, K$_2$CO$_3$, and the like, to yield compounds of formula (IId). Typically, this reaction can be carried out at a temperature from about 15° C. to about 50° C., in a solvent such as methanol, ethanol, chloroform, diethyl-ether, DMF, ethyl acetate, and the like, typically for a period of time ranging from about 2 hours to about 8 hours.

Compounds of formula (IId) could be reacted with sodium azide (NaN$_3$) in presence of an ammonium halide such as ammonium chloride in solvents such as N,N-dimethylformamide (DMF), to yield compounds of formula (I), wherein R$^3$ can be tetrazolyl. In one aspect, for example, this reaction can typically be carried out in an aqueous solvent, at a temperature ranging from about 100° C. to about 120° C., for a period of from about 12 hours to about 18 hours.

Compounds of formula (I), wherein R$^3$ is tetrazolyl, can be converted to a compound of formula (I) wherein R$^3$ represents an alkyl substituted [1,2,4]oxadiazolyl, upon reacting the tetrazolyl-substituted compound (I) with an acid chloride such as acetyl chloride. This reaction could be carried out in the presence of an appropriate solvent such as pyridine, typically at a temperature from about 120° C. to about 140° C., and for a time period ranging from about 2 to about 6 hours.

Compounds of formula (I), wherein R$^3$ is tetrazolyl, can be converted to a compound of formula (I) wherein R$^3$ represents an alkyl substituted tetrazolyl, upon reacting the tetrazolyl compound (I) with alkylating reagents such as alkyl halides, dialkyl sulphates, or the like.

In still another aspect of this invention, compounds of formula (Ib) according to this invention could be prepared as illustrated in the following scheme. The starting materials of this scheme are either commercially available or others are well known in the chemical literature and readily prepared. Representative steps of this scheme are provided as follows.

Scheme 2

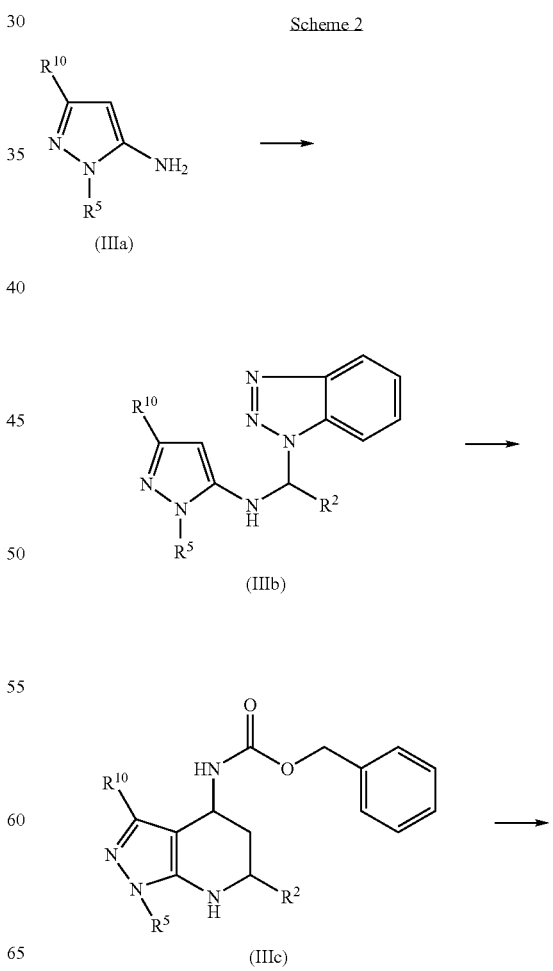

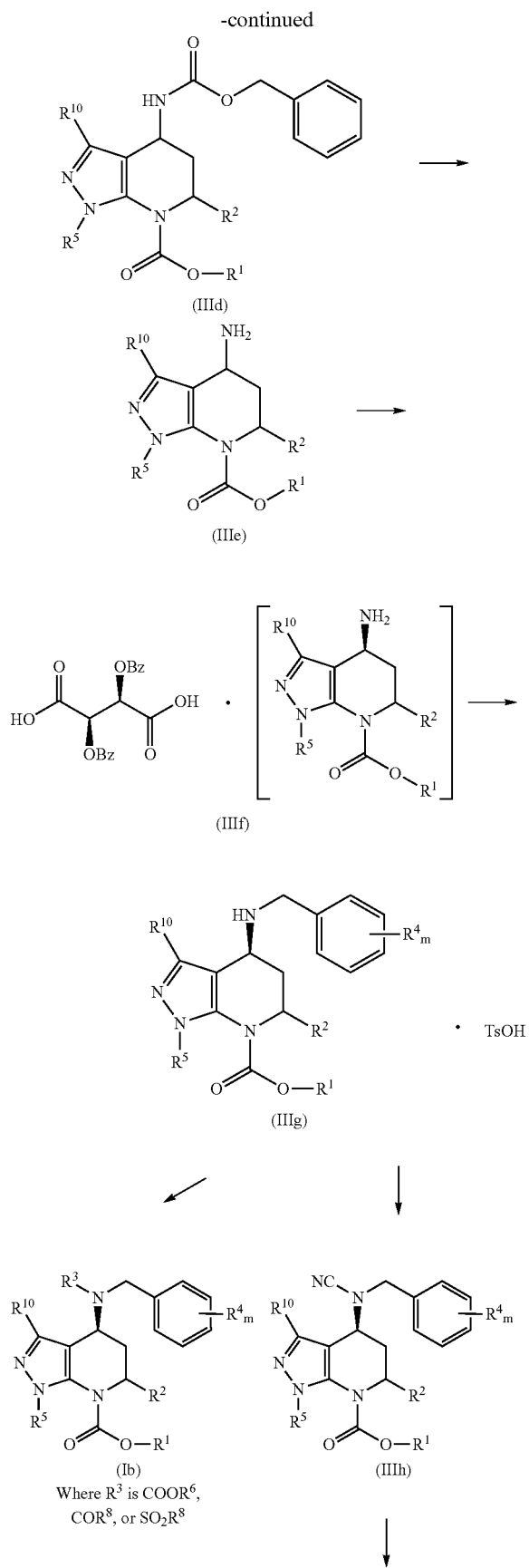

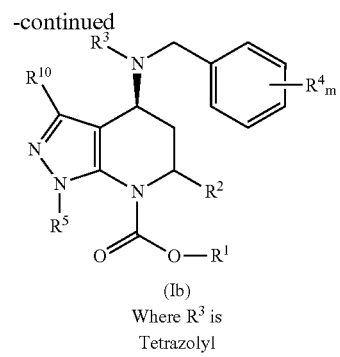

Compounds of formula (IIIg) could be prepared from compounds of formula (IIIa) by the synthetic strategy provided in Scheme 2, aspects of which are disclosed in U.S. Pat. No. 6,313,142. Compounds of formula (IIIg) could then be reacted with NCBr in the presence of a base such as $NaHCO_3$, $Na_2CO_3$, $KHCO_3$, $K_2CO_3$, and the like, to provide compounds of formula (IIIh). In one aspect, for example, this reaction could be carried out at a temperature in the range of form about 15° C. to about 50° C., typically in the presence of an alcohol solvbent, a chlorinated solbent, an ether solvent, and/or an ester solvent, and for a time period in the range of about 2 hours to about 8 hours. Examples of solvents include, but are not limited to, methanol, ethanol, chloroform, diethylether, N,N-dimethylformamide (DMF), ethyl acetate, and the like.

Compounds of formula (IIIh) could be reacted with sodium azide ($NaN_3$) in presence of an ammonium halide such as ammonium chloride in solvents such as N,N-dimethylformamide (DMF), to yield compounds of formula (Ib), wherein $R^3$ can be tetrazolyl. The tetrazolyl moiety $R^3$ shown in this scheme can be readily substituted with, or converted to, a substituted tetrazole $R^3$. In one aspect, this reaction could be carried out in solvents such as N,N-dimethylformamide (DMF) or THF, typically at a temperature from about room temperature to about 120° C., for a duration from about 2 hours to about 18 hours.

Compounds of formula (III), wherein $R^3$ is tetrazolyl, could be converted to an analogous compound of formula (III), wherein $R^3$ is [1,2,4]oxadiazolyl, by the reaction of the tetrazolyl compound (III) with acetyl chloride, typically in a solvent such as pyridine. In one aspect, this reaction could be carried out at a temperature in the range from about 120° C. to about 140° C., for about 2 hours to about 6 hours.

Compounds of formula (IIIg) could be reacted with L-$COOR^6$, L-$COR^8$, or L-$SO_2R^8$, wherein L represents leaving group such as a halogen, in the presence of a base such as triethylamine, disopropylamine, $K_2CO_3$, $Na_2CO_3$, potassium-t-butoxide, and the like, to yield a compound of formula (Ib) where $R^3$ can be $COOR^6$, $COR^8$, or $SO_2R^8$. In one aspect, suitable solvents can include dichloromethane, tetrahydrofuran, methyl t-butyl ether, and the like, and this transformation can typically be conducted at a temperature in the range of from about 0° C. to about 90° C., and for a period of time from about 4 hours to about 12 hours. The other substituents in the structures of scheme that are not specified are selected as provided herein.

In yet another aspect of this invention, compounds of formula (Ib) according to this invention, wherein $R^3$ is a heteroaryl, including a 6-membered heteroaryl, ccould be prepared as illustrated in the following scheme. The starting materials of this scheme are either commercially available or others are well known in the chemical literature and readily prepared. Representative steps are provided as follows.

Scheme 3

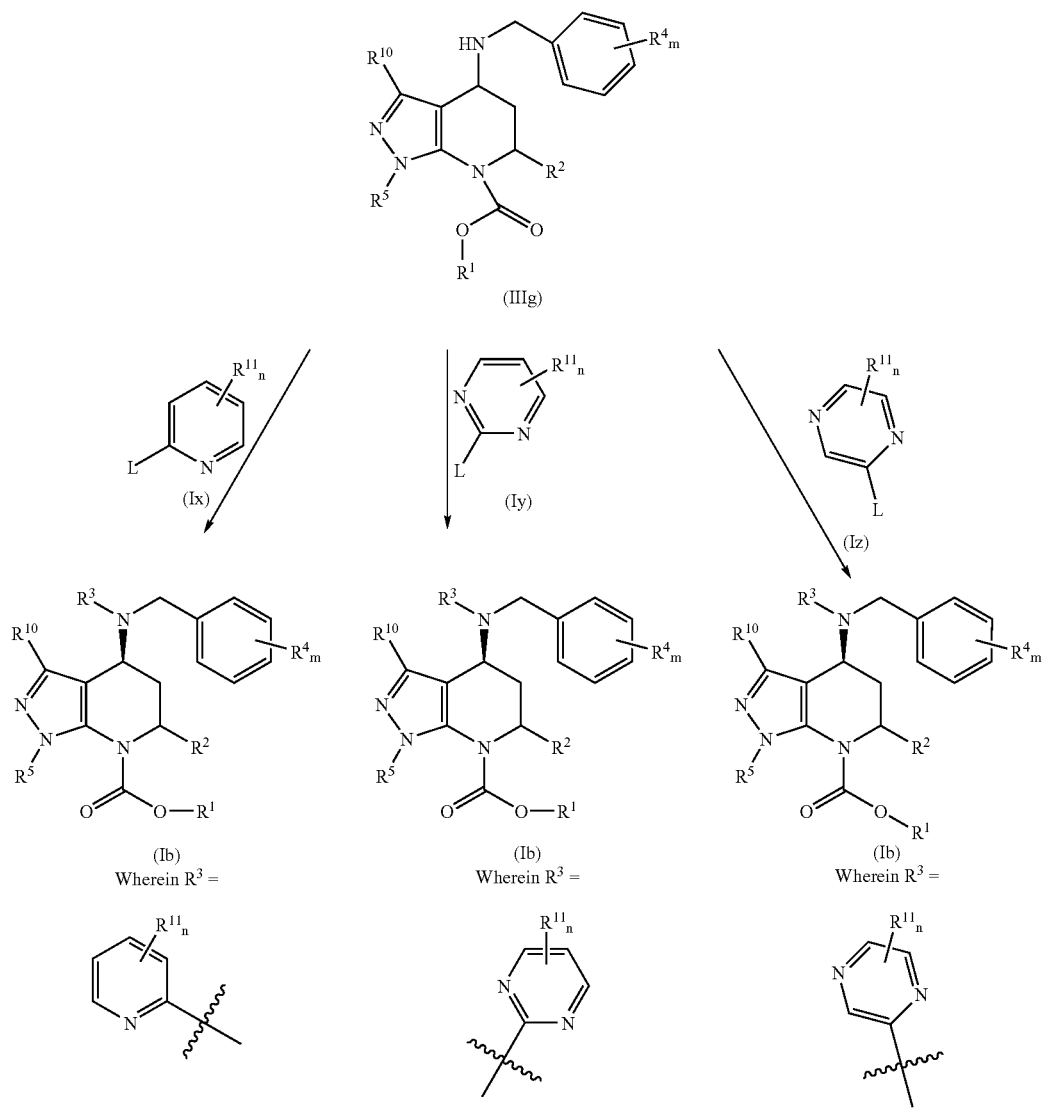

In this scheme, n can be 0, 1, 2, or 3, as the situation allows, and $R^{11}$ can be selected independently from: 1) an alkyl, a haloalkyl, a cycloalkyl, an alkoxycarbonyl, or a heterocyclyl, any of which having up to 12 carbon atoms, wherein any heterocyclyl comprises at least one heteroatom or heterogroup selected independently from >O, >N—, >S, >NR$^6$, >SO$_2$, or >CO; or 2) NR$^6$R$^7$; wherein R$^6$ and R$^7$ are independently an alkyl or a haloalkyl, any of which having up to 12 carbon atoms, or hydrogen.

Compounds of formula (IIIg) could be reacted with a compound of formula (Ix), formula (Iy), or formula (Iz), wherein L is a halogen, in presence of a base such as triethylamine, diisopropylamine, Na$_2$CO$_3$, K$_2$CO$_3$, NaH, and the like, to afford compounds of formula (Ib), wherein R$^3$ is a pyridine substituent, a pyrimidine substituent, and a pyrazine substituent, respectively. In one aspect, these reactions could be carried out at a temperature from about 15° C. to about 100° C., in a solvent such as chloroform, DMF, toluene, and the like, typically for a period of time from about 6 hours to about 25 hours.

Alternatively, compounds of formula (IIIg) could be reacted with a compound of formula (Ix), formula (Iy), or formula (Iz), wherein L is a halogen, in presence of a base such as K$_2$CO$_3$, Cs$_2$CO$_3$, and the like, to afford compounds of formula (Ib), wherein R$^3$ is a pyridine substituent, a pyrimidine substituent, and a pyrazine substituent, respectively. In one aspect, this reaction is typically carried out in presence of a Pd catalyst such as tris-(dibenzylideneacetone) dipalladium (0) [Pd$_2$(dba)$_3$], and in the presence of a ligand such as 2,2-bis-diphenyl phosphino (1,1-binapthyl) [BINAP], typically in a solvent such as toluene, DMF,1,4-dioxane, and typically at a temperature from about 50° C. to about 140° C. for a period of from about 10 hours to about 30 hours.

Yet a further aspect of this invention affords compounds of formula (Ib) according to this invention, wherein R$^3$ is imidazolyl (IIIx), oxazolyl (IIIy), thiazolyl (IIIz), or oxadiazolyl (IIIi), as illustrated in Scheme 4. The starting materials of this scheme are either commercially available or others are well known in the chemical literature and readily prepared. Representative steps are provided as follows.

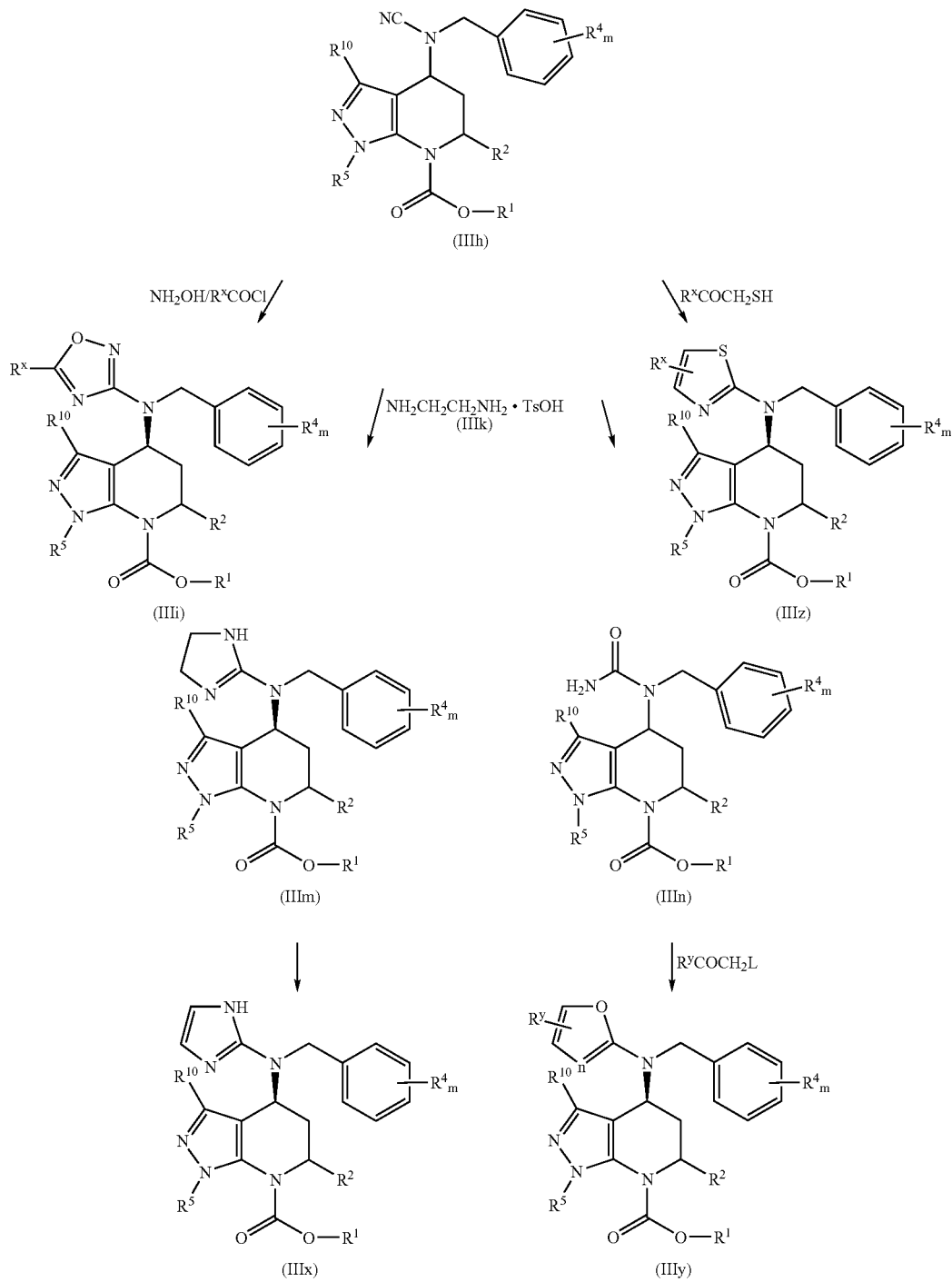

Compounds of the formula (IIIh) could be reacted with hydroxylamine in a solvent such as 1,4-dioxane or toluene, and the like, followed by the addition of R$^x$COCl wherein R$^x$ is an alkyl, and a base such as pyridine, to yield a compound of formula (IIIi).

Compounds of the formula (IIIh) could be reacted with compounds of formula (IIIk) to afford compounds of formula (IIIm). In one aspect, this reaction could be carried out at a temperature ranging from about 150° C. to about 230° C., and for a period of time from about 2 hours to about 6 hours. Further, compounds of formula (IIIm) could be dehydogenated using conventional techniques, to afford compounds of formula (IIx).

Compounds of the formula (IIIh) could be hydrolyzed in presence of a base such as KOH, NaOH, and the like, along with catalytic amount of H$_2$O$_2$, to yield a compound of formula (IIIn). In one aspect, for example, this reaction could be effected at a emperature ranging from about 25° C. to about 100° C., for about 0.5 hours to about 6 hours, or more.

Compounds of the formula (IIIn) could be reacted with a compound having the general formula R$^y$COCH$_2$L, wherein R$^y$ represents hydrogen, alkyl, L represents leaving group such as halogen, to yield a compound of formula (IIIy). In one aspect, for example, this reaction could be carried out in an alcoholic solvent, such as tert-butanol, isopropanol, and the like, typically at a temperature from about 60° C. to about 120° C.

Compounds of the formula (IIIh) could be reacted with a reagent of the formula R$^x$COCH$_2$SH, wherein R$^x$ is H or an alkyl, to yield compounds of formula (IIIz). In this aspect, for example, this reaction could be effected in a solvent such as pyridine, typically at a temperature from about 80° C. to about 120° C., and from about 8 hours to about 24 hours.

In one aspect of this invention, the compounds provided in the following table could be synthesized according to at least one of Schemes 1 through 4, as disclosed herein.

TABLE 4

Representative compounds that can be prepared according to according to at least one of Schemes 1 through 4.

| Entry | Compound |
|---|---|
| 1. | 4-[(3,5-Bis-trifluoromethyl-benzyl)-(1H-tetrazol-5-yl)-amino]-6-ethyl-1,3-dimethyl-1,4,5,6-tetrahydro-pyrazolo[3,4-b]pyridine-7-carboxylic acid ethyl ester |
| 2. | 4-[(3,5-Bis-trifluoromethyl-benzyl)-(2-methyl-2H-tetrazol-5-yl)-amino]-6-ethyl-1,3-dimethyl-1,4,5,6-tetrahydro-pyrazolo[3,4-b]pyridine-7-carboxylic acid ethyl ester |
| 3. | 4-[(3,5-Bis-trifluoromethyl-benzyl)-(1-methyl-1H-tetrazol-5-yl)-amino]-6-ethyl-1,3-dimethyl-1,4,5,6-tetrahydro-pyrazolo[3,4-b]pyridine-7-carboxylic acid ethyl ester |
| 4. | 4-[(3,5-Bis-trifluoromethyl-benzyl)-(5-methyl-[1,3,4]oxadiazol-2-yl)-amino]-6-ethyl-1,3-dimethyl-1,4,5,6-tetrahydro-pyrazolo[3,4-b]pyridine-7-carboxylic acid ethyl ester |
| 5. | 4-[(3,5-Bis-trifluoromethyl-benzyl)-(5-methyl-[1,2,4]oxadiazol-3-yl)-amino]-6-ethyl-1,3-dimethyl-1,4,5,6-tetrahydro-pyrazolo[3,4-b]pyridine-7-carboxylic acid ethyl ester |
| 6. | 4-[(3,5-Bis-trifluoromethyl-benzyl)-(2-ethyl-2H-tetrazol-5-yl)-amino]-6-ethyl-1,3-dimethyl-1,4,5,6-tetrahydro-pyrazolo[3,4-b]pyridine-7-carboxylic acid ethyl ester |
| 7. | 4-[(3,5-Bis-trifluoromethyl-benzyl)-(4-trifluoromethyl-oxazol-2-yl)-amino]-6-ethyl-1,3-dimethyl-1,4,5,6-tetrahydro-pyrazolo[3,4-b]pyridine-7-carboxylic acid ethyl ester |
| 8. | 4-[(3,5-Bis-trifluoromethyl-benzyl)-methoxycarbonyl-amino]-6-ethyl-1,3-dimethyl-1,4,5,6-tetrahydro-pyrazolo[3,4-b]pyridine-7-carboxylic acid ethyl ester |
| 9. | 4-[(3,5-Bis-trifluoromethyl-benzyl)-(2-methyl-2H-tetrazol-5-yl)-amino]-6-ethyl-1,3-dimethyl-1,4,5,6-tetrahydro-pyrazolo[3,4-b]pyridine-7-carboxylic acid ethyl ester |
| 10. | 4-[(3,5-Bis-trifluoromethyl-benzyl)-tert-butoxycarbonyl-amino]-6-ethyl-1,3-dimethyl-1,4,5,6-tetrahydro-pyrazolo[3,4-b]pyridine-7-carboxylic acid ethyl ester |
| 11. | 4-[(3,5-Bis-trifluoromethyl-benzyl)-pyrimidin-2-yl-amino]-6-ethyl-1,3-dimethyl-1,4,5,6-tetrahydro-pyrazolo[3,4-b]pyridine-7-carboxylic acid ethyl ester |
| 12. | 4-[(3,5-Bis-trifluoromethyl-benzyl)-pyridin-2-yl-amino]-6-ethyl-1,3-dimethyl-1,4,5,6-tetrahydro-pyrazolo[3,4-b]pyridine-7-carboxylic acid ethyl ester |
| 13. | 4-[(3,5-Bis-trifluoromethyl-benzyl)-(4-methyl-oxazol-2-yl)-amino]-6-ethyl-1,3-dimethyl-1,4,5,6-tetrahydro-pyrazolo[3,4-b]pyridine-7-carboxylic acid ethyl ester |
| 14. | 4-[(3,5-Bis-trifluoromethyl-benzyl)-(4-methyl-thiazol-2-yl)-amino]-6-ethyl-1,3-dimethyl-1,4,5,6-tetrahydro-pyrazolo[3,4-b]pyridine-7-carboxylic acid ethyl ester |
| 15. | 4-[(3,5-Bis-trifluoromethyl-benzyl)-(2-methyl-2H-tetrazol-5-yl)-amino]-6-ethyl-1,3-dimethyl-1,4,5,6-tetrahydro-pyrazolo[3,4-b]pyridine-7-carboxylic acid ethyl ester |
| 16. | 4-[(3,5-Bis-trifluoromethyl-benzyl)-(5-methyl-isoxazol-3-yl)-amino]-6-ethyl-1,3-dimethyl-1,4,5,6-tetrahydro-pyrazolo[3,4-b]pyridine-7-carboxylic acid ethyl ester |
| 17. | 4-[(3,5-Bis-trifluoromethyl-benzyl)-(4-ethoxycarbonyl-oxazol-2-yl)-amino]-6-ethyl-1,3-dimethyl-1,4,5,6-tetrahydro-pyrazolo[3,4-b]pyridine-7-carboxylic acid ethyl ester |
| 18. | 4-[(3,5-Bis-trifluoromethyl-benzyl)-(4-trifluoromethyl-oxazol-2-yl)-amino]-6-ethyl-1,3-dimethyl-1,4,5,6-tetrahydro-pyrazolo[3,4-b]pyridine-7-carboxylic acid ethyl ester |

In still another aspect of this invention, compounds of formula (Ia) according to this invention, could be prepared according to the following scheme. The starting materials of this scheme are either commercially available or others are well known in the chemical literature and readily prepared. Representative steps of this scheme are provided as follows.

Scheme 5

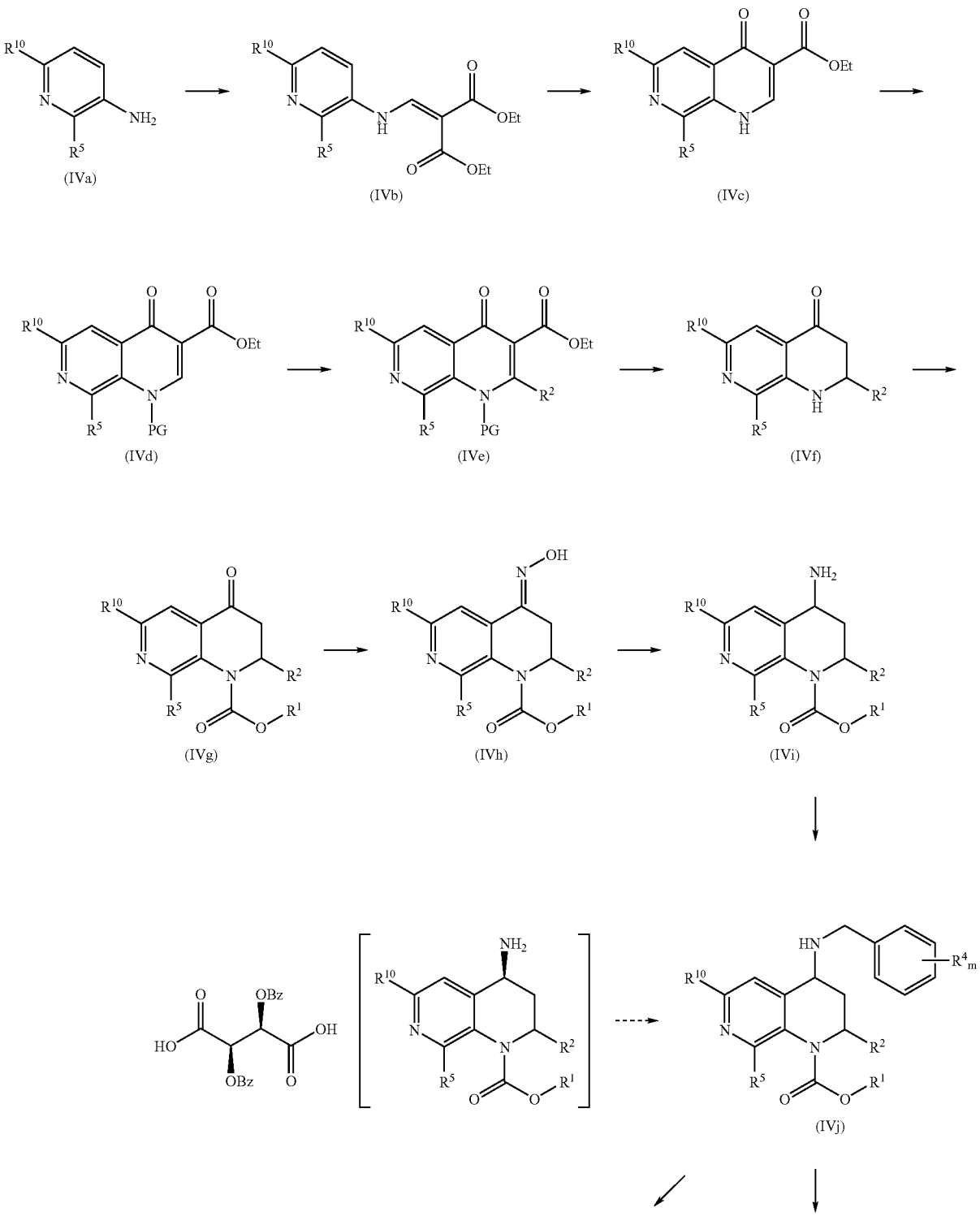

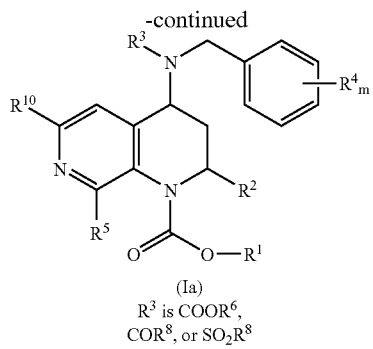

(Ia)
R³ is COOR⁶,
COR⁸, or SO₂R⁸

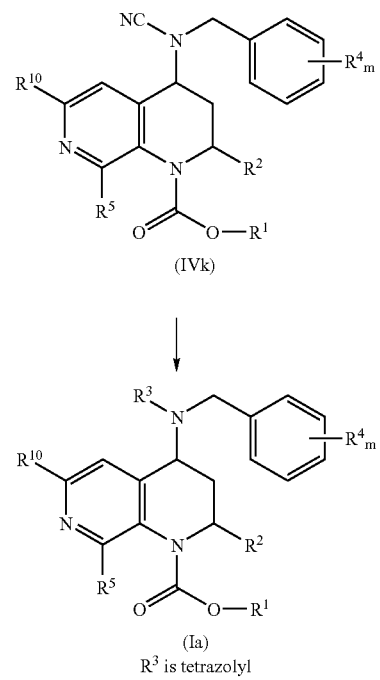

Compounds of the formula (IVb) could be prepared from substituted amino pyridines (IVa) and diethyl 2-(ethoxymethylene)malonate by heating at a temperature from about 100° C. to about 150° C. Compounds of formula (IVb) could then be converted to the cyclized products of formula (IVc) by dissolving compounds (IVb) in diphenyl ether, and heating this solution to a temperature from about 200° C. to about 220° C.

The reaction of compounds of formula (IVc) can be protected with t-butyloxycarbonyl chloride, benzyloxycarbonyl chloride or other suitable protecting groups to provide the compound of the formula (IVd), according to literature procedures (see, for example, Tetrahedron, Edition 60, 44, 2004, 10039-10048; Synthetic Communications, Edition 33, 23, 2003, 4019-4023; Synthetic Communications 34, 2004, 933-940; Journal of Organic Chemistry, Edition 69, 20, 2004, 6790-6795; Tetrahedron 2003, 59, 1895-1900; Journal of Organic Chemistry, Edition 63, 21, 1998, 7258-7262). Compounds of the formula (IVd), wherein PG is a protecting group, could be alkylated upon reaction with freshly prepared Grignard reagents (R²MgX, wherein X is a halide) or organocuprates (R²CuLi), for example, in solvents such as diethyl ether or THF, to afford compounds of the formula (IVe). In one aspect, this reaction can be carried out at temperature ranging from about −78° C. to about 0° C. Removal of the protecting group, if necessary, with acid (for example, HCl or acetic acid) or by catalytic hydrgenations, and subsequently subjecting the reaction to base (NaOH, KOH) hydrolysis or acid hydrolysis (HCl, AcOH) and decarboxylation, provides compounds of the formula (IVf).

Compounds of formula (IVg) could be prepared by an N-acylation reation using appropriately-substituted aryl or alkyl chloroformates, in presence of a base in the appropriate solvent. In one aspect, for example, these reactions could be carried out in the presence of organic bases such as pyridine, triethylamine, N-ethyldiisopropylamine, and the like, in solvents such as dichloromethane or dichloroethane. In another aspect, these reactions could be carried out in the presence of inorganic bases such as like K₂CO₃, Na₂CO₃, Cs₂CO₃, or the like, in solvents such as THF, DMF, and the like, typically at a temperature ranging from about room temperature to about 60° C.

Compounds of formula (IVi) could be prepared by converting the cyclic ketone compounds (IVg) to corresponding oxime (IVh), by reacting (IVg) with hydroxylamine hydrochloride in presence of an organic base such as pyridine, typically in a solvent such as THF and the like. Amine compounds of the formula (IVi) could be prepared by the catalytic reduction of the oxime (IVh) to the corresponding amine using a Pd/C- and/or Raney-Ni-catalyzed reduction, or in another aspect, by reduction with Zn/Fe and acetic acid. The amine (IVi) could be resolved to its optically pure forms by making its (−)-dibenzoyl-L-tartaric acid salt and thereafter by cleaving it with a base (NaOH) treatment.

The conversion of compounds of formula (IVi) to compounds (IVj) could be performed through direct reductive amination with an appropriately-substituted arylamine, in presence of acetic acid and a reducing agent like NaCNBH₃. In one aspect, this reaction could be carried out in a chlorinated or alcohol solvents such as MeOH, dichloromethane, and the like, typically at room temperature.

Compounds of formula (IVj) could be reacted with cyanogen bromide (NCBr), in the presence of a base such as NaHCO₃, Na₂CO₃, KHCO₃, K₂CO₃, and the like, to yield compounds of formula (IVk). In one aspect, for example, this reaction could be carried out at a temperature from about 15° C. to about 50° C., in an alcohol, a chlorinated, an ether, an ester, or a combination of these solvents. For example, a solvent such as methanol, ethanol, chloroform, diethylether, N,N-dimethylformamide (DMF), ethyl acetate, and the like, is appropriate for this reaction, which is typically carried out from about 2 hours to about 8 hours.

Compounds of formula (IVk) could be reacted with sodium azide (NaN₃) in presence of an ammonium halide such as ammonium chloride in solvents such as N,N-dimethylformamide (DMF), to yield compounds of formula (Ia), wherein $R^3$ can be tetrazolyl. The tetrazolyl moiety $R^3$ shown in this scheme can be readily substituted with, or converted to, a substituted tetrazole $R^3$. In one aspect, this reaction can typically be carried out in solvents such as N,N-dimethylformamide (DMF) or THF, typically at temperatures from about room temperature to about 120° C., for a duration from about 2 hours to about 18 hours.

Compounds of formula (Ia), wherein $R^3$ is tetrazolyl, can be converted to a compound of formula (Ia) wherein $R^3$ is a [1,2,4]oxadiazolyl, upon reacting the tetrazolyl-substituted compound (Ia) with an acid chloride. This reaction could be carried out in the presence of an appropriate solvent such as pyridine, typically at a temperature from about 120° C. to about 140° C., and for a time period ranging from about 2 to about 6 hours.

Compounds of formula (IVj) could be reacted with L-COOR$^6$, L-COR$^8$, or L-SO$_2$R$^8$, wherein L represents leaving group such as a halogen, in the presence of a base such as triethylamine, disopropylamine, $K_2CO_3$, $Na_2CO_3$, potassium-t-butoxide, and the like, to yield a compound of formula (Ib) where $R^3$ can be COOR$^6$, COR$^8$, or SO$_2$R$^8$. In one aspect, suitable solvents can include dichloromethane, tetrahydrofuran, methyl t-butyl ether, and the like, and this transformation can typically be conducted at a temperature in the range of from about 0° C. to about 90° C., and for a period of time from about 4 hours to about 12 hours. The other substitutents in the structures of scheme that are not specified are selected as provided herein.

Yet another aspect of this disclosure affords compounds of formula (Ia), according to this invention, wherein $R^3$ is a heteroaryl, including a 6-membered heteroaryl, which could be prepared as illustrated in the following scheme. The starting materials of this scheme are either commercially available or others are well known in the chemical literature and readily prepared. Representative steps of this scheme are provided as follows.

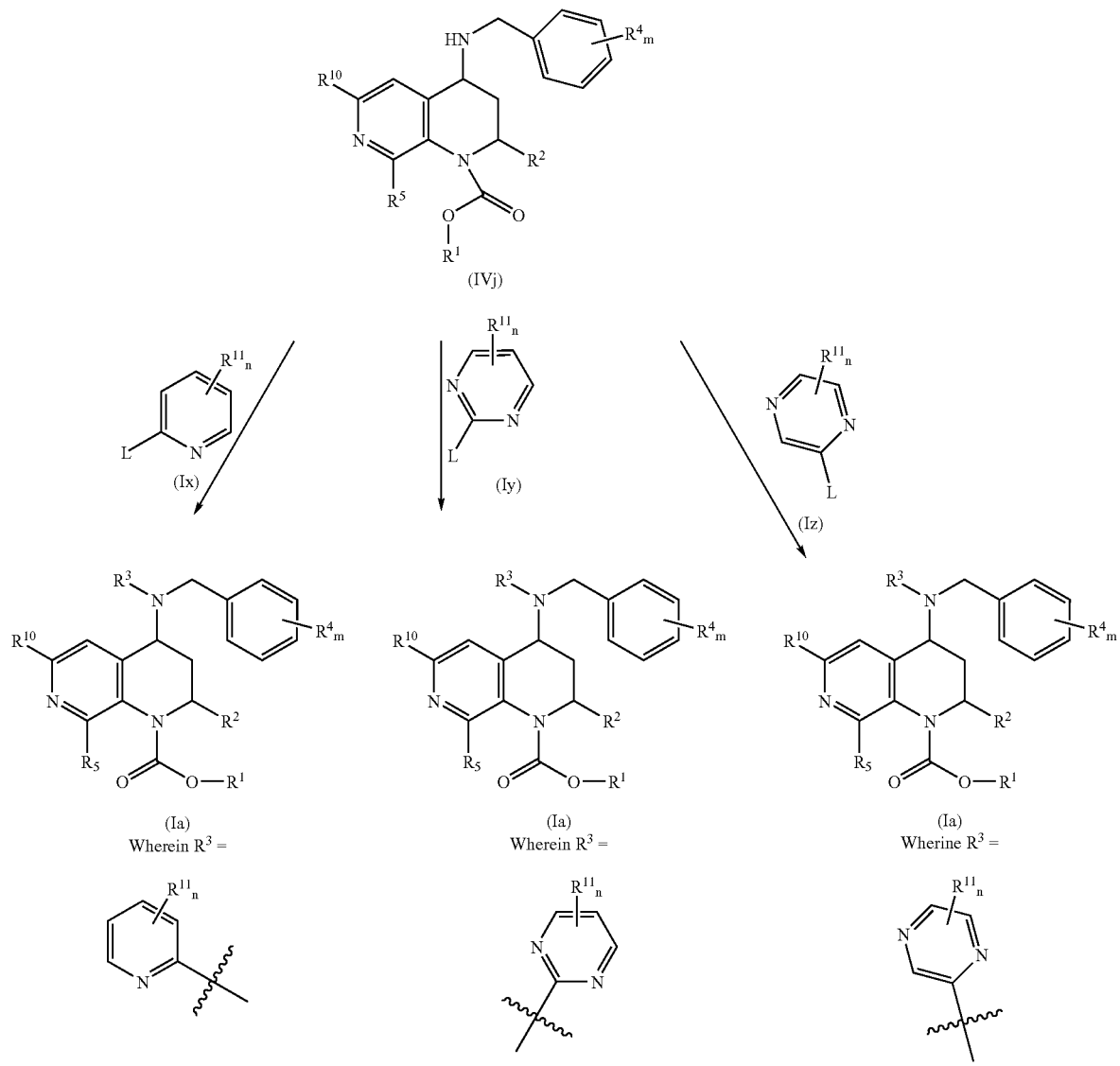

In this scheme, n can be 0, 1, 2, or 3, as the situation allows, and $R^{11}$ can be selected independently from: 1) an alkyl, a haloalkyl, a cycloalkyl, an alkoxycarbonyl, or a heterocyclyl, any of which having up to 12 carbon atoms, wherein any heterocyclyl comprises at least one heteroatom or heterogroup selected independently from >O, >N—, >S, >$NR^6$, >$SO_2$, or >CO; or 2) $NR^6R^7$; wherein $R^6$ and $R^7$ are independently an alkyl or a haloalkyl, any of which having up to 12 carbon atoms, or hydrogen.

Compounds of formula (IVj) could be reacted with a compound of formula (Ix), formula (Iy), or formula (Iz), wherein L is a halogen, in presence of a base such as triethylamine, diisopropylamine, $Na_2CO_3$, $K_2CO_3$, NaH, and the like, to afford compounds of formula (Ia), wherein $R^3$ is a pyridine substituent, a pyrimidine substituent, and a pyrazine substituent, respectively. In one aspect, these reactions could be carried out at a temperature from about 15° C. to about 100° C., in a solvent such as chloroform, DMF, toluene, and the like, typically for a period of time from about 6 hours to about 25 hours.

Alternatively, compounds of formula (IVj) could be reacted with a compound of formula (Ix), formula (Iy), or formula (Iz), wherein L is a halogen, in presence of a base such as $K_2CO_3$, $Cs_2CO_3$, and the like, to afford compounds of formula (Ia), wherein $R^3$ is a pyridine substituent, a pyrimidine substituent, and a pyrazine substituent, respectively. In one aspect, this reaction is typically carried out in presence of a Pd catalyst such as tris-(dibenzylideneacetone) dipalladium (0) [$Pd_2(dba)_3$], and in the presence of a ligand such as 2,2-bis-diphenyl phosphino (1,1-binapthyl) [BINAP], typically in a solvent such as toluene, DMF, 1,4-dioxane, and typically at a temperature from about 50° C. to about 140° C. for a period of from about 10 hours to about 30 hours.

Yet a further aspect of this invention affords compounds of formula (Ia) according to this invention, wherein $R^3$ is imidazolyl (IVx), oxazolyl (IVy), thiazolyl (IVz), or oxadiazolyl (IVv), as illustrated in the following scheme. The starting materials of this scheme are either commercially available or others are well known in the chemical literature and readily prepared. Representative steps are provided as follows.

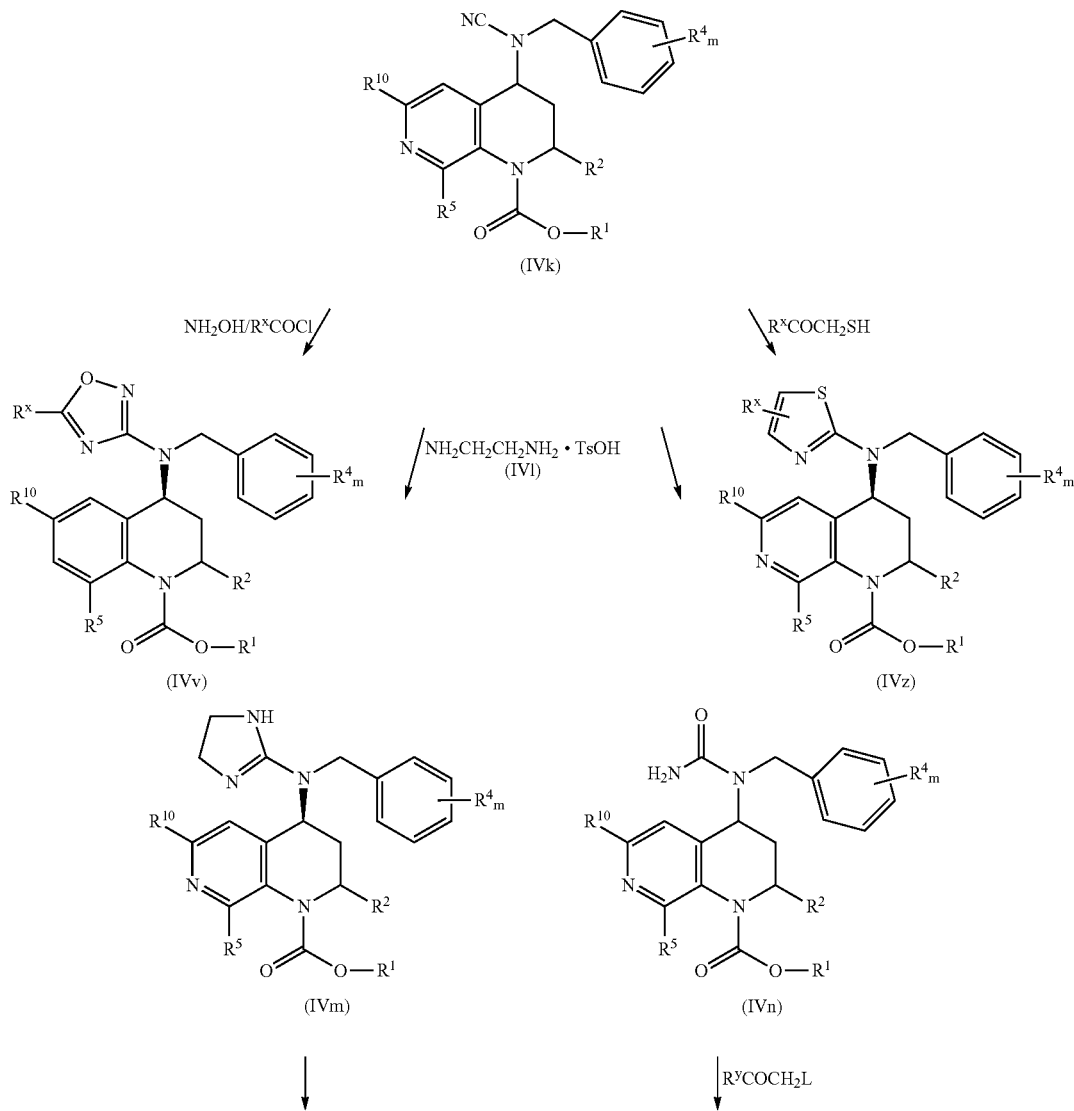

Scheme 7

-continued

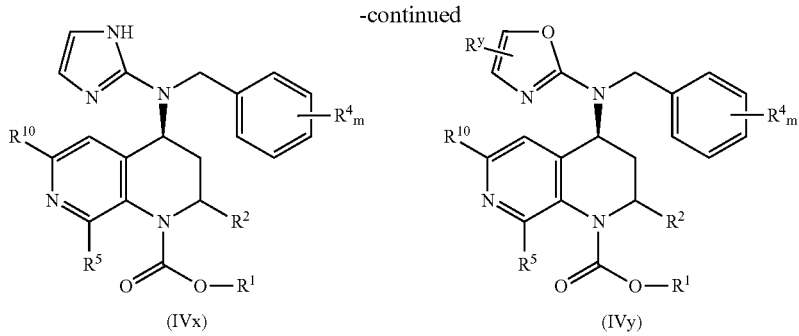

(IVx)    (IVy)

Compounds of the formula (IVk) could be reacted with hydroxylamine in a solvent such as 1,4-dioxane or toluene, and the like, followed by the addition of R$^x$COCl wherein R$^x$ is an alkyl, and a base such as pyridine, to yield a compound of formula (IVv).

Compounds of the formula (IVk) could be reacted with compounds of formula (IVl) to afford compounds of formula (IVm). In one aspect, this reaction could be carried out at a temperature ranging from about 150° C. to about 230° C., and for a period of time from about 2 hours to about 6 hours. Further, compounds of formula (IVm) could be dehydogenated using conventional techniques, to afford compounds of formula (IVx).

Compounds of the formula (IVk) could be hydrolyzed in presence of a base such as KOH, NaOH, and the like, along with catalytic amount of H$_2$O$_2$, to yield a compound of formula (IVn). In one aspect, for example, this reaction could be effected at a emperature ranging from about 25° C. to about 100° C., for about 0.5 hours to about 6 hours, or more.

Compounds of the formula (IVn) could be reacted with a compound having the general formula R$^y$COCH$_2$L, wherein R$^y$ represents hydrogen, alkyl, L represents leaving group such as halogen, to yield a compound of formula (IVy). In one aspect, for example, this reaction could be carried out in an alcoholic solvent, such as tert-butanol, isopropanol, and the like, typically at a temperature from about 60° C. to about 120° C.

Compounds of the formula (IVk) could be reacted with a reagent of the formula R$^x$COCH$_2$SH, wherein R$^x$ is H or an alkyl, to yield compounds of formula (IVz). In this aspect, for example, this reaction could be effected in a solvent such as pyridine, typically at a temperature from about 80° C. to about 120° C., and from about 8 hours to about 24 hours.

Another aspect of this invention affords compounds of the formula:

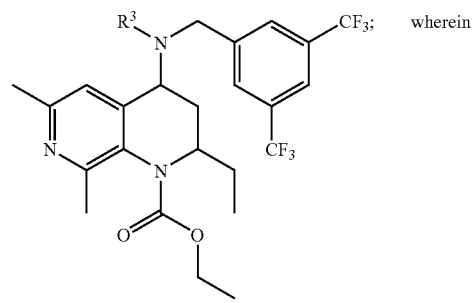

wherein

R$^3$ can be selected from

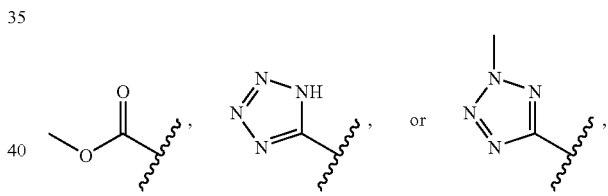

as illustrated in the following scheme, which starts from 3-amino-2,6-dimethylpyridine. Further to this scheme, differently-substituted analogs of the compounds illustrated can be prepared by, for example, employing substituted analogs of the R$^3$ substituents in the syntheses shown. In one aspect, the reagents and general conditions by which these compounds could be prepared are disclosed in the scheme.

Scheme 8

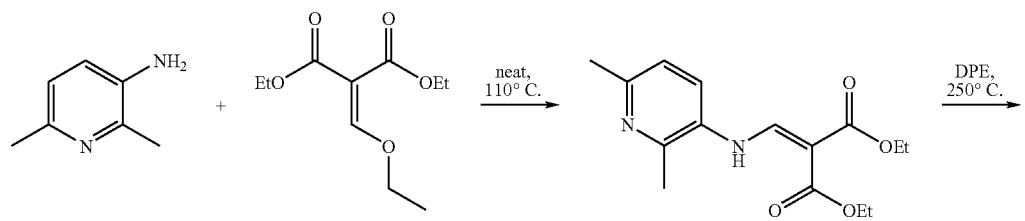

-continued
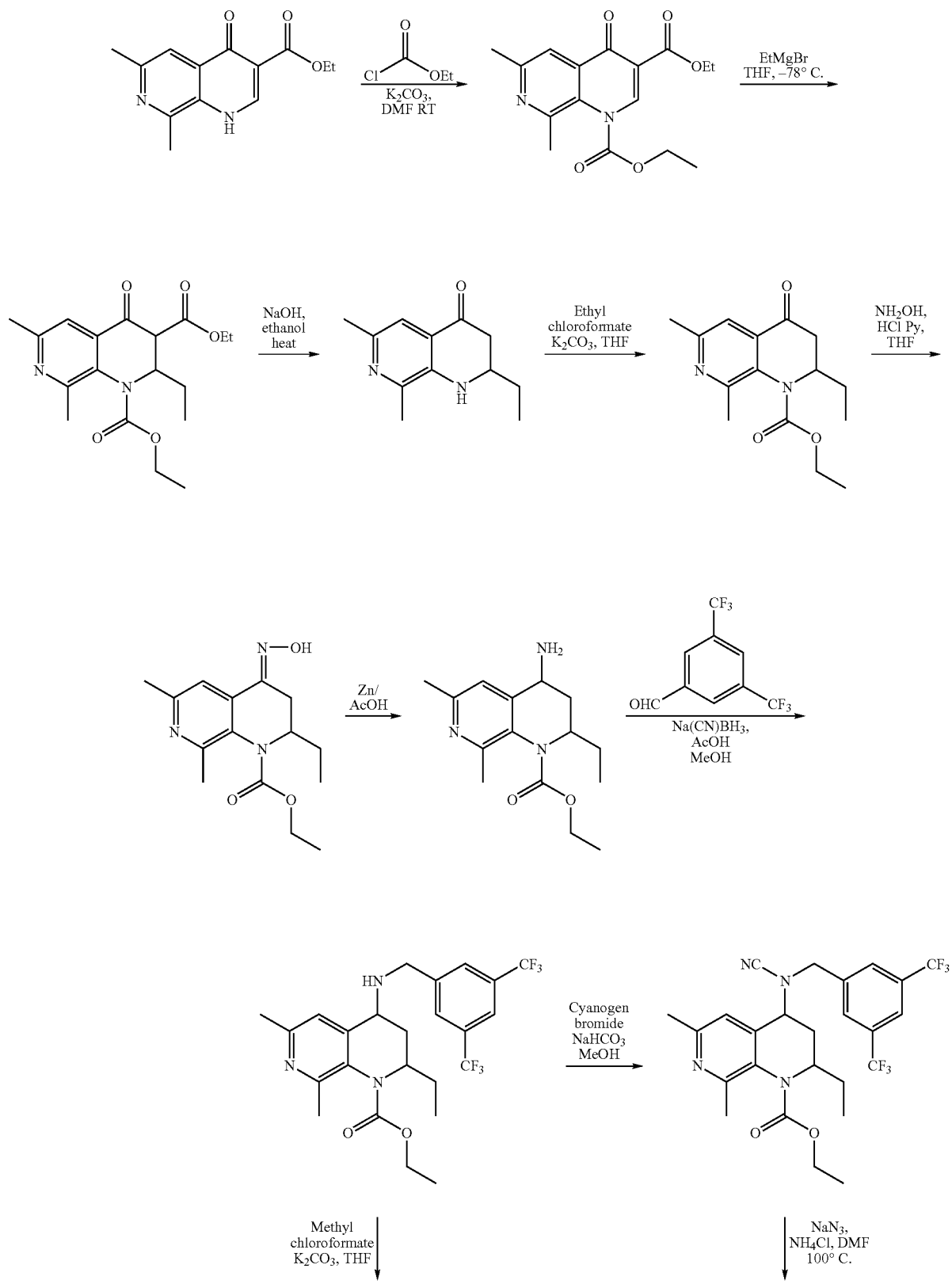

-continued

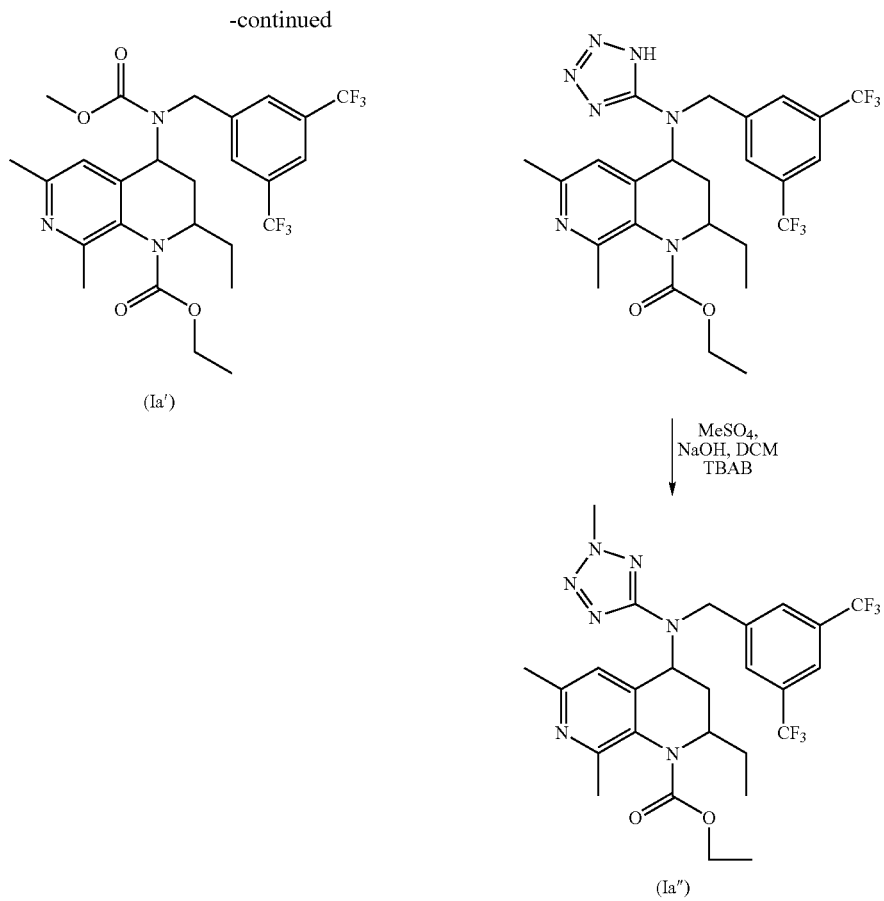

Compounds of formula (Ia') can be prepared, for example, from a compound of formula (IVa), wherein $R^5$ and $R^{10}$ are methyl, according to Scheme 8, by following the methodology as provided in Scheme 5.

Compounds of formula (Ia'') can be prepared, for example, from a compound of formula (IVa), wherein $R^5$ and $R^{10}$ are methyl, according to Scheme 8, by following methodology as provided in Scheme 5.

In one aspect of this invention, the compounds provided in the following table could be synthesized according to at least one of Schemes 1 and 5-8, as disclosed herein.

TABLE 5

Representative compounds that can be prepared according to according to at least one of Schemes 1, 5, 6, 7, or 8.

| Entry | Compound |
|---|---|
| 1. | 4-[(3,5-Bis-trifluoromethyl-benzyl)-(1H-tetrazol-5-yl)-amino]-2-ethyl-6,8-dimethyl-3,4-dihydro-2H-[1,7]naphthyridine-1-carboxylic acid ethylester |
| 2. | 4-[(3,5-Bis-trifluoromethyl-benzyl)-(2-methyl-2H-tetrazol-5-yl)-amino]-2-ethyl-6,8-dimethyl-3,4-dihydro-2H-[1,7]naphthyridine-1-carboxylic acid ethyl ester |
| 3. | 4-[(3,5-Bis-trifluoromethyl-benzyl)-(1-methyl-1H-tetrazol-5-yl)-amino]-2-ethyl-6,8-dimethyl-3,4-dihydro-2H-[1,7]naphthyridine-1-carboxylic acid ethyl ester |
| 4. | 4-[(3,5-Bis-trifluoromethyl-benzyl)-(5-methyl-[1,3,4]oxadiazol-2-yl)-amino]-2-ethyl-6,8-dimethyl-3,4-dihydro-2H-[1,7]naphthyridine-1-carboxylic acid ethyl ester |
| 5. | 4-[(3,5-Bis-trifluoromethyl-benzyl)-(5-methyl-[1,2,4]oxadiazol-3-yl)-amino]-2-ethyl-6,8-dimethyl-3,4-dihydro-2H-[1,7]naphthyridine-1-carboxylic acid ethyl ester |
| 6. | 4-[(3,5-Bis-trifluoromethyl-benzyl)-(2-ethyl-2H-tetrazol-5-yl)-amino]-2-ethyl-6,8-dimethyl-3,4-dihydro-2H-[1,7]naphthyridine-1-carboxylic acid ethyl ester |
| 7. | 4-[(3,5-Bis-trifluoromethyl-benzyl)-(4-trifluoromethyl-oxazol-2-yl)-amino]-2-ethyl-6,8-dimethyl-3,4-dihydro-2H-[1,7]naphthyridine-1-carboxylic acid ethyl ester |

TABLE 5-continued

Representative compounds that can be prepared according to according to at least one of Schemes 1, 5, 6, 7, or 8.

Entry Compound 8. 4-[(3,5-Bis-trifluoromethyl-benzyl)-methoxycarbonyl-amino]-2-ethyl-6,8-dimethyl-3,4-dihydro-2H-[1,7]naphthyridine-1-carboxylic acid ethyl ester
9. 4-[(3,5-Bis-trifluoromethyl-benzyl)-(2-methyl-2H-tetrazol-5-yl)-amino]-2-ethyl-6,8-dimethyl-3,4-dihydro-2H-[1,7]naphthyridine-1-carboxylic acid ethyl ester
10. 4-[(3,5-Bis-trifluoromethyl-benzyl)-tert-butoxycarbonyl-amino]-2-ethyl-6,8-dimethyl-3,4-dihydro-2H-[1,7]naphthyridine-1-carboxylic acid ethyl ester
11. 4-[(3,5-Bis-trifluoromethyl-benzyl)-pyrimidin-2-yl-amino]-2-ethyl-6,8-dimethyl-3,4-dihydro-2H-[1,7]naphthyridine-1-carboxylic acid ethyl ester
12. 4-[(3,5-Bis-trifluoromethyl-benzyl)-pyridin-2-yl-amino]-2-ethyl-6,8-dimethyl-3,4-dihydro-2H-[1,7]naphthyridine-1-carboxylic acid ethyl ester
13. 4-[(3,5-Bis-trifluoromethyl-benzyl)-(4-methyl-oxazol-2-yl)-amino]-2-ethyl-6,8-dimethyl-3,4-dihydro-2H-[1,7]naphthyridine-1-carboxylic acid ethyl ester
14. 4-[(3,5-Bis-trifluoromethyl-benzyl)-(4-methyl-thiazol-2-yl)-amino]-2-ethyl-6,8-dimethyl-3,4-dihydro-2H-[1,7]naphthyridine-1-carboxylic acid ethyl ester
15. 4-[(3,5-Bis-trifluoromethyl-benzyl)-(2-methyl-2H-tetrazol-5-yl)-amino]-2-ethyl-6,8-dimethyl-3,4-dihydro-2H-[1,7]naphthyridine-1-carboxylic acid ethyl ester
16. 4-[(3,5-Bis-trifluoromethyl-benzyl)-(5-methyl-isoxazol-3-yl)-amino]-2-ethyl-6,8-dimethyl-3,4-dihydro-2H-[1,7]naphthyridine-1-carboxylic acid ethyl ester
17. 4-[(3,5-Bis-trifluoromethyl-benzyl)-(4-ethoxycarbonyl-oxazol-2-yl)-amino]-2-ethyl-6,8-dimethyl-3,4-dihydro-2H-[1,7]naphthyridine-1-carboxylic acid ethyl ester
18. 4-[(3,5-Bis-trifluoromethyl-benzyl)-(4-trifluoromethyl-oxazol-2-yl)-amino]-2-ethyl-6,8-dimethyl-3,4-dihydro-2H-[1,7]naphthyridine-1-carboxylic acid ethyl ester
19. 4-[(3,5-Bis-trifluoromethyl-benzyl)-(4-trifluoromethyl-oxazol-2-yl)-amino]-2-ethyl-6,8-dimethoxy-3,4-dihydro-2H-[1,7]naphthyridine-1-carboxylic acid ethyl ester
20. 4-[(3,5-Bis-trifluoromethyl-benzyl)-(4-ethoxycarbonyl-oxazol-2-yl)-amino]-2-ethyl-6,8-dimethoxy-3,4-dihydro-2H-[1,7]naphthyridine-1-carboxylic acid ethyl ester
21. 4-[(3,5-Bis-trifluoromethyl-benzyl)-(5-methyl-isoxazol-3-yl)-amino]-2-ethyl-6,8-dimethoxy-3,4-dihydro-2H-[1,7]naphthyridine-1-carboxylic acid ethyl ester Methods of Treating Diseases Compounds disclosed herein to control CETP activity can be used for preventing or treating a variety of conditions or diseases such as ones associated with lipoprotein metabolism. Without being held to a particular theory, it is believed that CETP activity can affect the level of circulating cholesterol-containing HDL. Increased CETP can produce a decrease in HDL-C levels relative to LDL-C and/or VLDL-C levels. For example, CETP plays a role in transferring cholesteryl ester from HDL to VLDL and LDL, and thereby in altering the relative profile of circulating lipoproteins to one which is associated with an increased risk of cardiovascular disease (for example, decreased levels of HDL-C and increased levels of VLDL-C and LDL-C). Further, increased levels of CETP activity can be predictive of increased risk of cardiovascular disease. Modulation or inhibition of CETP activity, therefore, can be a prophylactic or therapeutic method for modulating the relative levels of lipoproteins to reduce or prevent the progression of, to induce regression of, or reduce risk of development of a variety of conditions or diseases including cardiovascular diseases, such as atherosclerosis.

Effective amounts are administered to the subject in dosages and formulations that are safe and effective, including, but not limited to, the ranges taught herein. As disclosed herein, compositions comprising at least one compound having a formula as disclosed herein, and/or their pharmaceutically-acceptable salts, can be used in conjunction with other prophylactic or therapeutic agents or in methods optionally comprising steps such as altered patient activities, including, but not limited to, changes in exercise or diet.

In one aspect, the present invention provides a method of treating or preventing a condition or disease in a mammalian subject, the method comprising administering to the subject a composition comprising a prophylactically- or therapeutically-effective amount of at least one compound having a formula as disclosed herein, and/or their pharmaceutically-acceptable salts. In various aspects, the condition or disease is dyslipidemia, atherosclerosis, a peripheral vascular disease, hypertryglyceridemia, hypercholesterolemia, hyperbetalipoproteinemia, hypoalphalipoprotenemia, a cardiovascular disorder (for example, angina, ischemia, stroke, myocardial infarction (MI), reperfusion injury, restenosis, hypertension) or diabetic vascular diseases (for example, diabetic retinopathy, endotoxemia).

In some aspects, the present invention provides a method of decreasing or inhibiting CETP activity in a mammalian subject, the method comprising administering to the subject an amount of a composition comprising at least one compound having a formula as disclosed herein, and/or their pharmaceutically-acceptable salts, wherein the amount is sufficient to decrease or inhibit CETP activity in the subject.

In other aspects, the present invention provides a method of increasing high density lipoprotein (HDL) in a mammalian subject, the method comprising administering to the subject an amount of a composition comprising at least one compound having a formula as disclosed herein, and/or their pharmaceutically-acceptable salts, wherein the amount is sufficient to increase high density lipoprotein (HDL) in the subject.

In some aspects, the present invention provides a method of elevating the ratio of circulating HDL to circulating LDL, VLDL, or total cholesterol in a mammalian subject, the method comprising administering to the subject a prophylactically- or therapeutically-effective amount of at least one compound having a formula as disclosed herein, and/or their pharmaceutically-acceptable salts.

In other aspects, the present invention provides a method of altering catabolism of HDL-cholesterol to decrease development of atherosclerotic lesions in a mammalian subject, the method comprising administering to the subject an amount of a composition comprising at least one compound having a formula as disclosed herein, and/or their pharmaceutically-acceptable salts, wherein the amount is sufficient to alter the catabolism of HDL-cholesterol thereby leading to decreased development of atherosclerotic lesions.

In some aspects, the present invention provides a method of decreasing low density lipoprotein (LDL) in a mammalian subject, the method comprising administering to the subject an amount of a composition comprising at least one compound having a formula as disclosed herein, and/or their pharmaceutically-acceptable salts, wherein the amount is sufficient to decrease low density lipoprotein (LDL).

In other aspects, the present invention provides a method of treating or preventing atherosclerosis in a mammalian subject, the method comprising administering to the subject a prophylactically- or therapeutically-effective amount of at least one compound having a formula as disclosed herein, and/or their pharmaceutically-acceptable salts.

In some aspects, the present invention provides a method of treating or preventing hyperlipidemia in a mammalian subject, the method comprising administering to the subject a prophylactically- or therapeutically-effective amount of at least one compound having a formula as disclosed herein, and/or their pharmaceutically-acceptable salts.

In various other aspects, the present invention provides a method of treating or preventing a CETP-mediated disorder in a mammalian subject, the method comprising administering to the subject a prophylactically- or therapeutically-effective amount of at least one compound having a formula as disclosed herein, and/or their pharmaceutically-acceptable salts.

In yet another aspect, the present invention provides a method of treating or preventing dyslipidemia, atherosclerosis, a peripheral vascular disease, hypertryglyceridemia, hypercholesterolemia, hyperbetalipoproteinemia, hypoalphalipoproteinemia, a cardiovascular disorder, a diabetic vascular disease, or endotoxemia. In one aspect, the cardiovascular disorder is angina, ischemia, stroke, myocardial infarction (MI), reperfusion injury, restenosis or hypertension.

The compounds of the present invention are useful in the treatment and/or prophylaxis of the above said diseases in combination/concomittant with one or more LDL-cholesterol lowering agents such as HMG CoA reductase inhibitors; cholesterol absorption inhibitors; antiobesity drugs; lipoprotein disorder treatment drugs; hypoglycemic agents: insulin; biguanides; sulfonylureas; thiazolidinediones; dual PPAR agonists; and/or mixtures thereof. The compounds of the present invention in combination with HMG CoA reductase inhibitors, microsomal triglyceride transfer protein (MTP)/ApoB secretion inhibitors, cholesterol absorption inhibitors, antiobesity drugs, hypoglycemic agents can be administered together or within in such a period of time so as to act synergistically.

In one aspect, the present invention provides a prophylactic or therapeutic composition comprising at least one compound having a formula as disclosed herein, and/or their pharmaceutically-acceptable salts and, optionally an antihypertensive agent. Hypertension can be characterized as persistently high blood pressure. Illustratively, an adult having a systolic blood pressure that is persistently at least about 140 mmHg or a diastolic blood pressure that is at least about 90 mmHg can be classified as hypertensive. Hyperlipidemic conditions such as atherosclerosis can have an affect on hypertension.

The dosage regimen utilizing, the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, counter or arrest the progress of the condition.

Compounds and compositions of the present invention can be administered by any appropriate route, including, for example, orally, parenterally, intravenously, intradermally, intramuscularly, subcutaneously, sublingually, transdermally, bronchially, pharyngolaryngeal, intranasally, topically such as by a cream or ointment, rectally, intraarticular, intracisternally, intrathecally, intravaginally, intraperitoneally, intraocularly, by inhalation, bucally or as an oral or nasal spray.

Oral dosages of compositions of the present invention, when used for the indicated effects, will range from about 0.01 mg per kg of body weight per day (mg/kg/day) to about 100 mg/kg/day. Advantageously, compounds of the present invention can be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be substantially continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or betalactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

Pharmaceutical Compositions

In one aspect, the present invention provides a composition comprising at least one compound as disclosed herein.

In another aspect, this invention provides a pharmaceutical composition, comprising:

at least one compound as disclosed herein; and optionally comprising a pharmaceutically acceptable additive selected from a carrier, an auxiliary, a diluent, an excipient, a preservative, a solvate, or any combination thereof.

In yet another aspect, this invention provides a pharmaceutical composition, comprising:

at least one compound as disclosed herein; and optionally comprising a pharmaceutically acceptable additive selected from a carrier, an auxiliary, a diluent, an excipient, a preservative, a solvate, or any combination thereof;

wherein the pharmaceutical composition is in the form of a tablet, a capsule, a syrup, a cachet, a powder, a granule, a solution, a suspension, an emulsion, a bolus, a lozenge, a suppository, a cream, a gel, a paste, a foam, a spray, an aerosol, a microcapsule, a liposome, or a transdermal patch.

In still another aspect, this invention provides a pharmaceutical composition, comprising:

at least one compound as disclosed herein;

optionally comprising a pharmaceutically acceptable additive selected from a carrier, an auxiliary, a diluent, an excipient, a preservative, a solvate, or any combination thereof; and further comprising an agent selected from a chemotherapeutic agent, an immunosuppressive agent, a cytokine, a cytotoxic agent, an anti-inflammatory agent, an antirheumatic agent, an antidyspilidemic agent, a cardiovascular agent, or any combination thereof.

Accordingly, in addition to the compounds disclosed herein, the pharmaceutical compositions of the present invention can further comprise at least one of any suitable auxiliary such as, but not limited to, diluent, binder, stabilizer, buffers, salts, lipophilic solvents, preservative, adjuvant, or the like. In one aspect of the present invention, pharmaceutically acceptable auxiliaries are employed. Examples and methods of preparing such sterile solutions are well known in the art and can be found in well known texts such as, but not limited to, REMINGTON'S PHARMACEUTICAL SCIENCES (Gennaro, Ed., 18th Edition, Mack Publishing Co. (1990)). Pharmaceutically acceptable carriers can be routinely selected that are suitable for the mode of administration, solubility and/or stability of the compound.

Pharmaceutical Compositions for Oral Administration

For oral administration in the form of a tablet or capsule, a compound can be combined with an oral, non-toxic pharmaceutically acceptable inert carrier such as ethanol, glycerol, water, and the like. Moreover, when desired or necessary, suitable binders, lubricants, disintegrating agents, and coloring agents may also be incorporated into the mixture. Suitable binders include, without limitation, starch; gelatin; natural sugars such as glucose or beta-lactose; corn sweeteners; natural and synthetic gums such as acacia, tragacanth, or sodium alginate, carboxymethylcellulose; polyethylene glycol; waxes; and the like. Lubricants used in these dosage forms include, without limitation, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The pharmaceutical preparations contain at least one compound of the present invention represented by any formula disclosed herein, and/or a pharmaceutically acceptable salt thereof, in an amount effective to inhibit CETP activity and prevent or treat the various conditions or diseases attributable to CETP activity. One skilled in the art can easily determine such an effective amount. The preparations optionally can contain other ingredients including, for example, an antihypertensive drug.

Formulations of the present invention suitable for oral administration can be presented as discrete units such as capsules, cachets, or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, and the like.

Routes of Administration

The invention further relates to the administration of at least one compound disclosed herein by the following routes, including, but not limited to oral, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, iontophoretic means, or transdermal means.

Dosages

A composition comprising at least one compound of the present invention can be administered at a frequency and for a period of time effective to achieve a therapeutic effect, which should be understood in the context of a regimen of repeated administration at such a frequency and over such a period. In some aspects, a composition is administered at a frequency and for a period of time effective to increase a HSPG expression. In some aspects, a composition can be administered in a single daily dose, or a total daily dosage can be administered in divided doses of two, three, or four times daily. Typically and most conveniently, a composition is administered at least once daily, but in certain situations less frequent, for example, twice weekly or weekly, administration can be effective. For greatest benefit, administration should continue for a prolonged period, for example at least about 3 months, or at least about 6 months, or at least about 1 year, or at least about 2 years, or at least about 3 years. In one aspect, administration continues from a time of initiation for substantially the remainder of the mammal's life.

The selection and/or amounts of individual compounds can, if desired vary over the period of administration. In one aspect, a single composition of this invention is administered to a mammal for the entire period of administration. In other aspects, different compositions comprising at least one compound are administered to the mammal at different times.

The dosages of compounds can be adjusted on a per body weight basis and may thus be suitable for any subject regardless of the subject's size.

In one aspect of this invention, daily oral dose comprises a total compound amount of at least about 0.0001 mg per kg body weight, illustratively about 0.0001 mg to about 1000 mg, about 0.001 mg to about 100 mg, about 0.01 mg to about 10 mg, about 0.1 mg to about 5 mg, or about 1 to about 3 mg per kg body weight.

In another aspect, a daily intravenous injection comprises a total compound amount of at least about 0.0001 mg per kg body weight, illustratively about 0.0001 mg to about 0.5 mg, about 0.001 mg to about 0.25, or about 0.01 to about 0.03 mg per kg body weight.

Illustratively, a tablet for oral administration can be manufactured to comprise a total compound amount of about 0.001 mg, about 0.1 mg, about 0.2 mg, about 0.5 mg, about 1 mg, about 2 mg, about 5 mg, about 10 mg, about 15 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 800 mg, about 900 mg, or about 1000 mg.

In one aspect, a composition comprises an active ingredient content of at least about 0.01% by weight of the composition, illustratively about 0.01% to about 99%, about 0.05% to about 90%, about 0.1% to about 80%, about 0.5% to about 50% by weight of the composition. The amount of active ingredient that can be combined with other materials to produce a single dosage form varies depending upon the subject treated and the particular mode of administration.

An effective amount of the drug is ordinarily supplied at a dosage level of from about 0.1 mg/kg to about 20 mg/kg of body weight per day. In one aspect, the range is from about 0.2 mg/kg to about 10 mg/kg of body weight per day. In another aspect, the range is from about 0.5 mg/kg to about 10 mg/kg of body weight per day. The compounds can be administered on a regimen of about 1 to about 10 times per day.

Co-administration or sequential administration of the compounds of the present invention and other therapeutic agents can be employed, such as chemotherapeutic agents, immunosuppressive agents, cytokines, cytotoxic agents, nucleolytic compounds, radioactive isotopes, receptors, and pro-drug activating enzymes, which can be naturally occurring or produced by recombinant methods. The combined administration includes co-administration, using separate formulations or a single pharmaceutical formulation, and consecutive administration in either order, wherein preferably there is a time period while both (or all) active therapeutic agents simultaneously exert their biological activities.

It is to be understood that this invention is not limited to the particular methodology, syntheses, formulations, protocols, cell lines, constructs, and reagents described herein and as such can vary. It is also to be understood that the terminology used herein is for the purpose of describing particular aspects only, and is not intended to limit the scope of the present invention.

All publications, patents, and other references mentioned herein are provided for the purpose of describing and disclosing, for example, the constructs and methodologies that are described in these references, which might be used in connection with the presently described invention.

Definitions and Terminology

The groups defined for various symbols used in the formulas of this disclosure, as well as the optional substituents defined on those groups, can be defined as follows. Unless otherwise specified, any recitation of the number of carbon atoms in a particular group is intended to refer to the unsubstituted "base" group, therefore, any substituent recited on a base group is described by its own definition, including its own limitation of the number of carbon atoms. Unless otherwise specified, all structural isomers of a given structure, for example, all enantiomers, diasteriomers, and regioisomers, are included within this definition.

The terms "halogen" or "halo" includes fluorine, chlorine, bromine, or iodine.

The term "alkyl" group is used to refer to both linear and branched alkyl groups. Exemplary alkyl groups include, but are not limited to, methyl, ethyl, propyl, butyl, pentyl, hexyl, heptyl, octyl, nonyl, or decyl, and the like. Unless otherwise specified, an alkyl group has from 1 to 12 carbon atoms. Also unless otherwise specified, all structural isomers of a given structure, for example, all enantiomers and all diasteriomers, are included within this definition. For example, unless otherwise specified, the term propyl is meant to include n-propyl and iso-propyl, while the term butyl is meant to include n-butyl, iso-butyl, t-butyl, sec-butyl, and so forth.

The term "aryl" refers to an optionally substituted monocylic or polycyclic aromatic ring system of 6 to 14 carbon atoms. Exemplary groups include phenyl, naphthyl, 1,2,3,4-tetrahydronaphthalene, indane, fluorene, and the like. Unless otherwise specified, an aryl group typically has from 6 to 14 carbon atoms.

"Aralkyl" refers to an aryl substituted alkyl group, wherein the aryl group and the alkyl group are defined herein. Typically, the aryl group can have from 6 to 14 carbon atoms, and the alkyl group can have up to 10 carbon atoms. Exemplary aralkyl groups include, but are not limited to, benzyl, phenylethyl, phenylpropyl, phenylbutyl, propyl-2-phenylethyl and the like.

The term "haloalkyl" refers to a group containing at least one halogen and an alkyl portion as define above, that is, a haloalkyl is a substituted alkyl group that is substituted with one or more halogens. Unless otherwise specified, all structural isomers of a given structure, for example, all enantiomers and all diasteriomers, are included within this definition. Exemplary haloalkyl groups include fluoromethyl, chloromethyl, fluoroethyl, chloroethyl, trifluoromethyl, and the like. Unless otherwise specified, a haloalkyl group has from 1 to 12 carbon atoms.

A "cycloalkyl" group refers to a cyclic alkyl group which can be mono or polycyclic. Exemplary cycloalkyl groups include cyclopropyl, cyclobutyl, cyclopentyl, cyclohexyl, cycloheptyl, cyclooctyl, cyclononyl, and cyclodecyl. Unless otherwise specified, a cycloalkyl group has from 3 to 12 carbon atoms.

An "alkoxy" group refers to an —O(alkyl) group, where alkyl is as defined herein. Therefore, unless otherwise specified, all isomers of a given structure are included within a definition. Exemplary alkyl groups include methoxy, ethoxy, n-propoxy, iso-propoxy, n-butoxy, iso-butoxy, t-butoxy, and the like. Unless otherwise specified, an alkoxy group has from 1 to 12 carbon atoms. Unless otherwise specified, all structural isomers of a given structure, for example, all enantiomers and all diasteriomers, are included within this definition. For example, unless otherwise specified, the term propoxy is meant to include n-propoxy and iso-propoxy.

An "aryloxy" group refers to an —O(aryl) group, where aryl is as defined herein. Thus, the aryl portion of an aryloxy group can be substituted or unsubstituted. Exemplary aryloxy groups include, but are not limited to, phenoxy, naphthyl, and the like. Unless otherwise specified, an aryloxy group typically has from 6 to 14 carbon atoms.

"Haloalkoxy" refers to an alkoxy group with a halo substituent, where alkoxy and halo groups are as defined above. Exemplary haloalkoxy groups include fluoromethoxy, chloromethoxy, trifluoromethoxy, trichloromethoxy, fluoroethoxy, chloroethoxy, trifloroethoxy, perfluoroethoxy (—OCF$_2$CF$_3$), trifluoro-t-butoxy, hexafluoro-t-butoxy, perfluoro-t-butoxy (—OC(CF$_3$)$_3$), and the like. Unless otherwise specified, an haloalkoxy group typically has from 1 to 12 carbon atoms.

"Alkylthio" refers to an —S(alkyl) goup, where alkyl group is as defined above. Exemplary alkyl groups include methylthio, ethylthio, propylthio, butylthio, iso-propylthio, iso-butylthio, and the like. Unless otherwise specified, an alkylthio group typically has from 1 to 12 carbon atoms.

"Heteroaryl" is an aromatic monocyclic or polycyclic ring system of 4 to 10 carbon atoms, having at least one heteroatom or heterogroup selected from —O—, >N—, —S—, >NH or NR, and the like, wherein R is a substituted or unsubstituted alkyl, aryl, or acyl, as defined herein. In this aspect, >NH or NR are considered to be included when the heteroatom or heterogroup can be >N—. Exemplary heteroaryl groups include as pyrazinyl, isothiazolyl, oxazolyl, pyrazolyl, pyrrolyl, triazolyl, tetrazolyl, oxatriazolyl, oxadiazolyl, pyridazinyl, thienopyrimidyl, furanyl, indolyl, isoindolyl, benzo[1,3] dioxolyl, 1,3-benzoxathiole, quinazolinyl, isoquinolinyl, quinolinyl, pyridyl, 1,2,3,4-tetrahydro-isoquinolinyl, 1,2,3, 4-tetrahydro-quinolinyl pyridyl, thiophenyl, and the like. Unless otherwise specified, a heteroaryl group typically has from 4 to 10 carbon atoms. Moreover, the heteroaryl group can be bonded to the heterocyclic core structure at a ring carbon atom, or, if applicable for a N-substituted heteroaryl such as pyrrole, can be bonded to the heterocyclic core structure through the heteroatom that is formally deprotonated to form a direct heteroatom-pyrimdine ring bond.

"Heterocyclyl" is a non-aromatic saturated monocyclic or polycyclic ring system of 3 to 10 member having at least one heteroatom or heterogroup selected from —O—, >N—, —S—, >NR, >SO$_2$, >CO, and the like, wherein R is hydrogen or a substituted or an unsubstituted alkyl, aryl, or acyl, as defined herein. Exemplary heterocyclyl groups include aziridinyl, imidazolidinyl, 2,5-dihydro-[1,2,4]oxadiazolenyl, oxazolidinyl, isooxazolidinyl, pyrrolidinyl, piperdinyl, piperazinyl, morpholinyl, thiomorpholinyl, thiazolidinyl, 1,3-dioxolanyl, 1,4-dioxanyl, 2,5-dihydro-1H-imidazolyl, and the like. Unless otherwise specified, a heterocyclyl group typically has from 2 to 10 carbon atoms. A heterocyclyl group can be bonded through a heteroatom that is formally deprotonated or a heterocyclyl group can be bonded through a carbon atom of the heterocyclyl group.

An "alkoxycarbonyl" group refers to a —C(O)O(alkyl) group, wherein the alkyl portion of the alkoxycarbonyl group is defined as herein. Examples of alkoxycarbonyl groups include, but are not limited to, methoxycarbonyl, ethoxycarbonyl, t-butoxycarbonyl and the like.

An "acyl" group refers to a (C$_1$-C$_{10}$)alkyl-CO— group, wherein the (C$_1$-C$_{10}$)alkyl group is used in this structure to refer to the alkyl-linker moiety bonded both to the CO group, and to another chemical group. Examples of acyl groups include, but are not limited to, methylcarbonyl, ethylcarbonyl, propylcarbonyl, isopropylcarbonyl, and the like.

An "alkenylene" group refers to a (C$_2$-C$_{10}$) hydrocarbon linker comprising at least one C=C double bond within the C$_2$-C$_{10}$ chain. Examples of alkenylene groups include, but are not limited to, —CH=CH—, —CH$_2$—CH=CH, —CH$_2$—CH=CH—CH$_2$—, —CH$_2$—CH=CH—CH=CH—, and the like. Thus, unless otherwise specified, an alkenylene group has from 2 to 10 carbon atoms.

Further, the meaning of certain additional terms and phrases employed in the specification, can be defined as follows.

As used herein, the term "compound" includes both the singular and the plural, and includes any single entity or combined entities that have at least the affect disclosed herein and combinations, fragments, analogs or derivatives of such entities.

As used herein, the term "substance" refers broadly to any material of a particular kind or constitution. Examples of a "substance" can include, without limitation, a chemical element, a molecule, a compound, a mixture, a composition, an emulsion, a chemotherapeutic agent, a pharmacological agent, a hormone, an antibody, a growth factor, a cellular factor, a nucleic acid, a protein, a peptide, a peptidomimetic, a nucleotide, a carbohydrate, and combinations, fragments, analogs or derivatives of such entities.

The terms "treatment", "treating", "treat", and the like are used herein to refer generally to any process, application, therapy, etc., wherein a mammal is subject to medical attention with the object of obtaining a desired pharmacological and/or physiological effect for improving the mammal's condition or disease, directly or indirectly. The effect can be therapeutic in terms of a partial or complete stabilization or cure for a disease and/or adverse effect attributable to the disease. The effect also can include, for example, inhibition of disease symptom (that is, arresting its development) or relieving disease symptom (that is, causing regression of the disease or symptom).

A used herein, the term "therapeutically-effective amount" refers to that amount of at least one compound as disclosed herein, or their pharmaceutically-acceptable salts thereof, that is sufficient to bring about the biological or medical effect that is being sought in a mammal, system, tissue, or cell.

The term "preventing", "prevent", "prevention", and the like are used herein to refer generally to any process, application, therapy, etc., wherein a mammal is subject to medical attention with the object of obtaining a desired pharmacological and/or physiological effect for preventing onset of clinically evident condition or disease or preventing onset of a preclinically evident stage of a condition or disease. The effect can be prophylactic in terms of completely or partially preventing or reducing the risk of occurance of a condition or disease or symptom thereof.

A used herein, the term "prophylactically-effective amount" refers to that amount of a drug or pharmaceutical agent that will prevent or reduce the risk of occurrence of the biological or medical effect that is sought to be prevented in the cell, tissue, system, or mammal.

As used herein, the term "activation" refers to any alteration of a signaling pathway or biological response including, for example, increases above basal levels, restoration to basal levels from an inhibited state, and stimulation of the pathway above basal levels.

Publications and patents mentioned herein are disclosed for the purpose of describing, for example, the constructs and methodologies that are provided in the publications and patents, which might be used in connection with the present invention. Nothing herein is to be construed as an admission that the inventors are not entitled to antedate such publications, patents, or other disclosure by virtue of prior invention.

To the extent that any definition or usage provided by any document incorporated herein by reference conflicts with the definition or usage provided herein, the definition or usage provided herein controls.

When Applicants disclose or claim a range of any type, for example a range of temperatures, a range of numbers of atoms, a molar ratio, or the like, Applicants' intent is to disclose or claim individually each possible number that such a range could reasonably encompass, as well as any sub-ranges and combinations of sub-ranges encompassed therein. For example, when the Applicants disclose or claim a chemical moiety having a certain number of carbon atoms, Applicants' intent is to disclose or claim individually every possible number that such a range could encompass, consistent with the disclosure herein. For example, the disclosure that R is selected independently from an alkyl group having up to 12 carbon atoms, or in alternative language a $C_1$ to $C_{12}$ alkyl group, as used herein, refers to an R group that can be selected independently from a hydrocarbyl group having 1, 2, 3, 4, 5, 6, 7, 8, 9, 10, 11, or 12 carbon atoms, as well as any range between these two numbers for example a $C_3$ to $C_8$ alkyl group, and also including any combination of ranges between these two numbers for example a $C_3$ to $C_5$ and $C_7$ to $C_{10}$ hydrocarbyl group. In another example, by the disclosure that the molar ratio typically spans the range from about 0.1 to about 1.1, Applicants intend to recite that the molar ratio can be selected from about 0.1:1, about 0.2:1, about 0.3:1, about 0.4:1, about 0.5:1, about 0.6:1, about 0.7:1, about 0.8:1, about 0.9:1, about 1.0:1, or about 1.1:1.

Applicants reserve the right to proviso out or exclude any individual members of any such group, including any sub-ranges or combinations of sub-ranges within the group, that may be claimed according to a range or in any similar manner, if for any reason Applicants choose to claim less than the full measure of the disclosure, for example, to account for a reference that Applicants may be unaware of at the time of the filing of the application. Further, Applicants reserve the right to proviso out or exclude any individual substituents, compounds, ligands, structures, or groups thereof, or any members of a claimed group, if for any reason Applicants choose to claim less than the full measure of the disclosure, for example, to account for a reference that Applicants may be unaware of at the time of the filing of the application.

The following references disclose certain heterocyclic compounds.

TABLE 6

References disclosing heterocyclic compounds.

| Publication or Patent No. | Title |
| --- | --- |
| WO2005097806 | Preparation of heterocyclic piperidine derivatives as inhibitor of cholesterol ester transfer protein |
| WO2005095395 | Preparation of 1,2,3,4-tetrahydro-1,5-naphthyridin-4-amines as cholesteryl ester transfer protein inhibitors |
| WO2005095409 | Preparation of 1,2,3,4-tetrahydroquinolin-4-amines as cholesteryl ester transfer protein inhibitors |
| WO2005030185 | Method using cholesteryl ester transfer protein (CETP) inhibitors for inhibiting remnant lipoprotein production |
| US2004039018 | Use of cholesteryl ester transfer protein (CETP) inhibitors and antihypertensive agents and optional HMG-CoA reductase inhibitors for the treatment of cardiovascular conditions |
| WO2000017165 | Preparation of 4-amino-substituted 2-substituted 1,2,3,4-tetrahydroquinolines as CEPT inhibitors |
| US2004053842 | Therapeutic use and pharmaceutical compositions of cholesterol ester transfer protein (CETP) inhibitors and optional HMG-CoA reductase inhibitors and/or antihypertensive agents |
| WO2003000295 | Self-emulsifying formulations of cholesteryl ester transfer protein inhibitors and surfactants |
| WO2002011710 | Pharmaceutical compositions of cholesteryl ester transfer protein inhibitors |
| US2003198674 | Controlled release dosage forms containing cholesteryl ester transfer protein inhibitor |
| WO2003063832 | Pharmaceutical compositions comprising a solid amorphous dispersion of CETP inhibitors |
| US2003104063 | Pharmaceutical compositions containing a solid dispersion of a poorly-soluble drug in a matrix and a solubility-enhancing polymer |
| US2003054037 | Pharmaceutical compositions of adsorbates of amorphous drug |
| US2003170309 | Pharmaceutical compositions containing polymer and drug assemblies |
| US2003072801 | Pharmaceutical compositions comprising concentration-enhancing polymers |
| US2004185102 | Dosage forms comprising a CETP inhibitor and an HMG-CoA reductase inhibitor |

Applicants reserve the right to proviso out or to restrict from any claim currently presented, or from any claim that may be presented in this or any further application based upon this disclosure, including claims drawn any genus or subgenus disclosed herein, any compound or group of compounds disclosed in any reference, including any reference provided herein.

The following acronyms, abbreviations, terms and definitions have been used throughout this disclosure. The following acronyms, abbreviations, terms and definitions have been used throughout the experimental section. Acronyms and abbreviations: THF (tetrahydrofuran), DMF (N,N-dimethylformamide), IPA (iso-propanol), TBAB (tetra-n-butylammonium bromide), DCM (dichloromethane), DPE (diphenyl ether), g (grams), mL (milliliters), mp (melting point), eqv (equivalent, equivalents) rt or RT (room temperature), aq (aqueous), min (minute), h or hr (hour), atm (atmosphere), conc. (concentrated), MS or mass spec (mass spectroscopy/spectrometry), NMR (nuclear magnetic resonance). NMR abbreviations: br (broad), apt (apparent), s (singlet), d (doublet), t (triplet), q (quartet), dq (doublet of quartets), dd (doublet of doublets), dt (doublet of triplets), m (multiplet).

General Synthetic Procedures.

Room temperature is defined as an ambient temperature range, typically from about 20° C. to about 35° C. An ice bath (crushed ice and water) temperature is defined as a range, typically from about −5° C. to about 0° C. Temperature at reflux is defined as ±15° C. of the boiling point of the primary reaction solvent. Overnight is defined as a time range of from about 8 to about 16 hours. Vacuum filtration (water aspirator) is defined as occurring over a range of pressures, typically from about 5 mm Hg to about 15 mm Hg. Dried under vacuum is defined as using a high vacuum pump at a range of pressures, typically from about 0.1 mm Hg to about 5 mm Hg. Neutralization is defined as a typical acid-based neutralization method and measured to a pH range of from about pH 6 to about pH 8, using pH-indicating paper. Brine is defined as a saturated aqueous sodium chloride. Nitrogen atmosphere is defined as positive static pressure of nitrogen gas passed through a Drierite™ column with an oil bubbler system. Concentrated ammonium hydroxide is defined as an approximately 15 M solution. Melting points were measured against a mercury thermometer and are not corrected.

All eluents for column or thin layer chromatography were prepared and reported as volume:volume (v:v) solutions. The solvents, reagents, and the quantities of solvents and/or reagents used for reaction work-up or product isolation can be those that typically would be used by one of ordinary skill in organic chemical synthesis, as would be determined for the specific reaction or product to be isolated. For example: 1) crushed ice quantity typically ranged from about 10 g to about 1000 g depending on reaction scale; 2) silica gel quantity used in column chromatography depended on material quantity, complexity of mixture, and size of chromatography column employed and typically ranged from about 5 g to about 1000 g; 3) extraction solvent volume typically ranged from about 10 mL to about 500 mL, depending upon the reaction size; 4) washes employed in compound isolation ranged from about 10 mL to about 100 mL of solvent or aqueous reagent, depending on scale of reaction; and 5) drying reagents (potassium carbonate, sodium carbonate or magnesium sulfate) ranged from about 5 g to about 100 g depending on the amount of solvent to be dried and its water content.

Spectroscopic and Other Instrumental Procedures

NMR. The $^1$H spectra described herein were obtained using Varian Gemini 200 MHz spectrometers. Spectrometer field strength and NMR solvent used for a particular sample are indicated in the examples, or on any NMR spectra that are shown as Figures. Typically, $^1$H NMR chemical shifts are reported as δ values in parts per million (ppm) downfield from tetramethylsilane (TMS) (δ=0 ppm) as an internal standard. Solid or liquid samples were dissolved in an appropriate NMR solvent (typically CDCl$_3$ or DMSO-d$_6$), placed in a NMR sample tube, and data were collected according to the spectrometer instructional manuals. Most samples were analyzed in Variable Temperature mode, typically at about 55° C., though some data for some samples were collected with the probe at ambient probe temperature. NMR data were processed using the software provided by Varian, VNMR 6.1 G version.

The present invention is further illustrated by the following examples, which are not to be construed in any way as imposing limitations upon the scope of this disclosure, but rather are intended to be illustrative only. On the contrary, it is to be clearly understood that resort may be had to various other embodiments, modifications, and equivalents thereof which, after reading the description herein, may suggest themselves to one of ordinary skill in the art without departing from the spirit of the present invention. Thus, the skilled artisan will appreciate how the experiments and Examples may be further implemented as disclosed by variously altering the following examples, substituents, reagents, or conditions. In the following examples, in the disclosure of any measurements, including temperatures, pressures, times, weights, percents, concentrations, ranges, chemical shifts, frequencies, molar ratio, and the like, it is to be understood that such measurements are respectively, "about."

EXAMPLES

Example 1

Synthesis of 4-[(3,5-Bis-trifluoromethyl-benzyl)-methoxycarbonyl-amino]-6-ethyl-1,3-dimethyl-1,4,5,6-tetrahydro-pyrazolo[3,4-b]pyridine-7-carboxylic acid ethyl ester

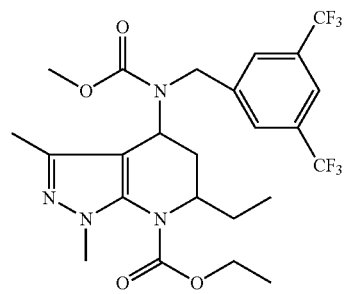

(E1)

Step (i): Preparation of (1-Benzotriazol-1-yl-ethyl)-(2,5-dimethyl-2H-pyrazol-3-yl)-amine

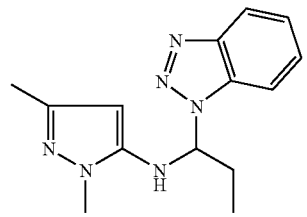

Benzotriazole (2.14 g, 18 mmol) and dry toluene (24 mL) were charged to a flask under an argon atmosphere. A solution of 5-amino-1,3-dimethylpyrazole (2 g, 18 mmol) in toluene (10 mL) was added to the benzotriazole solution over approximately 0.5 min, followed by the drop-wise addition of propionaldehyde (1.14 g, 19.8 mmol). After this reaction mixture was stirred for 24 hours, n-heptane (30 mL) was added and slurry was stirred for an additional 1 hour, after which time the n-heptane was decanted off, and the pasty residue was dried under vacuum to afford the title compound (4.04 g, 83%).

$^1$H NMR (CDCl$_3$, 400 MHz): δ 8.06-8.03 (m, 1H), 7.53-7.46 (m, 2H), 7.38-7.34 (m, 3H), 5.45 (t, J=7.9 Hz, 1H), 4.28 (s, 2H), 3.52 (s, 3H), 2.64-2.60 (m, 1H), 2.58-2.44 (m, 1H), 2.29 (s, 3H), 0.92 (t, J=7.2 Hz, 3H) CI-MS (m/z): 271 (M⁺+1, 100%) IR (neat, cm⁻¹): 3233, 3189, 1545

Step (ii): Preparation of (6-Ethyl-1,3-dimethyl-4,5,6, 7-tetrahydro-1H-pyrazolo[3,4-b]pyridine-4-yl)-carbamic acid benzyl ester

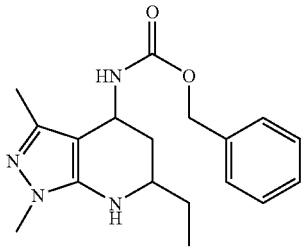

N-Vinyl-carbamic acid benzyl ester (2.65 g, 14.99 mmol) and dry toluene (10 mL) were charged to a flask under a nitrogen atomsphere. (1-Benzotriazol-1-yl-ethyl)-(2,5-dimethyl-2H-pyrazol-3-yl)-amine (4.04 g, 14.99 mmol), obtained in step (i), and p-toluenesulphonic acid monohydrate (0.023 g, 0.15 mmol) were added to this solution and the mixture was heated to around 70° C. for 12 hours. The resulting mixture was cooled to room temperature, transferred to a separatory funnel, and ethyl acetate (100 mL) was added. The organic phase was subsequently washed with 1N NaOH (1×16 mL), H₂O (1×16 mL), and brine (1×16 mL). The organic layer was dried over sodium sulphate and then concentrated under vacuum to afford the title compound as a white solid (0.35 g, 7%).

¹H NMR (CDCl₃, 400 MHz): δ 7.36-7.31 (m, 5H), 5.13 (s, 2H), 4.95-4.89 (m, 1H), 4.71-4.68 (m, 1H), 3.51 (s, 3H), 3.23-3.20 (m, 2H), 2.32-2.28 (m, 1H), 2.10 (s, 3H), 1.41-1.33 (m, 1H), 0.99 (t, J=7.2 Hz, 3H) ES-MS (m/z): 329 (M⁺+1, 100%)

Step (iii): Preparation of 4-Benzyloxycarbonylamino-6-ethyl-1,3-dimethyl-1,4,5,6,-tetrahydropyrazolo[3,4-b]pyridine-7-carboxylic acid ethyl ester

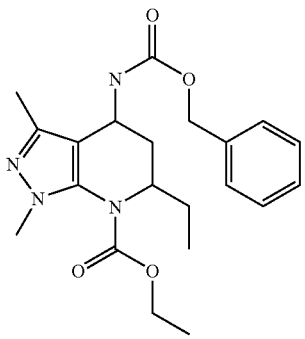

(6-Ethyl-1,3-dimethyl-4,5,6,7-tetrahydro-1H-pyrazolo[3,4-b]pyridine-4-yl)-carbamic acid benzyl ester (0.35 g, 1.08 mmol) obtained in step (ii), dry THF (5 mL) and potassium carbonate (0.45 g, 3.2 mmol) were charged to a flask under a nitrogen atomsphere. This mixture was stirred at room temperature for about 0.5 h, after which time ethyl chloroformate (0.47 g, 3.2 mmol) was added drop-wise. This reaction mixture was then stirred for about 4 h, water was added to the mixture, and the aqueous layer was extracted with ethyl acetate (3×10 mL). The combined organic layer was washed with brine (1×20 mL), dried over sodium sulphate, and concentrated under vacuum to afford the title compound (0.375 g, 88%).

¹H NMR (CDCl₃, 400 MHz): δ 7.38-7.30 (m, 5H), 5.16-5.08 (m, 2H), 4.84-4.81 (m, 1H), 4.68-4.66 (m, 1H), 4.48 (s, 1H), 4.31-4.21 (m, 2H), 3.64 (s, 3H), 2.15 (s, 3H), 1.61-1.55 (b, 1H), 1.43-1.39 (m, 2H), 1.37-1.21 (m, 3H), 0.92-0.86 (m, 3H). ES-MS (m/z): 401 (M⁺+1, 100%) IR (neat, cm⁻¹): 3342, 2926, 1683.

Step (iv): Preparation of 4-Amino-6-ethyl-1,3-dimethyl-1,4,5,6-tetrahydro-pyrazolo[3,4-b]pyridine-7-carboxylic acid ethyl ester

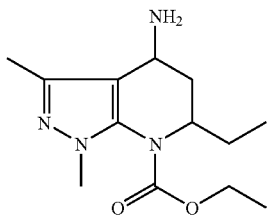

4-Benzyloxycarbonylamino-6-ethyl-1,3-dimethyl-1,4,5, 6,-tetrahydro-pyrazolo[3,4-b]pyridine-7-carboxylic acid ethyl ester (0.34 g, 0.85 mmol) obtained in step (iii), methanol (5 mL), and ammonium formate were charged to a flask under a nitrogen atomsphere. To this mixture was added 10% Pd/C (50% wet) (0.1 g), and the resulting slurry was heated at about 40° C. for around 1 hour. The reaction mixture was then cooled to room temperature and filtered through Celite™, and the filtrate was concentrated under vacuum to afford the title compound (0.171 g, 76%).

¹H NMR (CDCl₃, 400 MHz): δ 4.50-4.47 (m, 1H), 4.31-4.17 (m, 2H), 3.94 (d, J=5.4 Hz, 1H), 3.65 (s, 3H), 2.30 (s, 3H), 2.20-2.15 (s, 1H), 1.83 (dd, 1H), 1.57-1.46 (m, 4H), 1.30 (t, J=7.0 Hz, 3H), 0.93 (t, J=7.3 Hz, 3H) CI-MS (m/z): 267 (M⁺+1, 70%), 250 IR (neat, cm⁻¹): 2935, 1712, 1281, 1100

Step (v): Preparation of 4-[(3,5-Bis-trifluoromethyl-benzylidene)-amino]-6-ethyl-1,3-dimethyl-1,4,5,6-tetrahydro-pyrazolo[3,4-b]pyridine-7-carboxylic acid ethyl ester

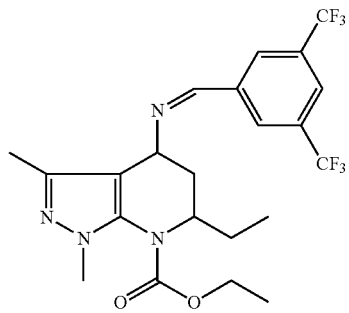

The compound 4-Amino-6-ethyl-1,3-dimethyl-1,4,5,6-tetrahydro-pyrazolo-[3,4-b]pyridine-7-carboxylic acid ethyl ester (0.1 g, 0.375 mmol) obtained in step (iv) was dissolved in methanol (10 mL), and acetic acid (0.05 mL, 0.75 mmol) was added to the solution. This reaction mixture was stirred at room temperature for around 3 hours, after which time the solvent was removed under vacuum. Water was added to the residue and the product was extracted with ethyl acetate (2×10 mL). The combined organic layer was dried over sodium sulfate, filtered, and evaporated the filtrate was evaporated to dryness on a rotary evaporator to yield the desired compound (0.025 g, 11%).

$^1$H NMR (CDCl$_3$, 400 MHz): δ 8.44 (s, 1H), 8.16 (s, 2H), 7.92 (s, 1H), 4.57-4.56 (m, 1H), 4.48 (d, J=5.9 Hz, 1H), 4.34-4.30 (m, 2H), 3.71 (s, 3H), 2.34-2.27 (m, 2H), 2.00 (s, 3H), 1.91 (dd, 1H), 1.88-1.87 (m, 1H), 1.66-1.57 (m, 1H), 1.34 (t, J=7.0 Hz, 3H), 0.92 (t, J=7.2 Hz, 3H). ES-MS (m/z): 491 (M$^+$+1, 100%)

Step (vi): Preparation of 4-(3,5-bis-trifluoromethyl-benzylamino)-6-ethyl-1,3-dimethyl-1,4,5,6-tetrahydro-pyrazolo[3,4-b]pyridine-7-carboxylic acid ethyl ester

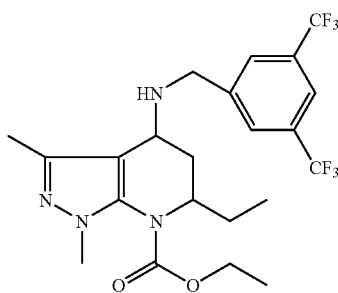

To a stirred solution of [(3,5-Bis-trifluoromethyl-benzylidene)-amino]-6-ethyl-1,3-dimethyl-1,4,5,6-tetrahydro-pyrazolo[3,4-b]pyridine-7-carboxylic acid ethyl ester (0.19 g, 0.04 mmol) obtained in step (v), in 10 mL of methanol was added sodium cyanoborohydride (0.078 g, 0.12 mmol). This reaction mixture was stirring for around 3 hours at room temperature, after which time the methanol was evaporated from the solution to afford a crude residue. Water was added to this residue, and the product was extracted with ethyl acetate (3×10 mL). The organic solvent was dried over sodium sulfate, filtered, and the solvent was evaporated from the filtrate under vacuum to provide the desired amine compound (0.019 g, 95%).

CI-MS (m/z): 493 (M$^+$+1, 100%).

Step (vii): Preparation of 4-[(3,5-Bis-trifluoromethyl-benzyl)-methoxycarbonyl-amino]-6-ethyl-1,3-dimethyl-1,4,5,6-tetrahydro-pyrazolo[3,4-b]pyridine-7-carboxylic acid ethyl ester (E1)

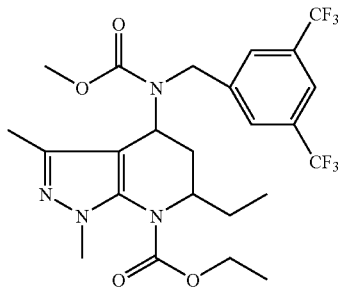

4-(3,5-Bis-trifluoromethyl-benzylamino)-6-ethyl-1,3-dimethyl-1,4,5,6-tetrahydro-pyrazolo[3,4-b]pyridine-7-carboxylic acid ethyl ester (0.02 g, 0.04 mmol) obtained in step (vi), and K$_2$CO$_3$ (0.016 g, 0.12 mmol) were charged to a flask under a nitrogen atmosphere. Dry THF (5 mL) was added to this mixture, and the resulting mixture was stirred at room temperature for about 30 min, after which time methyl chloroformate (0.011 g, 0.12 mmol) was added dropwise. The reaction was stirred at room temperature overnight. Water was then added to the reaction mixture and the product was extracted with ethyl acetate. The resulting organic layer was dried over sodium sulphate, filtered, and the filtrate was concentrated under vacuum to provide a residue. This residue was purified by column chromatography over 100-200 mesh silica gel using 8% ethyl acetate in petroleum ether as eluent, to afford the title compound. Yield: 0.01 g (50%).

$^1$H NMR (CDCl$_3$, 400 MHz): δ 7.74 (s, 1H), 7.56-7.51 (m, 2H), 5.82-5.80 (m, 2H), 5.01-4.90 (m, 1H), 4.60-4.52 (m, 1H), 4.26-4.21 (m, 2H), 3.86-3.77 (m, 3H), 3.66 (s, 3H), 2.04-1.95 (m, 4H), 1.6 (s, 3H), 0.88-0.79 (m, 6H) CI-MS (m/z): 550 (M$^+$, 100%) IR (neat, cm$^{-1}$): 2927, 1706.

Example 2

Preparation of 4-[(3,5-Bis-trifluoromethyl-benzyl)-methoxycarbonyl-amino]-2-ethyl-6,8-dimethyl-3,4-dihydro-2H-[1,7]naphthyridine-1-carboxylic acid ethyl ester

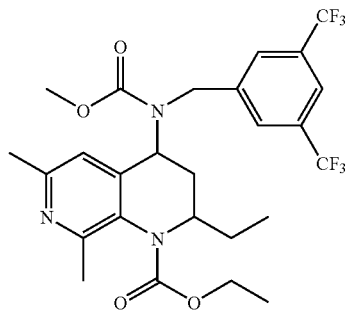

Step (i): Preparation of 2-[(2,6-dimethyl-pyridin-3-ylamino)-methylene]-malonic acid diethyl ester

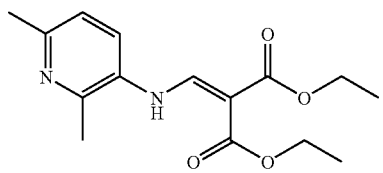

3-Amino-2,6-dimethylpyridine (0.5 g, 4.09 mmol) and 2-ethoxymethylene-malonic acid dimethyl ester (0.886 g, 4.09 mmol) were placed in a round bottom flask and this mixture was heated at 110° C. under a nitrogen atmosphere for 3 h. The reaction was then cooled to RT and petroleum ether was then added. The suspension was filtered and the collected precipitate was maintained under vacuum overnight to provide the product as a light yellow solid (84%).

$^1$H NMR (CDCl$_3$, 400 MHz) δ 11.10-11.07 (d, J=13.2 Hz, 1H), 8.44-8.40 (m, 1H), 7.41-7.39 (m, 1H), 7.06-7.04 (m,

1H), 4.33 (q, J=7.2 Hz, 2H), 4.25 (q, J=7.2 Hz, 2H), 2.59 (s, 3H), 2.52 (s, 3H), 1.38 (t, J=7.1 Hz, 3H), 1.33 (t, J=7.1 Hz, 3H). m/z (ES-MS) 293 (M+, 60%)

Step (ii): Preparation of 6,8-Dimethyl-4-oxo-1,4-dihydro-[1,7]naphthyridine-3-carboxylic acid ethyl ester

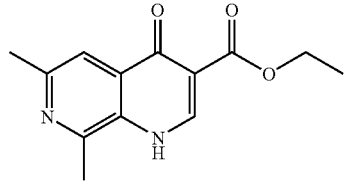

2-[(2,6-Dimethyl-pyridin-3-ylamino)-methylene]-malonic acid diethyl ester, prepared in step (i) and diphenyl ether (DPE) were placed in a round bottom flask and this mixture was heated to 260° C. for 1 h. The reaction was then cooled to RT and the content was purified by column chromatography over 100-200 mesh silica gel, eluted with 8% methanol in chloroform, to give the product as a brown solid (36%).

$^1$H NMR (DMSO-d$_6$) δ 8.41 (s, 1H), 7.68 (s, 1H), 4.24 (q, J=7.2 Hz, 2H), 2.72 (s, 3H), 2.54 (s, 3H), 1.32-1.24 (m, 3H) m/z (ES-MS) δ 247 (M$^+$+1, 100%)

Step (iii): Preparation of 6,8-dimethyl-4-oxo-4H-[1,7]naphthyridine-1,3-dicarboxylic acid 1-benzyl ester 3-ethyl ester

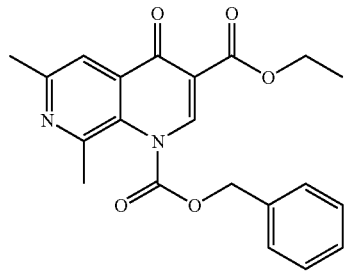

6,8-Dimethyl-4-oxo-1,4-dihydro-[1,7]naphthyridine-3-carboxylic acid ethyl ester (0.2 g, 0.628 mmol), prepared in step (ii), and dichloromethane (10 mL) were added to a 50 mL round bottom flask. This mixture was cooled to 0° C. and stirred, and triethylamine (0.19 g, 1.88 mmol) was then added to the mixture dropwise. Stirring of the reaction mixture was continued at the same temperature for another 0.5 h, after which time benzyl chloroformate (0.16 g, 0.943 mmol) was added to the mixture. The temperature was allowed to increase to RT, and stirring was continued at this temperature for 2 h. Water was added to the reaction mixture and the mixture was extracted with dichloromethane (2×25 mL). The combined organic phase was washed with brine, dried over sodium sulfate, and the organic solvent was evaporated to provide a residue. This residue was purified by column chromatography over 100-200 mesh silica gel, used 5% MeOH and chloroform as eluent, to provide the compound as a yellow solid (0.1 g, 42%).

$^1$H NMR (CDCl$_3$, 400 MHz) δ 9.37 (s, 1H), 7.49-7.41 (m, 6H), 5.36 (s, 2H), 4.34 (q, J=6.9 Hz, 2H), 3.07 (s, 3H), 2.69 (s, 3H), 1.34 (t, J=7.2 Hz, 3H).

Step (iv): Preparation of 2-ethyl-6,8-dimethyl-4-oxo-3,4-dihydro-2H-[1,7]naphthyridine-1,3-dicarboxylic acid 1-benzyl ester 3-methyl ester

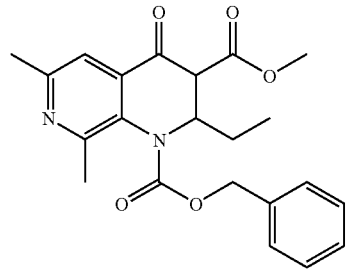

This compound can be obtained by reacting a stirred suspension of 6,8-dimethyl-4-oxo-4H-[1,7]naphthyridine-1,3-dicarboxylic acid 1-benzyl ester 3-ethyl ester, prepared in step (iii) and CuI (copper iodide) in THF, with freshly prepared EtMgBr (ethyl magnesium bromide) at −78° C., followed by a typical workup.

Step (v): Preparation of 2-Ethyl-6,8-dimethyl-4-oxo-3,4-dihydro-2H-[1,7]naphthyridine-1-carboxylic acid benzyl ester

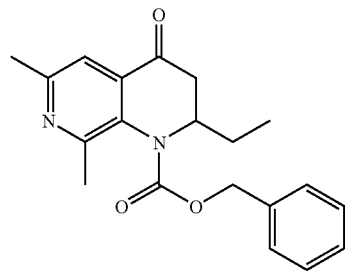

This compound can be obtained by reacting a solution of 2-ethyl-6,8-dimethyl-4-oxo-3,4-dihydro-2H-[1,7]naphthyridine-1,3-dicarboxylic acid 1-benzyl ester 3-methyl ester, in ethanol, with 2N NaOH at reflux temperature, for a time period from about 0.5 h to about 2 h, followed by a typical workup.

Step (vi): Preparation of 2-Ethyl-6,8-dimethyl-2,3-dihydro-1H-[1,7]naphthyridin-4-one

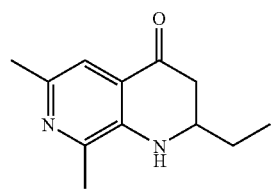

This compound can be obtained by reacting a solution of 2-ethyl-6,8-dimethyl-4-oxo-3,4-dihydro-2H-[1,7]naphthyridine-1-carboxylic acid benzyl ester in methanol, under nitrogen atmosphere, with ammonium formate (2.5 eqv) and 10%

Pd—C (50% water wet), at about 40° C. for a time period of about 1 h, followed by a typical workup.

Step (vii): Preparation of 2-Ethyl-6,8-dimethyl-4-oxo-3,4-dihydro-2H-[1,7]naphthyridine-1-carboxylic acid ethyl ester

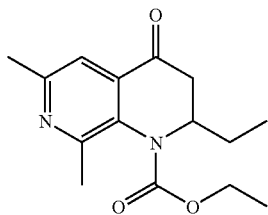

This compound can be obtained by reacting a suspension of $K_2CO_3$ (3-5 eqv) in THF with a solution of 2-ethyl-6,8-dimethyl-2,3-dihydro-1H-[1,7]naphthyridin-4-one in THF and ethyl chloroformate (1.5 to 2 eqv), typically at a temperature from about RT to about 50° C., followed by a typical workup procedure.

Step (viii): Preparation of 2-Ethyl-4-hydroxyimino-6,8-dimethyl-3,4-dihydro-2H-[1,7]naphthyridine-1-carboxylic acid ethyl ester

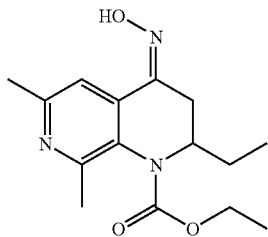

This compound can be prepared by reacting an ethanolic solution of 2-ethyl-6,8-dimethyl-4-oxo-3,4-dihydro-2H-[1,7]naphthyridine-1-carboxylic acid ethyl ester, with $NH_2OH.HCl$ (2-3 eqv) and pyridine (1-3 eqv), typically at reflux temperature for about 2 to about 6 h, followed by a typical workup procedure.

Step (ix): Preparation of 4-Amino-2-ethyl-6,8-dimethyl-3,4-dihydro-2H-[1,7]naphthyridine-1-carboxylic acid ethyl ester

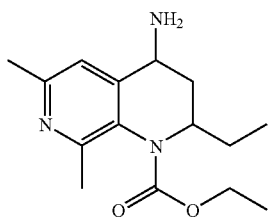

This compound can be prepared by reacting a solution of 2-ethyl-4-hydroxyimino-6,8-dimethyl-3,4-dihydro-2H-[1,7]naphthyridine-1-carboxylic acid ethyl ester in acetic acid with Zn (5 to 10 eqv), typically at reflux temperature, for about 1 h to about 5 h, followed by a typical workup procedure.

Step (x): Preparation of 4-(3,5-Bis-trifluoromethyl-benzylamino)-2-ethyl-6,8-dimethyl-3,4-dihydro-2H-[1,7]naphthyridine-1-carboxylic acid ethyl ester

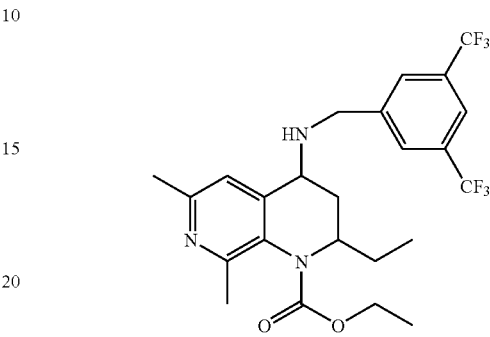

This compound can be prepared by reacting a solution of 4-amino-2-ethyl-6,8-dimethyl-3,4-dihydro-2H-[1,7]naphthyridine-1-carboxylic acid ethyl ester (1 eqv) with bis-trifluoromethyl benzaldehyde (1 eqv), in presence of acetic acid (1-2 eqv) and sodium cyanoborohydride (2 to 5 eqv), in a solvent such as MeOH, followed by a typical workup procedure.

Step (xi): Preparation of 4-[(3,5-Bis-trifluoromethyl-benzyl)-methoxycarbonyl-amino]-2-ethyl-6,8-dimethyl-3,4-dihydro-2H-[1,7]naphthyridine-1-carboxylic acid ethyl ester

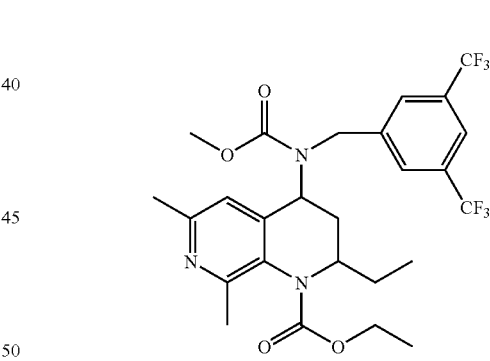

This compound can be prepared by reacting, a solution of 4-(3,5-bis-trifluoromethyl-benzylamino)-2-ethyl-6,8-dimethyl-3,4-dihydro-2H-[1,7]naphthyridine-1-carboxylic acid ethyl ester in THF and $K_2CO_3$ (2 to 5 eqv) with methyl chloroformate, followed by a typical workup procedure.

Example 3

Determination of In Vitro Activity

An in vitro fluorescence-based assay to identify CETP inhibitors was developed from modifications of the protocols outlined in Bisgaier et al., J Lipid Res., 34(9): 1625-34 (1993) and Epps et al., Chem Phys Lipids., 77(1): 51-63 (1995). Acceptor and donor lipid microemulsions were prepared according to Bisgaier et al., 1993, except that the buffer was prepared with 0.67 ug/ml human HDL (Calbiochem). Donor microemulsions contained the fluorescent cholesteryl ester analog BODIPY-CE (Molecular Probes), characterized by excitation and emission maxima at 503 nm and 518 nm, respectively. The CETP-mediated transfer of fluorescent cholesteryl ester to acceptor particles was monitored over a 2-hour time period using the FAM filter set (excitation 492 nm, emission 516 nm) in an MX3000P fluorescent plate reader (Stratagene). Recombinant CETP enzyme (Cardiovascular Targets) was used at 0.14 ng/μl, final concentration, to achieve lipid transfer. CETP inhibition by compounds was compared to DMSO controls and graphed as a percentage of the control CETP activity over 2 hours. The $IC_{50}$ curves for CETP inhibition were generated from the activity profiles. Active compounds were also tested for CETP inhibition as above, but in the presence of 3% human serum albumin, fraction V (Calbiochem).

Using this protocol, $IC_{50}$ data for CETP inhibition were obtained. The results are shown below in the following Table.

TABLE 7

Experimental data for CETP inhibition

| Compound | CETP Inhibition ($IC_{50}$) |
| --- | --- |
| E1 | 4.6 μM |

We claim:
1. A compound having the formula:

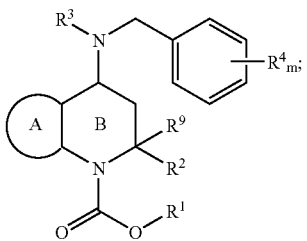

(I)

or a salt, a diastereomeric mixture, an enantiomer, a tautomer, a racemic mixture thereof, or any combination thereof, wherein:

ring A is fused to ring B and is selected from:

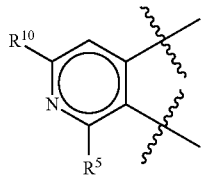

$R^1$ is an alkyl, a cycloalkyl, a haloalkyl, an aryl, an aralkyl, a heteroaryl, or a heterocyclyl, any of which having up to 12 carbon atoms; wherein any heteroaryl or heterocyclyl comprises at least one heteroatom or heterogroup selected independently from —O—, —N—, —S, —$NR^6$, —$SO_2$, or —CO;

$R^2$ and $R^9$ are the same or different, and are selected independently from an alkyl, a haloalkyl, a cycloalkyl, or a cycloalkyl-substituted alkyl, any of which having up to 12 carbon atoms, or hydrogen;

$R^3$ is selected from: 1) an alkyl having up to 12 carbon atoms; 2) $CO_2R^6$, $COR^8$, $SO_2R^8$, $SO_2NR^6R^7$, or $CONR^6R^7$; 3) a substituted or an unsubstituted aryl, or a substituted or an unsubstituted 5-, 6-, or 7-membered heterocyclyl or heteroaryl, comprising from 1 to 4 heteroatoms or heterogroups, selected independently from —O—, —N—, —S, or —$NR^6$, any of which having up to 12 carbon atoms; or 4) hydrogen or cyano;

wherein when $R^3$ is an aryl, a heterocyclyl, or a heteroaryl, $R^3$ is optionally substituted with up to three substituents selected independently from a halide, a hydroxyl, a cyano, an alkoxy having up to 12 carbon atoms, or $R^4$, in each occurrence, is selected independently from: 1) an alkyl, a cycloalkyl, a haloalkyl, an alkoxy, an aryloxy, a haloalkoxy, an aryl, or a heteroaryl, any of which having up to 12 carbon atoms, wherein any heteroaryl comprises at least one heteroatom or heterogroup selected from —O—, —N—, —S, or —$NR^6$; or 2) halogen, hydroxy, or cyano;

m is an integer selected from 0, 1, 2, or 3;

$R^5$ is selected from: 1) an alkyl, a haloalkyl, an alkoxy, a haloalkoxy, or an aryl, any of which having up to 12 carbon atoms; 2) $CO_2R^6$ or $COR^8$; or 3) hydrogen, cyano, or hydroxyl;

$R^6$ and $R^7$ are independently an alkyl or a haloalkyl, any of which having up to 12 carbon atoms, or hydrogen;

$R^8$ is an alkyl having up to 12 carbon atoms; and $R^{10}$ is selected from: 1) an alkyl, a haloalkyl, an alkoxy, a haloalkoxy, or an aryl, any of which having up to 12 carbon atoms; 2) $CO_2R^6$ or $COR^8$; or 3) hydrogen, halogen, or cyano;

$R^{11}$ is selected independently from:
1) an alkyl, a haloalkyl, a cycloalkyl, or an alkoxycarbonyl, any of which having up to 12 carbon atoms;
2) a substituted or an unsubstituted heteroaryl or heterocyclyl, any of which having up to 12 carbon atoms, comprises at least one heteroatom or heterogroup selected independently from —O—, —N—, —S, —$NR^6$, —$SO_2$, or —CO, wherein any substituted heteroaryl or heterocyclyl is substituted with up to three substituents selected independently from an alkyl having up to 12 carbon atoms or a hydroxyl; or
3) —CO-Z-$R^{13}$, —CO—$R^{12}$, —CO-Z-$(CH_2)_n$—CO-Z-$R^{13}$, —$NR^{15}R^{16}$, -Z-CO—$(CH_2)_n$-Z-$R^{13}$, -Z-CO—$(CH_2)_n$—CO-Z-$R^{13}$, —O—$(CH_2)_n$—CO-Z-$R^{13}$, —O—$(CH_2)_n$—$R^{14}$, —O—$R^{12}$—$(CH_2)_n$—$R^{13}$, —O—$R^{14}$—CO—O—$R^{13}$, —O—$(CH_2)_n$—$R^{12}$, —O—$(CH_2)_n$—NR'R", —O—$(CH_2)_n$—$CO_2$—$(CH_2)_n$—$R^{13}$, —O—$(CH_2)_n$—CONR'R", —O—$(CH_2)_n$—$SR^8$, —O—$(CH_2)_n$—$CO_2$—$R^{13}$, —O—$(CH_2)_n$—O—$(CH_2)_n$—$OR^{13}$, —O—$(CH_2)_n$—CONR'R", —O—$(CH_2)_n$—CON H—$(CH_2)_n$—$OR^{13}$, —O—$(CH_2)_n$—$SO_2R^8$, —O—$(CH_2)_n$—$R^{13}$, —O—$(CH_2)_n$—$OR^{13}$, —O—$(CH_2)_n$—O—$(CH_2)$n-$OR^{13}$, —S—$(CH_2)_n$—CONR'R", —$SO_2$—$(CH_2)_n$—$OR^{13}$, —$SO_2$—$(CH_2)_n$—CONR'R", —$(CH_2)_n$—O—CO—$R^8$, —$(CH_2)_n$—$R^{12}$, —$(CH_2)_n$—$R^{13}$, —$(CH_2)_n$—N—$(CH_2)_n$—$OR^{13}$, —$(CH_2)_n$—CO-Z-$R^{13}$, —$(CH_2)_n$-Z-$R^{13}$, or -alkenylene-$CO_2(CH_2)_n$—$R^{13}$;

n, in each occurrence, is independently 1, 2, or 3;

$R^{12}$, in each occurrence, is independently selected from a substituted or an unsubstituted heterocyclyl having up to 12 carbon atoms, comprising at least one heteroatom or heterogroup selected independently from —O—, —N—, —S, —NR$^6$, —SO$_2$, or —CO, wherein any substituted heterocyclyl is substituted with up to three substituents selected independently from an acyl, an alkyl, or an alkoxycarbonyl, any of which having up to 12 carbon atoms, or —COOH;

R$^{13}$, in each occurrence, is independently selected from: 1) hydrogen; or 2) a cycloalkyl, an aryl, a haloalkyl, a heterocyclyl, or an alkyl group optionally substituted with at least one hydroxyl, any of which having up to 12 carbon atoms, wherein any heterocyclyl comprises at least one heteroatom or heterogroup selected independently from —O, —N—, —S, —NR$^6$, —SO$_2$, or —CO;

R$^{14}$, in each occurrence, is independently selected from a heterocyclyl, a cycloalkyl, or an aryl, any of which having up to 12 carbon atoms, wherein any heterocyclyl comprises at least one heteroatom or heterogroup selected independently from —O, —N—, —S, —NR$^6$, —SO$_2$, or —CO;

Z, in each occurrence, is independently —O or —NR$^6$;

R' and R", in each occurrence, are independently selected from hydrogen or an alkyl having up to 12 carbon atoms; and R$^{15}$ and R$^{16}$, in each occurrence, are independently selected from: 1) hydrogen; 2) an alkyl having up to 12 carbon atoms; or 3) —(CH$_2$)$_n$—O—R$^{13}$, —(CH$_2$)$_n$—R$^{14}$, —COR$^{13}$, —(CH$_2$)$_n$—CO-Z-R$^{13}$, —CO$_2$R$^{13}$, —CO$_2$—(CH$_2$)$_n$—R$^{13}$, —CO$_2$—(CH$_2$)$_n$—R$^{12}$, —CO$_2$—(CH$_2$)$_n$—CO-Z-R$^{13}$, —CO$_2$—(CH$_2$)$_n$—OR$^{13}$, —CO—(CH$_2$)$_n$—O—(CH$_2$)$_n$—O—(CH$_2$)$_n$—R$^{13}$, —CO—(CH$_2$)$_n$—O(CH$_2$)$_n$—OR$^{13}$, or —CO—NH—(CH$_2$)$_n$—OR$^{13}$;

or R$^{15}$ and R$^{16}$ together form a substituted or an unsubstituted cyclic moiety comprising up to 12 carbon atoms, further comprising at least one additional, optional heteroatom or heterogroup selected independently from —O, —N—, —S, —NR$^6$, —SO$_2$, or —CO; wherein any substituted cyclic moiety is substituted with up to three substituents selected independently from: 1) hydroxyl; 2) an alkyl or a heteroaryl, any of which having up to 12 carbon atoms, wherein any heteroaryl comprises at least one heteroatom or heterogroup selected independently from —O, —N—, —S, or —NR$^6$; or 3) COOR$^{13}$, -Z-(CH$_2$)$_n$—R$^{13}$, —COR$^{13}$, —CO$_2$—(CH$_2$)$_n$—R$^{13}$, —CO(CH$_2$)$_n$—O—R$^{13}$, —(CH$_2$)$_n$—CO$_2$—R$^{13}$, —SOR$^8$, —SO$_2$NR'R", or —NR'R";

wherein the —(CH$_2$)$_n$— linking moiety, in any occurrence, is optionally substituted with at least one group selected independently from hydroxyl, amino, or an alkyl having up to 3 carbon atoms.

2. A compound having the formula:

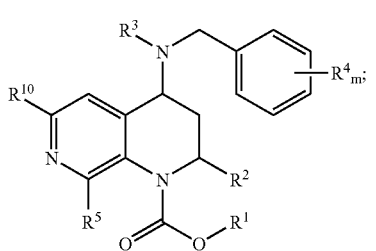

(Ia)

or a salt, a diastereomeric mixture, an enantiomer, a tautomer, a racemic mixture thereof, or any combination thereof, wherein:

R$^1$ is an alkyl, a cycloalkyl, an aryl, an aralkyl, or a heterocyclyl, any of which having up to 12 carbon atoms; wherein the heterocyclyl comprises at least one heteroatom or heterogroup selected independently from —O, —N—, —S, —NR$^6$, —SO$_2$, or —CO;

R$^2$ is selected from an alkyl, a haloalkyl, a cycloalkyl, or a cycloalkyl-substituted alkyl, any of which having up to 12 carbon atoms, or hydrogen;

R$^3$ is selected from: 1) an alkyl having up to 12 carbon atoms; 2) CO$_2$R$^6$, COR$^8$, SO$_2$R$^8$, SO$_2$NR$^6$R$^7$, or CONR$^6$R$^7$; 3) a substituted or an unsubstituted aryl, or a substituted or an unsubstituted 5-, 6-, or 7-membered heterocyclyl or heteroaryl, comprising from 1 to 4 heteroatoms or heterogroups, selected independently from —O, —N—, —S, or —NR$^6$, any of which having up to 12 carbon atoms; or 4) hydrogen or cyano;

wherein when R$^3$ is an aryl, a heterocyclyl, or a heteroaryl, R$^3$ is optionally substituted with up to three substituents selected independently from a halide, a hydroxyl, a cyano, an alkoxy having up to 12 carbon atoms, or R$^{11}$;

R$^4$, in each occurrence, is selected independently from: 1) an alkyl, a cycloalkyl, a haloalkyl, an alkoxy, an aryloxy, a haloalkoxy, an aryl, or a heteroaryl, any of which having up to 12 carbon atoms, wherein any heteroaryl comprises at least one heteroatom or heterogroup selected from —O, —N—, —S, or —NR$^6$; or 2) halogen, hydroxy, or cyano;

m is an integer selected from 0, 1, 2, or 3;

R$^5$ is selected from: 1) an alkyl, a haloalkyl, an alkoxy, a haloalkoxy, or an aryl, any of which having up to 12 carbon atoms; 2) CO$_2$R$^6$ or COR$^8$; or 3) hydrogen, cyano, or hydroxyl;

R$^6$ and R$^7$ are independently an alkyl or a haloalkyl, any of which having up to 12 carbon atoms, or hydrogen;

R$^8$ is an alkyl having up to 12 carbon atoms; and

R$^{10}$ is selected from: 1) an alkyl, a haloalkyl, an alkoxy, a haloalkoxy, or an aryl, any of which having up to 12 carbon atoms; 2) CO$_2$R$^6$ or COR$^8$; or 3) hydrogen, halogen, or cyano;

R$^{11}$ is selected independently from:

1) an alkyl, a haloalkyl, a cycloalkyl, or an alkoxycarbonyl, any of which having up to 12 carbon atoms;

2) a substituted or an unsubstituted heteroaryl or heterocyclyl, any of which having up to 12 carbon atoms, comprises at least one heteroatom or heterogroup selected independently from —O, —N—, —S, —NR$^6$, —SO$_2$, or —CO, wherein any substituted heteroaryl or heterocyclyl is substituted with up to three substituents selected independently from an alkyl having up to 12 carbon atoms or a hydroxyl; or 3) —CO-Z-R$^{13}$, —CO—R$^{12}$, —CO-Z-(CH$_2$)$_n$—CO-Z-R$^{13}$, —NR$^{15}$R$^{16}$, -Z-CO—(CH$_2$)$_{n-Z-R}^{13}$, -Z-CO—(CH$_2$)$_n$—CO-Z-R$^{13}$, —O—(CH$_2$)$_n$—CO-Z-R$^{13}$, —O—(CH$_2$)$_n$—R$^{14}$, —O—R$^{12}$—(CH$_2$)$_n$—R$^{13}$, —O—R$^{14}$—CO—O—R$^{13}$, —O—(CH$_2$)$_n$—R$^{12}$, —O—(CH$_2$)$_n$—NR'R", —O—(CH$_2$)$_n$—CO$_2$—(CH$_2$)$_n$—R$^{13}$, —O—(CH$_2$)$_n$—CONR'R", —O—(CH$_2$)$_n$—SR$^8$, —O—(CH$_2$)$_n$—CO$_2$—R$^{13}$, —O—(CH$_2$)$_n$—O—(CH$_2$)$_n$—OR$^{13}$, —O—(CH$_2$)$_n$—CONR'R", —O—(CH$_2$)$_n$—CONH—(CH$_2$)$_n$—OR$^{13}$, —O—(CH$_2$)$_n$—SO$_2$R$^8$, —O—(CH$_2$)$_n$—R$^{13}$, —O—(CH$_2$)$_n$—OR$^{13}$, —O—(CH$_2$)$_n$—O—(CH$_2$)$_n$—OR$^{13}$, —S—(CH$_2$)$_n$—CONR'R", —SO$_2$—(CH$_2$)$_n$—OR$^{13}$, —SO$_2$—(CH$_2$)$_n$—CONR'R", —(CH$_2$)$_n$—O—CO—R$^8$, —(CH$_2$)$_n$—R$^{12}$, —(CH$_2$)$_n$—R$^{13}$, —(CH$_2$)$_n$—N—(CH$_2$)$_n$—OR$^{13}$, —(CH$_2$)$_n$—CO-Z-R$^{13}$, —(CH$_2$)$_n$-Z-R$^{13}$, or -alkenylene-CO$_2$—(CH$_2$)$_n$—R$^{13}$;

n, in each occurrence, is independently 1, 2, or 3;

R$^{12}$, in each occurrence, is independently selected from a substituted or an unsubstituted heterocyclyl having up to 12 carbon atoms, comprising at least one heteroatom or heterogroup selected independently from —O, —N—, —S, —NR$^6$, —SO$_2$, or —CO, wherein any substituted heterocyclyl is substituted with up to three substituents selected independently from an acyl, an alkyl, or an alkoxycarbonyl, any of which having up to 12 carbon atoms, or —COOH;

R$^{13}$, in each occurrence, is independently selected from: 1) hydrogen; or 2) a cycloalkyl, an aryl, a haloalkyl, a heterocyclyl, or an alkyl group optionally substituted with at least one hydroxyl, any of which having up to 12 carbon atoms, wherein any heterocyclyl comprises at least one heteroatom or heterogroup selected independently from —O, —N—, —S, —NR$^6$, —SO$_2$, or —CO;

R$^{14}$, in each occurrence, is independently selected from a heterocyclyl, a cycloalkyl, or an aryl, any of which having up to 12 carbon atoms, wherein any heterocyclyl comprises at least one heteroatom or heterogroup selected independently from —O, —N—, —S, —NR$^6$, —SO$_2$, or —CO;

Z, in each occurrence, is independently —O or —NR$^6$;

R' and R", in each occurrence, are independently selected from hydrogen or an alkyl having up to 12 carbon atoms; and R$^{15}$ and R$^{16}$, in each occurrence, are independently selected from: 1) hydrogen; 2) an alkyl having up to 12 carbon atoms; or 3) —(CH$_2$)$_n$—O—R$^{13}$, —(CH$_2$)$_n$—R$^{14}$, —COR$^{13}$, —(CH$_2$)$_n$—CO-Z-R$^{13}$, —CO$_2$R$^{13}$, —CO$_2$—(CH$_2$)$_n$—R$^{13}$, —CO$_2$—(CH$_2$)$_n$—R$^{12}$, —CO$_2$—(CH$_2$)$_n$—CO-Z-R$^{13}$, —CO$_2$—(CH$_2$)$_n$—OR$^{13}$, —CO—(CH$_2$)$_n$—O—(CH$_2$)$_n$—O—(CH$_2$)$_n$—R$^{13}$, —CO—(CH$_2$)$_n$—O(CH$_2$)$_n$—OR$^{13}$, or —CO—NH—(CH$_2$)$_n$—OR$^{13}$;

or R$^{15}$ and R$^{16}$ together form a substituted or an unsubstituted cyclic moiety comprising up to 12 carbon atoms, further comprising at least one additional, optional heteroatom or heterogroup selected independently from —O, —N—, —S, —NR$^6$, —SO$_2$, or —CO; wherein any substituted cyclic moiety is substituted with up to three substituents selected independently from: 1) hydroxyl; 2) an alkyl or a heteroaryl, any of which having up to 12 carbon atoms, wherein any heteroaryl comprises at least one heteroatom or heterogroup selected independently from —O, —N—, —S, or —NR$^6$; or 3) COOR$^{13}$, -Z-(CH$_2$)$_n$—R$^{13}$, —COR$^{13}$, —CO$_2$—(CH$_2$)$_n$—R$^{13}$, —CO(CH$_2$)$_n$—O—R$^{13}$, —(CH$_2$)$_n$—CO$_2$—R$^{13}$, —SO$_2$R$^8$, —SO$_2$NR'R", or —NR'R";

wherein the —(CH$_2$)$_n$— linking moiety, in any occurrence, is optionally substituted with at least one group selected independently from hydroxyl, amino, or an alkyl having up to 3 carbon atoms.

3. A compound according to claim 2, wherein:

R$^1$ is an alkyl having up to 6 carbon atoms;

R$^2$ is ethyl;

R$^3$ is selected from: 1) CO$_2$R$^6$2) a substituted or an unsubstituted tetrazolyl, 1,2,4-oxadiazolyl, 1,2,4-oxadiazolyl, oxazolyl, or isooxazolyl, wherein any substituent is selected independently from an alkyl having up to 6 carbon atoms, an alkoxycarbonyl having up to 6 carbon atoms, or a haloalkyl having 1 or 2 carbon atoms; or 3) cyano;

R$^4$, in each occurrence, is selected independently from a halogen, CF$_3$, CN, methyl, or OCF$_3$;

m is 1 or 2;

R$^5$ is selected from: 1) an alkyl, a haloalkyl, an alkoxy, or a haloalkoxy, any of which having 1 or 2 carbon atoms; or 2) hydrogen;

R$^6$ is an alkyl having 1 or 2 carbon atoms; and

R$^{10}$ is selected from: 1) an alkyl, a haloalkyl, an alkoxy, or a haloalkoxy, any of which having 1 or 2 carbon atoms; or 2) hydrogen.

4. A compound according to claim 2, having the formula:

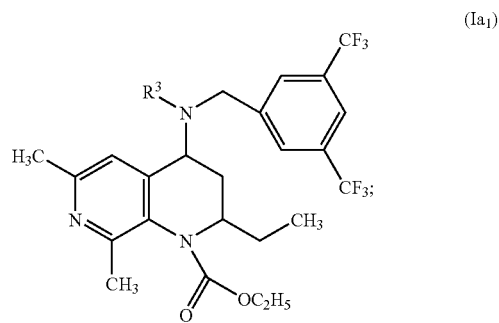

(Ia$_1$)

or a salt, a diastereomeric mixture, an enantiomer, a tautomer, a racemic mixture thereof, or any combination thereof, wherein:

R$^3$ is selected from a substituted or an unsubstituted tetrazolyl, 1,2,4-oxadiazolyl, 1,2,4-oxadiazolyl, oxazolyl, isooxazolyl, alkoxycarbonyl, pyrimidinyl, pyridyl, or thiazolyl; wherein any substituent is selected independently from CF$_3$, methyl, ethyl, ethoxycarbonyl, or tert-butoxycarbonyl.

5. A compound according to claim 2, wherein the compound is:

4-[(3,5-bis-trifluoromethyl-benzyl)-(1H-tetrazol-5-yl)-amino]-2-ethyl-6,8-dimethyl-3,4-dihydro-2H-[1,7]naphthyridine-1-carboxylic acid ethylester;

4-[(3,5-bis-trifluoromethyl-benzyl)-(2-methyl-2H-tetrazol-5-yl)-amino]-2-ethyl-6,8-dimethyl-3,4-dihydro-2H-[1,7]naphthyridine-1-carboxylic acid ethyl ester;

4-[(3,5-bis-trifluoromethyl-benzyl)-(1-methyl-1H-tetrazol-5-yl)-amino]-2-ethyl-6,8-dimethyl-3,4-dihydro-2H-[1,7]naphthyridine-1-carboxylic acid ethyl ester;

4-[(3,5-bis-trifluoromethyl-benzyl)-(5-methyl-[1,3,4]oxadiazol-2-yl)-amino]-2-ethyl-6,8-dimethyl-3,4-dihydro-2H-[1,7]naphthyridine-1-carboxylic acid ethyl ester;

4-[(3,5-Bis-trifluoromethyl-benzyl)-(5-methyl-[1,2,4]oxadiazol-3-yl)-amino]-2-ethyl-6,8-dimethyl-3,4-dihydro-2H-[1,7]naphthyridine-1-carboxylic acid ethyl ester;

4-[(3,5-bis-trifluoromethyl-benzyl)-(2-ethyl-2H-tetrazol-5-yl)-amino]-2-ethyl-6,8-dimethyl-3,4-dihydro-2H-[1,7]naphthyridine-1-carboxylic acid ethyl ester;

4-[(3,5-bis-trifluoromethyl-benzyl)-(4-trifluoromethyl-oxazol-2-yl)-amino]-2-ethyl-6,8-dimethyl-3,4-dihydro-2H-[1,7]naphthyridine-1-carboxylic acid ethyl ester;

4-[(3,5-bis-trifluoromethyl-benzyl)-methoxycarbonyl-amino]-2-ethyl-6,8-dimethyl-3,4-dihydro-2H-[1,7]naphthyridine-1-carboxylic acid ethyl ester;

4-[(3,5-bis-trifluoromethyl-benzyl)-tert-butoxycarbonyl-amino]-2-ethyl-6,8-dimethyl-3,4-dihydro-2H-[1,7]naphthyridine-1-carboxylic acid ethyl ester;

4-[(3,5-bis-trifluoromethyl-benzyl)-pyrimidin-2-yl-amino]-2-ethyl-6,8-dimethyl-3,4-dihydro-2H-[1,7]naphthyridine-1-carboxylic acid ethyl ester;

4-[(3,5-bis-trifluoromethyl-benzyl)-pyridin-2-yl-amino]-2-ethyl-6,8-dimethyl-3,4-dihydro-2H-[1,7]naphthyridine-1-carboxylic acid ethyl ester;

4-[(3,5-bis-trifluoromethyl-benzyl)-(4-methyl-oxazol-2-yl)-amino]-2-ethyl-6,8-dimethyl-3,4-dihydro-2H-[1,7]naphthyridine-1-carboxylic acid ethyl ester;

4-[(3,5-bis-trifluoromethyl-benzyl)-(4-methyl-thiazol-2-yl)-amino]-2-ethyl-6,8-dimethyl-3,4-dihydro-2H-[1,7]naphthyridine-1-carboxylic acid ethyl ester;

4-[(3,5-bis-trifluoromethyl-benzyl)-(5-methyl-isoxazol-3-yl)-amino]-2-ethyl-6,8-dimethyl-3,4-dihydro-2H-[1,7]naphthyridine-1-carboxylic acid ethyl ester;

4-[(3,5-bis-trifluoromethyl-benzyl)-(4-ethoxycarbonyl-oxazol-2-yl)-amino]-2-ethyl-6,8-dimethyl-3,4-dihydro-2H-[1,7]naphthyridine-1-carboxylic acid ethyl ester;

4-[(3,5-bis-trifluoromethyl-benzyl)-(4-trifluoromethyl-oxazol-2-yl)-amino]-2-ethyl-6,8-dimethoxy-3,4-dihydro-2H-[1,7]naphthyridine-1-carboxylic acid ethyl ester;

4-[(3,5-bis-trifluoromethyl-benzyl)-(4-ethoxycarbonyl-oxazol-2-yl)-amino]-2-ethyl-6,8-dimethoxy-3,4-dihydro-2H-[1,7]naphthyridine-1-carboxylic acid ethyl ester;

4-[(3,5-bis-trifluoromethyl-benzyl)-(5-methyl-isoxazol-3-yl)-amino]-2-ethyl-6,8-dimethoxy-3,4-dihydro-2H-[1,7]naphthyridine-1-carboxylic acid ethyl ester;

4-[[5-(4-acetyl-piperazin-1-yl)-pyrimidin-2-yl]-(3,5-bis-trifluoromethyl-benzyl)-amino]-2-ethyl-6,8-dimethyl-3,4-dihydro-2H-[1,7]naphthyridine-1-carboxylic acid ethyl ester;

4-{(3,5-bis-trifluoromethyl-benzyl)-[5-(2-methoxy-acetylamino)-pyrimidin-2-yl]-amino}-2-ethyl-6,8-dimethyl-3,4-dihydro-2H-[1,7]naphthyridine-1-carboxylic acid ethyl ester;

4-{(3,5-bis-trifluoromethyl-benzyl)-[5-(2-morpholin-4-yl-ethoxy)-pyrimidin-2-yl]-amino}-2-ethyl-6,8-dimethyl-3,4-dihydro-2H-[1,7]naphthyridine-1-carboxylic acid ethyl ester;

4-[(3,5-bis-trifluoromethyl-benzyl)-(5-morpholin-4-yl-pyrimidin-2-yl)-amino]-2-ethyl-6,8-dimethyl-3,4-dihydro-2H-[1,7]naphthyridine-1-carboxylic acid ethyl ester;

4-[(3,5-bis-trifluoromethyl-benzyl)-(5-morpholin-4-yl-pyridin-2-yl)-amino]-2-ethyl-6,8-dimethyl-3,4-dihydro-2H-[1,7]naphthyridine-1-carboxylic acid ethyl ester;

4-{(3,5-bis-trifluoromethyl-benzyl)-[5-(2H-tetrazol-5-yl)-pyridin-2-yl]-amino}-2-ethyl-6,8-dimethyl-3,4-dihydro-2H-[1,7]naphthyridine-1-carboxylic acid ethyl ester;

4-{(3,5-bis-trifluoromethyl-benzyl)-[5-(pyrrolidine-1-carbonyl)-pyrimidin-2-yl]amino}-2-ethyl-6,8-dimethyl-3,4-dihydro-2H-[1,7]naphthyridine-1-carboxylic acid ethyl ester;

4-[{5-[bis-(2-methoxy-ethyl)-amino]-pyrimidin-2-yl}-(3,5-bis-trifluoromethyl-benzyl)-amino]-2-ethyl-6,8-dimethyl-3,4-dihydro-2H-[1,7]naphthyridine-1-carboxylic acid ethyl ester;

4-{(3,5-bis-trifluoromethyl-benzyl)-[5-(3-ethoxycarbonyl-piperidin-1-yl)-pyrimidin-2-yl]-amino}-2-ethyl-6,8-dimethyl-3,4-dihydro-2H-[1,7]naphthyridine-1-carboxylic acid ethyl ester;

4-{(3,5-bis-trifluoromethyl-benzyl)-[5-(2-hydroxy-ethylamino)-pyrimidin-2-yl]-amino}-2-ethyl-6,8-dimethyl-3,4-dihydro-2H-[1,7]naphthyridine-1-carboxylic acid ethyl ester;

4-{(3,5-bis-trifluoromethyl-benzyl)-[4-(3-carboxy-propoxy)-pyrimidin-2-yl]-amino}-2-ethyl-6,8-dimethyl-3,4-dihydro-2H-[1,7]naphthyridine-1-carboxylic acid ethyl ester;

4-{(3,5-bis-trifluoromethyl-benzyl)-[5-(2-methylsulfanyl-ethoxy)-pyrimidin-2-yl]-amino}-2-ethyl-6,8-dimethyl-3,4-dihydro-2H-[1,7]naphthyridine-1-carboxylic acid ethyl ester;

4-((3,5-bis-trifluoromethyl-benzyl)-{5-[(2-tert-butoxycarbonyl-ethyl)-methyl-amino]-pyrimidin-2-yl}-amino)-2-ethyl-6,8-dimethyl-3,4-dihydro-2H-[1,7]naphthyridine-1-carboxylic acid ethyl ester;

4-{(3,5-bis-trifluoromethyl-benzyl)-[5-(2-carboxy-ethyl)-pyrimidin-2-yl]-amino}-2-ethyl-6,8-dimethyl-3,4-dihydro-2H-[1,7]naphthyridine-1-carboxylic acid ethyl ester; or any combination thereof.

6. A composition comprising a pharmaceutically acceptable carrier and at least one compound having the formula:

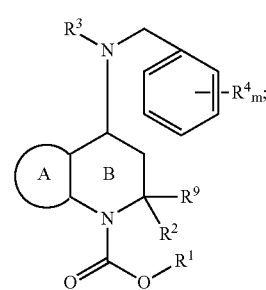

(I)

or a salt, a diastereomeric mixture, an enantiomer, a tautomer, a racemic mixture thereof, or any combination thereof, wherein:

ring A is fused to ring B and is selected from:

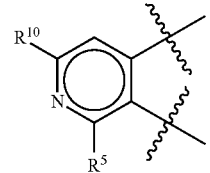

$R^1$ is an alkyl, a cycloalkyl, a haloalkyl, an aryl, an aralkyl, a heteroaryl, or a heterocyclyl, any of which having up to 12 carbon atoms; wherein any heteroaryl or heterocyclyl comprises at least one heteroatom or heterogroup selected independently from —O—, —N—, —S, —NR$^6$, —SO$_2$, or —CO;

$R^2$ and $R^9$ are the same or different, and are selected independently from an alkyl, a haloalkyl, a cycloalkyl, or a cycloalkyl-substituted alkyl, any of which having up to 12 carbon atoms, or hydrogen;

$R^3$ is selected from: 1) an alkyl having up to 12 carbon atoms; 2) $CO_2R^6$, $COR^8$, $SO_2R^8$, $SO_2NR^6R^7$, or $CONR^6R^7$; 3) a substituted or an unsubstituted aryl, or a substituted or an unsubstituted 5-, 6-, or 7-membered heterocyclyl or heteroaryl, comprising from 1 to 4 heteroatoms or heterogroups, selected independently from —O—, —N—, —S, or —NR$^6$, any of which having up to 12 carbon atoms; or 4) hydrogen or cyano;

wherein when $R^3$ is an aryl, a heterocyclyl, or a heteroaryl, $R^3$ is optionally substituted with up to three substituents selected independently from a halide, a hydroxyl, a cyano, an alkoxy having up to 12 carbon atoms, or $R^{11}$;

$R^4$, in each occurrence, is selected independently from: 1) an alkyl, a cycloalkyl, a haloalkyl, an alkoxy, an aryloxy, a haloalkoxy, an aryl, or a heteroaryl, any of which having up to 12 carbon atoms, wherein any heteroaryl comprises at least one heteroatom or heterogroup selected from —O—, —N—, —S, or —NR$^6$; or 2) halogen, hydroxy, or cyano;

m is an integer selected from 0, 1, 2, or 3;

$R^5$ is selected from: 1) an alkyl, a haloalkyl, an alkoxy, a haloalkoxy, or an aryl, any of which having up to 12 carbon atoms; 2) $CO_2R^6$ or $COR^8$ or 3) hydrogen, cyano, or hydroxyl;

$R^6$ and $R^7$ are independently an alkyl or a haloalkyl, any of which having up to 12 carbon atoms, or hydrogen;

$R^8$ is an alkyl having up to 12 carbon atoms; and $R^{10}$ is selected from: 1) an alkyl, a haloalkyl, an alkoxy, a haloalkoxy, or an aryl, any of which having up to 12 carbon atoms; 2) $CO_2R^6$ or $COR^8$; or 3) hydrogen, halogen, or cyano;

$R^{11}$ is selected independently from:
1) an alkyl, a haloalkyl, a cycloalkyl, or an alkoxycarbonyl, any of which having up to 12 carbon atoms;
2) a substituted or an unsubstituted heteroaryl or heterocyclyl, any of which having up to 12 carbon atoms, comprises at least one heteroatom or heterogroup selected independently from —O—, —N—, —S, —NR$^6$, —SO$_2$, or —CO, wherein any substituted heteroaryl or heterocyclyl is substituted with up to three substituents selected independently from an alkyl having up to 12 carbon atoms or a hydroxyl; or
3) —CO-Z-R$^{13}$, —CO—R$^{12}$, —CO-Z-(CH$_2$)$_n$—CO-Z-R$^{13}$, —NR$^{15}$R$^{16}$, -Z-CO—(CH$_2$)$_n$-Z-R$^{13}$, -Z-CO—(CH$_2$)$_n$—CO-Z-R$^{13}$, —O—(CH$_2$)$_n$—CO-Z-R$^{13}$, —O—(CH$_2$)$_n$—R$^{13}$, —O—R$^{12}$—(CH$_2$)$_n$—R$^{13}$, —O—R$^{14}$—CO—O—R$^{13}$, —O—(CH$_2$)$_n$—R$^{12}$, —O—(CH$_2$)$_n$—NR'R'', —O—(CH$_2$)$_n$—CO$_2$—(CH$_2$)$_n$—R$^{13}$, —O—(CH$_2$)$_n$—CONR'R'', —O—(CH$_2$)$_n$—SR$^8$, —O—(CH$_2$)$_n$—CO$_2$—R$^{13}$, —O—(CH$_2$)$_n$—O—(CH$_2$)$_n$—OR$^{13}$, —O—(CH$_2$)$_n$—CONR'R'', —O—(CH$_2$)$_n$—CONH—(CH$_2$)$_n$—OR$^{13}$, —O—(CH$_2$)$_n$—SO$_2$R$^8$, —O—(CH$_2$)$_n$—R$^{13}$, —O—(CH$_2$)$_n$—OR$^{13}$, —O—(CH$_2$)$_n$—O—(CH$_2$)$_n$—OR$^{13}$, —S—(CH$_2$)$_n$—CONR'R'', —SO$_2$—(CH$_2$)$_n$—OR$^{13}$, —SO$_2$—(CH$_2$)$_n$—CONR'R'', —(CH$_2$)$_n$—O—CO—R$^8$, —(CH$_2$)$_n$—R$^{12}$, —(CH$_2$)$_n$—R$^{13}$, —(CH$_2$)$_n$—N—(CH$_2$)$_n$—OR$^{13}$, —(CH$_2$)$_n$—CO-Z-R$^{13}$, —(CH$_2$)$_n$-Z-R$^{13}$, or -alkenylene-CO$_2$—(CH$_2$)$_n$—R$^{13}$;

n, in each occurrence, is independently 1, 2, or 3;

$R^{12}$, in each occurrence, is independently selected from a substituted or an unsubstituted heterocyclyl having up to 12 carbon atoms, comprising at least one heteroatom or heterogroup selected independently from —O—, —N—, —S, —NR$^6$, —SO$_2$, or —CO, wherein any substituted heterocyclyl is substituted with up to three substituents selected independently from an acyl, an alkyl, or an alkoxycarbonyl, any of which having up to 12 carbon atoms, or —COOH;

$R^{13}$, in each occurrence, is independently selected from: 1) hydrogen; or 2) a cycloalkyl, an aryl, a haloalkyl, a heterocyclyl, or an alkyl group optionally substituted with at least one hydroxyl, any of which having up to 12 carbon atoms, wherein any heterocyclyl comprises at least one heteroatom or heterogroup selected independently from —O—, —N—, —S, —NR$^6$, —SO$_2$, or —CO;

$R^{14}$, in each occurrence, is independently selected from a heterocyclyl, a cycloalkyl, or an aryl, any of which having up to 12 carbon atoms, wherein any heterocyclyl comprises at least one heteroatom or heterogroup selected independently from —O—, —N—, —S, —NR$^6$, —SO$_2$, or —CO;

Z, in each occurrence, is independently —O or —NR$^6$;

R' and 5'', in each occurrence, are independently selected from hydrogen or an alkyl having up to 12 carbon atoms; and $R^{15}$ and $R^{16}$, in each occurrence, are independently selected from: 1) hydrogen; 2) an alkyl having up to 12 carbon atoms; or 3) —(CH$_2$)$_n$—O—R$^{13}$, —(CH$_2$)$_n$—R$^{14}$, —COR$^{13}$, —(CH$_2$)$_n$—CO-Z-R$^{13}$, —CO$_2$R$^{13}$, —CO$_2$—(CH$_2$)$_n$—R$^{13}$, —CO$_2$—(CH$_2$)$_n$—R$^{12}$, —CO$_2$—(CH$_2$)$_n$—CO-Z-R$^{13}$, —CO$_2$—(CH$_2$)$_n$—OR$^{13}$, —CO—(CH$_2$)$_n$—O—(CH$_2$)$_n$—O—(CH$_2$)$_n$—R$^{13}$, —CO—(CH$_2$)$_n$—O(CH$_2$)$_n$—OR$^{13}$, or —CO—NH—(CH$_2$)$_n$—OR$^{13}$;

or $R^{15}$ and $R^{16}$ together form a substituted or an unsubstituted cyclic moiety comprising up to 12 carbon atoms, further comprising at least one additional, optional heteroatom or heterogroup selected independently from —O—, —N—, —S, —NR$^6$, —SO$_2$, or —CO; wherein any substituted cyclic moiety is substituted with up to three substituents selected independently from: 1) hydroxyl; 2) an alkyl or a heteroaryl, any of which having up to 12 carbon atoms, wherein any heteroaryl comprises at least one heteroatom or heterogroup selected independently from —O—, —N—, —S, or —NR$^6$; or 3) COOR$^{13}$, -Z-(CH$_2$)$_n$—R$^{13}$, —COR$^{13}$, —CO$_2$—(CH$_2$)$_n$—R$^{13}$, —CO(CH$_2$)$_n$—O—R$^{13}$, —(CH$_2$)$_n$—CO$_2$—R$^{13}$, —SO$_2$R$^8$, —SO$_2$NR'R'', or —NR'R'';

wherein the —(CH$_2$)$_n$— linking moiety, in any occurrence, is optionally substituted with at least one group selected independently from hydroxyl, amino, or an alkyl having up to 3 carbon atoms.

7. The composition as claimed in claim 6, further comprising:

optionally, a pharmaceutically acceptable auxiliary;
optionally, a pharmaceutically acceptable preservative;
optionally, a pharmaceutically acceptable excipient;
optionally, a pharmaceutically acceptable diluent; and
optionally, a pharmaceutically acceptable solvate.

8. The composition as claimed in claim 7, wherein the composition is in the form of a tablet, a capsule, a cachet, a powder, a granule, a solution, a suspension, an emulsion, a bolus, a lozenge, a suppository, a pessary, a tampon, a cream, a gel, a paste, a foam, a spray, an aerosol, a microcapsule, a liposome, a transdermal patch, a pastille, a paste, or a mouthwash.

9. A composition comprising a pharmaceutically acceptable carrier and at least one compound having the formula:

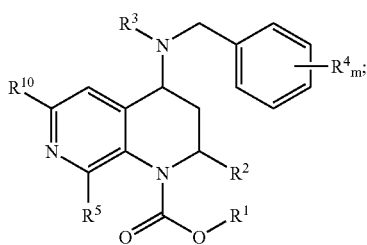

(Ia)

or a salt, a diastereomeric mixture, an enantiomer, a tautomer, a racemic mixture thereof, or any combination thereof, wherein:

$R^1$ is an alkyl, a cycloalkyl, an aryl, an aralkyl, or a heterocyclyl, any of which having up to 12 carbon atoms; wherein the heterocyclyl comprises at least one heteroatom or heterogroup selected independently from —O, —N—, —S, —NR$^6$, —SO$_2$, or —CO;

$R^2$ is selected from an alkyl, a haloalkyl, a cycloalkyl, or a cycloalkyl substituted alkyl, any of which having up to 12 carbon atoms, or hydrogen;

$R^3$ is selected from: 1) an alkyl having up to 12 carbon atoms; 2) CO$_2$R$^6$, COR$^8$, SO$_2$R$^8$, SO$_2$NR$^6$R$^7$, or CONR$^6$R$^7$3) a substituted or an unsubstituted aryl, or a substituted or an unsubstituted 5-, 6-, or 7-membered heterocyclyl or heteroaryl, comprising from 1 to 4 heteroatoms or heterogroups, selected independently from —O, —N—, —S, or —NR$^6$, any of which having up to 12 carbon atoms; or 4) hydrogen or cyano;

wherein when $R^3$ is an aryl, a heterocyclyl, or a heteroaryl, $R^3$ is optionally substituted with up to three substituents selected independently from a halide, a hydroxyl, a cyano, an alkoxy having up to 12 carbon atoms, or $R^{11}$;

$R^4$, in each occurrence, is selected independently from: 1) an alkyl, a cycloalkyl, a haloalkyl, an alkoxy, an aryloxy, a haloalkoxy, an aryl, or a heteroaryl, any of which having up to 12 carbon atoms, wherein any heteroaryl comprises at least one heteroatom or heterogroup selected from —O, —N—, —S, or —NR$^6$; or 2) halogen, hydroxy, or cyano;

m is an integer selected from 0, 1, 2, or 3;

$R^5$ is selected from: 1) an alkyl, a haloalkyl, an alkoxy, a haloalkoxy, or an aryl, any of which having up to 12 carbon atoms; 2) CO$_2$R$^6$ or COR$^8$; or 3) hydrogen, cyano, or hydroxyl;

$R^6$ and $R^7$ are independently an alkyl or a haloalkyl, any of which having up to 12 carbon atoms, or hydrogen;

$R^8$ is an alkyl having up to 12 carbon atoms; and $R^{10}$ is selected from: 1) an alkyl, a haloalkyl, an alkoxy, a haloalkoxy, or an aryl, any of which having up to 12 carbon atoms; 2) CO$_2$R$^6$ or COR$^8$; or 3) hydrogen, halogen, or cyano;

$R^{11}$ is selected independently from:
1) an alkyl, a haloalkyl, a cycloalkyl, or an alkoxycarbonyl, any of which having up to 12 carbon atoms;
2) a substituted or an unsubstituted heteroaryl or heterocyclyl, any of which having up to 12 carbon atoms, comprises at least one heteroatom or heterogroup selected independently from —O, —N—, —S, —NR$^6$, —SO$_2$, or —CO, wherein any substituted heteroaryl or heterocyclyl is substituted with up to three substituents selected independently from an alkyl having up to 12 carbon atoms or a hydroxyl; or 3) —CO-Z-R$^{13}$, —CO—R$^{12}$, —CO-Z-(CH$_2$)$_n$—CO-Z-R$^{13}$, —NR$^{15}$R$^{16}$, -Z-CO—(CH$_2$)$_n$-Z-R$^{13}$, -Z-CO—(CH$_2$)$_n$—CO-Z-R$^{13}$, —O—(CH$_2$)$_n$—CO-Z-R$^{13}$, —O—(CH$_2$)$_n$—R$^{14}$, —O—R$^{12}$—(CH$_2$)$_n$—R$^{13}$, —O—R$^{14}$—CO—O—R$^{13}$, —O—(CH$_2$)$_n$—R$^{12}$, —O—(CH$_2$)$_n$—NR'R, —O—(CH$_2$)$_n$—CO$_2$—(CH$_2$)$_n$—R$^{13}$, —O—(CH$_2$)$_n$—CONR'R'', —O—(CH$_2$)$_n$—SR$^8$, —O—(CH$_2$)$_n$—CO$_2$—R$^{13}$, —O—(CH$_2$)$_n$—O—(CH$_2$)$_n$—OR$^{13}$, —O—(CH$_2$)$_n$—CONR'R'', —O—(CH$_2$)$_n$—CONH—(CH$_2$)$_n$—OR$^{13}$, —O—(CH$_2$)$_n$—SO$_2$R$^8$, —O—(CH$_2$)$_n$—R$^{13}$, —O—(CH$_2$)$_n$—OR$^{13}$, —O—(CH$_2$)$_n$—O—(CH$_2$)$_n$—OR$^{13}$, —S—(CH$_2$)$_n$—CONR'R'', —SO$_2$—(CH$_2$)$_n$—OR$^{13}$, —SO$_2$—(CH$_2$)$_n$—CONR'R'', —(CH$_2$)$_n$—O—CO—R$^8$, —(CH$_2$)$_n$—R$^{12}$, —(CH$_2$)$_n$—R$^{13}$, —(CH$_2$)$_n$—N—(CH$_2$)$_n$—OR$^{13}$, —(CH$_2$)$_n$—CO-Z-R$^{13}$, —(CH$_2$)$_n$-Z-R$^{13}$, or -alkenylene-CO$_2$—(CH$_2$)$_n$—R$^{13}$;

n, in each occurrence, is independently 1, 2, or 3;

$R^{12}$, in each occurrence, is independently selected from a substituted or an unsubstituted heterocyclyl having up to 12 carbon atoms, comprising at least one heteroatom or heterogroup selected independently from —O, —N—, —S, —NR$^6$, —SO$_2$, or —CO, wherein any substituted heterocyclyl is substituted with up to three substituents selected independently from an acyl, an alkyl, or an alkoxycarbonyl, any of which having up to 12 carbon atoms, or —COOH;

$R^{13}$, in each occurrence, is independently selected from: 1) hydrogen; or 2) a cycloalkyl, an aryl, a haloalkyl, a heterocyclyl, or an alkyl group optionally substituted with at least one hydroxyl, any of which having up to 12 carbon atoms, wherein any heterocyclyl comprises at least one heteroatom or heterogroup selected independently from —O, —N—, —S, —NR$^6$, —SO$_2$, or —CO;

$R^{14}$, in each occurrence, is independently selected from a heterocyclyl, a cycloalkyl, or an aryl, any of which having up to 12 carbon atoms, wherein any heterocyclyl comprises at least one heteroatom or heterogroup selected independently from —O, —N—, —S, —NR$^6$, —SO$_2$, or —CO;

Z, in each occurrence, is independently —O or —NR$^6$; R' and R'', in each occurrence, are independently selected from hydrogen or an alkyl having up to 12 carbon atoms; and $R^{15}$ and $R^{16}$, in each occurrence, are independently selected from: 1) hydrogen; 2) an alkyl having up to 12 carbon atoms; or 3) —(CH$_2$)$_n$—O—R$^{13}$, —(CH$_2$)$_n$—R$^{14}$, —COR$^{13}$, —(CH$_2$)$_n$—CO-Z-R$^{13}$, —CO$_2$R$^{13}$, —CO$_2$—(CH$_2$)$_n$—R$^{13}$, —CO$_2$—(CH$_2$)$_n$—R$^{12}$, —CO$_2$—(CH$_2$)$_n$—CO-Z-R$^{13}$, —CO$_2$—(CH$_2$)$_n$—OR$^{13}$, —CO—(CH$_2$)$_n$—O—(CH$_2$)$_n$—O—(CH$_2$)$_n$—R$^{13}$, —CO—(CH$_2$)$_n$—O(CH$_2$)$_n$—OR$^{13}$, or —CO—NH—(CH$_2$)$_n$—OR$^{13}$;

or $R^{15}$ and $R^{16}$ together form a substituted or an unsubstituted cyclic moiety comprising up to 12 carbon atoms, further comprising at least one additional, optional heteroatom or heterogroup selected independently from —O, —N—, —S, —NR$^6$, —SO$_2$, or —CO; wherein any substituted cyclic moiety is substituted with up to three substituents selected independently from: 1) hydroxyl; 2) an alkyl or a heteroaryl, any of which having up to 12 carbon atoms, wherein any heteroaryl comprises at least one heteroatom or heterogroup selected independently from —O, —N—, —S, or —NR$^6$; or 3) COOR$^{13}$, -Z-(CH$_2$)$_n$—R$^{13}$, —COR$^{13}$, —CO$_2$—(CH$_2$)$_n$ $-R^{13}$, $-CO(CH_2)_n-O-R^{13}$, $-(CH_2)_n-CO_2-R^{13}$, $-SO_2R^8$, $-SO_2NR'R''$, or $-NR'R''$;

wherein the $-(CH_2)_n-$ linking moiety, in any occurrence, is optionally substituted with at least one group selected independently from hydroxyl, amino, or an alkyl having up to 3 carbon atoms.

10. The composition as claimed in claim 9, further comprising:

optionally, a pharmaceutically acceptable auxiliary;
optionally, a pharmaceutically acceptable preservative;
optionally, a pharmaceutically acceptable excipient;
optionally, a pharmaceutically acceptable diluent; and
optionally, a pharmaceutically acceptable solvate.

11. The composition as claimed in claim 9, wherein the composition is in the form of a tablet, a capsule, a cachet, a powder, a granule, a solution, a suspension, an emulsion, a bolus, a lozenge, a suppository, a pessary, a tampon, a cream, a gel, a paste, a foam, a spray, an aerosol, a microcapsule, a liposome, a transdermal patch, a pastille, a paste, or a mouthwash.

* * * * *